United States Patent
Yamazaki et al.

(10) Patent No.: US 11,965,180 B2
(45) Date of Patent: Apr. 23, 2024

(54) CANCER STEM CELL POPULATION AND METHOD FOR PRODUCTION THEREOF

(71) Applicant: CHUGAI SEIYAKU KABUSHIKI KAISHA, Tokyo (JP)

(72) Inventors: Tatsumi Yamazaki, Tokyo (JP); Hisafumi Okabe, Shizuoka (JP); Shinta Kobayashi, Helios (SG); Yu Jau Chen, Helios (SG); Atsuhiko Kato, Shizuoka (JP); Masami Suzuki, Shizuoka (JP); Koichi Matsubara, Helios (SG)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 822 days.

(21) Appl. No.: 16/994,388

(22) Filed: Aug. 14, 2020

(65) Prior Publication Data
US 2020/0385686 A1    Dec. 10, 2020

Related U.S. Application Data

(62) Division of application No. 13/878,181, filed as application No. PCT/JP2011/073067 on Oct. 6, 2011, now Pat. No. 11,124,773.

(30) Foreign Application Priority Data

Oct. 6, 2010  (JP) ................................ 2010-226301

(51) Int. Cl.
*C12N 5/095*  (2010.01)
*G01N 33/50*  (2006.01)

(52) U.S. Cl.
CPC ....... *C12N 5/0695* (2013.01); *G01N 33/5011* (2013.01); *G01N 33/5073* (2013.01)

(58) Field of Classification Search
None
See application file for complete search history.

(56) References Cited

U.S. PATENT DOCUMENTS

| | | | |
|---|---|---|---|
| 5,573,924 | A | 11/1996 | Beckmann et al. |
| 7,145,055 | B2 | 12/2006 | Ito et al. |
| 7,951,549 | B2 | 5/2011 | Haley et al. |
| 8,067,546 | B2 | 11/2011 | McDonagh et al. |
| 2002/0119565 | A1 | 8/2002 | Clarke et al. |
| 2007/0220621 | A1 | 9/2007 | Clarke et al. |
| 2008/0064049 | A1 | 3/2008 | Clarke et al. |
| 2008/0178305 | A1 | 7/2008 | Clarke et al. |
| 2008/0268476 | A1 | 10/2008 | Lopez |
| 2009/0081221 | A1 | 3/2009 | Tokoro et al. |
| 2009/0214517 | A1 | 8/2009 | Wong et al. |
| 2009/0226396 | A1 | 9/2009 | Haley et al. |
| 2009/0324491 | A1 | 12/2009 | Aburatani et al. |
| 2010/0003265 | A1 | 1/2010 | Scheffler et al. |
| 2010/0024049 | A1 | 1/2010 | Marchiano |
| 2010/0275280 | A1 | 10/2010 | Clevers et al. |
| 2010/0287638 | A1 | 11/2010 | Dirks et al. |
| 2011/0182904 | A1 | 7/2011 | Zimmerman et al. |
| 2011/0244502 | A1 | 10/2011 | Ince et al. |
| 2013/0019327 | A1 | 1/2013 | Suzuki et al. |
| 2013/0288248 | A1 | 10/2013 | Yamazaki et al. |
| 2014/0039033 | A1 | 2/2014 | Song et al. |
| 2014/0302511 | A1 | 10/2014 | Yamazaki et al. |
| 2014/0314675 | A1 | 10/2014 | Yamazaki et al. |
| 2016/0017028 | A1 | 1/2016 | Yoshida et al. |
| 2016/0159904 | A1 | 6/2016 | Yamazaki et al. |
| 2020/0325222 | A1 | 10/2020 | Yamazaki et al. |

FOREIGN PATENT DOCUMENTS

| | | |
|---|---|---|
| CA | 2 447 400 | 3/2005 |
| CN | 101014608 A | 8/2007 |
| CN | 101506352 | 8/2009 |
| EP | 1 338 198 A1 | 8/2003 |
| EP | 1 637 589 A1 | 3/2006 |
| EP | 1 686 173 A1 | 8/2006 |
| EP | 1 792 979 | 6/2007 |
| EP | 1815864 | 8/2007 |
| EP | 2070548 | 6/2009 |

(Continued)

OTHER PUBLICATIONS

Friedrich et al. Spheroid-based Drug Screen: Considerations and Practical Approach. Nature Protocols, 2009. 4(3): 309-324.*
Sanz et al., "Differential transplantability of human endothelial cells in colorectal cancer and renal cell carcinoma primary xenografts," *Laboratory Investigation*, 89: 91-97, 2009.
Gullo et al., "Inhibition of Proliferation and Induction of Apoptosis in Multiple Myeloma Cell Lines by CD137 Ligand Signaling," *PLoS One*, 5(5):e10845 (11 pages), 2010.
HPAC-CRL-2119 (ATCC, https://www.atcc.org/products/crl-2119, dated Jan. 14, 2023, 7 pages).
U.S. Appl. No. 13/519,059, US 2013/019327.
U.S. Appl. No. 13/878,181, US 2013/288248.

(Continued)

*Primary Examiner* — Allison M Fox
*Assistant Examiner* — Kimberly A Aron
(74) *Attorney, Agent, or Firm* — Klarquist Sparkman, LLP

(57) ABSTRACT

Provided is a cancer stem cell mass from which cells incapable of forming cancer are substantially removed and which has a characteristic property of reproducing a layered structure of a cancer tissue; a process for producing the cancer stem cell mass; and use of the cancer stem cell mass. A human cancer tissue was repeatedly grown in a NOG mouse, separated cancer cells from the grown cancer tissue, and tested and compared various cancer cell culture processes. As a result, a cancer stem cell composition which is homogeneous and is substantially free of the coexistence of cells capable of forming cancer and cells incapable of forming cancer in a mixed state can be produced successively by employing an attached culture process using a serum-free stem cell culture medium rather than a generally employed floating culture process.

4 Claims, 41 Drawing Sheets
Specification includes a Sequence Listing.

(56) References Cited

FOREIGN PATENT DOCUMENTS

| EP | 2517555 | 10/2012 | | |
|---|---|---|---|---|
| EP | 2626414 A1 | 8/2013 | | |
| JP | 2005-206508 | 8/2005 | | |
| JP | 3753321 | 12/2005 | | |
| JP | 2007-530588 | 11/2007 | | |
| JP | 2008-500838 | 1/2008 | | |
| JP | 2008-102012 | 5/2008 | | |
| JP | 2008-514205 | 5/2008 | | |
| JP | 2008-182912 | 8/2008 | | |
| JP | 2009-502156 | 1/2009 | | |
| JP | 2009-509510 | 3/2009 | | |
| JP | 2009-519242 | 5/2009 | | |
| JP | 2009-539374 | 11/2009 | | |
| JP | 2010-516259 | 5/2010 | | |
| JP | 2011-519567 | 7/2011 | | |
| WO | WO 02/12447 | 2/2002 | | |
| WO | WO 03/104401 | 12/2003 | | |
| WO | WO 2004/101775 A1 | 11/2004 | | |
| WO | WO 2005/035740 A1 | 4/2005 | | |
| WO | WO 2005/092927 | 10/2005 | | |
| WO | WO 2005/118824 | 12/2005 | | |
| WO | WO 2006/039671 | 4/2006 | | |
| WO | WO 2006/039678 A2 | 4/2006 | | |
| WO | WO 2006/051405 | 5/2006 | | |
| WO | WO 2006/051984 A1 | 5/2006 | | |
| WO | WO 2006/138275 | 12/2006 | | |
| WO | WO 2007/012811 | 2/2007 | | |
| WO | WO 2007/038637 | 4/2007 | | |
| WO | WO 2007/064945 | 6/2007 | | |
| WO | WO 2007/124125 A2 | 11/2007 | | |
| WO | WO 2007/132883 A1 | 11/2007 | | |
| WO | WO 2007/145901 | 12/2007 | | |
| WO | WO 2008/017171 | 2/2008 | | |
| WO | WO-2008033393 A2 * | 3/2008 | ........... | C12N 5/0693 |
| WO | WO-2008034645 A1 * | 3/2008 | ....... | G01N 33/57419 |
| WO | WO 2008/047723 | 4/2008 | | |
| WO | WO 2008/091908 | 7/2008 | | |
| WO | WO 2008/143954 | 11/2008 | | |
| WO | WO 2008/149803 | 12/2008 | | |
| WO | WO 2009/005809 | 1/2009 | | |
| WO | WO 2009/045201 A1 | 4/2009 | | |
| WO | WO 2009/064301 | 5/2009 | | |
| WO | WO 2009/135181 | 11/2009 | | |
| WO | WO 2010/009121 | 1/2010 | | |
| WO | WO 2010/016766 | 2/2010 | | |
| WO | WO 2010/067487 | 6/2010 | | |
| WO | WO 2010/102244 | 9/2010 | | |
| WO | WO 2010/113117 | 10/2010 | | |
| WO | WO 2010/123891 | 10/2010 | | |
| WO | WO 2010/126074 | 11/2010 | | |
| WO | WO 2011/027308 | 3/2011 | | |
| WO | WO 2011/078301 | 6/2011 | | |
| WO | WO 2011/083088 | 7/2011 | | |
| WO | WO 2012/046797 A1 | 4/2012 | | |
| WO | WO 2012/096545 A2 | 7/2012 | | |
| WO | WO 2013/035824 | 3/2013 | | |
| WO | WO 2013/062083 | 5/2013 | | |

OTHER PUBLICATIONS

U.S. Appl. No. 14/343,364, U.S. Pat. No. 10,018,630.
U.S. Appl. No. 14/354,517, US 2014/302511.
U.S. Appl. No. 15/042,548, US 2016/0159904.
U.S. Appl. No. 16/913,341, Not yet published.
Fujii et al., "The potential of the NOD/SCID$_{\gamma_c}$$^{null}$ (NOG) mouse as an in vivo human tissue model," Toxicol Pathol 191-P53 (Jan. 2007).
Enfortumab Vedotin (ASG-22ME) | ADC Review, In Press Media Group, Jul. 29, 2016: http://adcreview.com/enfortumab-vedotin-asg-22me-formerly-ags-22m6e-clinical-trials/ (1 page).
Al-Hajj et al., "Prospective identification of tumorigenic breast cancer cells." Proceedings of the National Academy of Sciences 100:3983-3988, 2003 (Epub Mar. 10, 2003).
Almagro et al., "Humanization of antibodies" Front Biosci 13:1619-1633, 2008.
Amendment and Response after Final Action, dated Mar. 6, 2015 in connection with U.S. Appl. No. 13/519,059, in response to the Final Office Action dated Sep. 19, 2014.
Amendment and Response to Non-Final Office Action, dated Nov. 5, 2015, in U.S. Appl. No. 13/519,059 (7 pages).
Amendment and Response to Office Action for U.S. Appl. No. 13/519,059, submitted to the U.S. PTO dated Jun. 9, 2014 (7 pages).
Amendment and Response to Restriction Requirement filed Sep. 19, 2013, U.S. Appl. No. 13/519,059, 4 pages.
Barker et al., "Crypt stem cells as the cells-of-origin of intestinal cancer." Nature 457: 608-611, 2009 (Epub Dec. 17, 2008).
Barker et al., "Identification of stem cells in small intestine and colon by marker gene Lgr5." Nature 449: 1003-1007, 2007 (Epub Oct. 14, 2007).
Boiko et al., "Human melanoma-initiating cells express neural crest nerve growth factor receptor CD271." Nature 466(7302): 133-137, 2010.
Bonnet et al., "Human acute myeloid leukemia is organized as a hierarchy that originates from a primitive hematopoietic cell." Nature Medicine 3: 730-737, 1997.
Botchkina et al., "Phenotypic Subpopulations of Metastatic Colon Cancer Stem Cells: Genomic Analysis," Cancer Genomic & Proteomics, 6: 19-30, 2009.
Brabletz et al., "Migrating cancer stem cells—an integrated concept of malignant tumour progression," Nature Reviews Cancer, 5:744-749 (2005).
Carlone et al., "Slowly cycling versus rapidly cycling intestinal stem cells," Cell Cycle 10(5):723-724, 2011.
Chen et al., "Intestinal Adenomagenesis Involves Core Molecular Signatures of the Epithelial-Mesenchymal Transition," J Mol Histol 39(3):283-294, 2008.
Chu et al., "Characterization of a subpopulation of colon cancer cells with stem cell-like properties." International Journal of Cancer 124: 1312-1321, 2009.
Clevers. "The cancer stem cell: premises, promises and challenges." Nature Medicine 17:313-319, 2011.
Cobleigh, "Other Options in the Treatment of Advanced Breast Cancer," Seminars Oncol 38(Suppl 2):S11-S16, 2011.
Collins et al., "Prospective identification of tumorigenic prostate cancer stem cells." Cancer Research 65: 10946-10951, 2005.
Corbett et al., "Tumor Induction Relationships in Development of Transplantable Cancers of the Colon in Mice for Chemotherapy Assays, with a Note on Carcinogen Structure," Cancer Res 35: 2434-2439, 1975.
Dalerba et al., "Phenotypic characterization of human colorectal cancer stem cells." Proceedings of the National Academy of Sciences 104: 10158-10163, 2007 (Epub Jun. 4, 2007).
Dalerba et al., "Cancer Stem Cells: Models and Concepts," The Annual Review of Medicine, 58:267-284 (2007) (published online Sep. 26, 2006).
Derycke et al., "Nectin 4 Overexpression in Ovarian Cancer Tissues and Serum," Am J Clin Pathol 134: 835-845, 2010.
English translation of the International Search Report for PCT/JP2012/072852, dated Nov. 27, 2012.
Eramo et al., "Identification and expansion of the tumorigenic lung cancer stem cell population." Cell Death & Differentiation 15: 504-514, 2007 (Epub Nov. 30, 2007).
European Search Report for EPC Patent Application No. 10839531.0 (5 pages) (dated Aug. 27, 2014).
Fabre-Lafay et al., "Nectin-4, a New Serological Breast Cancer Marker, is a Substrate for Tumor Necrosis Factor-a-converting Enzyme (TACE)/ADAM-17," J Biol Chem 280(20): 19543-19550, 2005.
Fang et al., "A Tumorigenic Subpopulation with Stem Cell Properties in Melanomas," Cancer Res., vol. 65:9328-9337, 2005.
Fang et al., Expansion of CD133+colon cancer cultures retaining stem cell properties to enable cancer stem cell target discovery, Br. J. Cancer, vol. 102, No. 8, pp. 1265-1275, 2010.
Final Office Action dated Feb. 8, 2016 in U.S. Appl. No. 13/519,059 (14 pages).

(56) References Cited

OTHER PUBLICATIONS

Final Office Action dated Nov. 14, 2018, issued in U.S. Appl. No. 13/519,059 (20 pages).
Final Office Action from U.S. Appl. No. 13/519,059, 11 pages (dated Sep. 19, 2014).
Final Office Action issued in connection with U.S. Appl. No. 14/343,364 dated Oct. 4, 2016 (12 pages).
Fuchs et al., "Irinotecan in the treatment of colorectal cancer," Cancer Treat Rev 32(7):491-503, 2006.
Fujii et al., "Establishment and characterization of in vivo human tumor models in the NOD/SCID/$\gamma_c^{null}$ mouse," Pathology International, 58:559-567 (2008).
Fujii et al., "The potential of the NOD/SCID$\gamma_c^{null}$ mull (NOG) mouse as an in vivo human tissue model," Toxicol Pathol 191-P5 (Jan. 2007).
Fujii et al., Poster Presentations: The 25th Annual Meeting of the Society of Toxicologic Pathology Lawrence, KS, US, Canada (Jun. 18-22, 2006).
Gou et al., "Establishment of Clonal Colony-Forming Assay for Propagation of Pancreatic Cancer Cells With Stem Cell Properties," Pancreas, 34(4):429-435, 2007.
Hamada et al., "Liver metastasis models of colon cancer for evaluation of drug efficacy using NOD/Shi-scid IL2R$\gamma^{null}$ (NOG) mice," Int J Oncol 32(1):153-159, 2008.
Haraguchi et al., "CD133+ CD44+ population efficiently enriches colon cancer initiating cells." Annals of Surgical Oncology 15:2927-2933, 2008 (Epub Jul. 29, 2008).
Hermann et al., "Distinct populations of cancer stem cells determine tumor growth and metastatic activity in human pancreatic cancer," Cell Stem Cell, 1:313-323, (Sep. 13, 2007).
Hirsch et al., "LGR5 positivity defines stem-like cells in colorectal cancer," Carcinogenesis 35(4):849-858, 2014.
Hsu et al., "Characterization of Two LGR Genes Homologous to Gonadotropin and Thyrotropin Receptors with Extracellular Leucine-Rich Repeats and a G Protein-Coupled, Seven-Transmembrane Region." Molecular Endocrinology 12: 1830-1845, 1998.
Hu et al., "ELDA: Extreme Limiting Dilution analysis for comparing depleted and enriched populations in stem cell and other assays," Journal of Immunological Methods, 347: 70-78, 2009.
Huang et al., "ALDH1 is a marker for normal and malignant human colonic stem cells and tracks stem cell overpopulation during colon tumorigenesis." Cancer Res 69: 3382-3389, 2009 (Epub Mar. 31, 2009).
Imada et al., "Serial Transplantation of Adult T Cell Leukemia Cells into Severe Combined Immunodeficient Mice," Jpn. J. Cancer Res. vol. 87, pp. 887-892, 1996.
Inagaki et al., "Long-term maintenance of brain tumor stem cell properties under at non-adherent and adherent culture conditions," Biochem. Biophys. Res. Commun., vol. 361, No. 3, pp. 586-592, 2007.
International Preliminary Report on Patentability (English language translation) for PCT Application No. PCT/JP2012/077714, 13 pages (dated Apr. 29, 2014).
International Preliminary Report on Patentability from PCT Application No. PCT/JP2012/072852 (in English), 11 pages (dated Mar. 12, 2014).
International Search Report for PCT/JP2012/077714, mailed by the ISA (Japanese Patent Office) dated Jan. 29, 2013 (5 pages).
International Search Report on Patentability from PCT/JP2010/073266 (2 pages) (dated Mar. 28, 2011).
InvivoGen, "Immunoglobulin G—Review," http://www.invivogen.com/review-antibody-generation, 2011 (2 pages).
Ishizawa et al., "Tumor-Initiating Cells are Rare in Many Human Tumors," Cell Stem Cell, vol. 7, pp. 279-282, 2010.
Ito et al., "NOD/SCID/$\gamma_c^{null}$ mouse: an excellent recipient mouse model for engraftment of human cells," Blood 100(9):3175-3182, 2002.
Kim et al., "Role of lymphocyte-specific protein tyrosine kinase (LCK) in the expansion of glioma-initiating cells by fractionated radiation," Biochem Biophys Res Commun 402:631-636, 2010.

Kirchner et al., "Patterning a Nuclear β-Catenin Expression in the Colonic Adenoma-Carcinoma Sequence," American Journal of Pathology, 157(4):1113-1121 (2000).
Kobayashi et al., "LGR5-positive colon cancer stem cells interconvert with drug-resistant LGR5-negative cells and are capable of tumor reconstitution," Stem Cells 30:2631-2644 (2012).
Kowalczyk et al., "Molecular and therapeutic characterization of antiectodysplasin A receptor (EDAR) agonist monoclonal antibodies." Journal of Biological Chemistry 286: 30769-30779, 2011.
Ku et al., "Establishment and characterization of 13 human colorectal carcinoma cell lines: mutations of genes and expressions of drug-sensitivity genes and cancer stem cell markers" Carcinogenesis 31(6):1003-1009 (Jun. 2010).
Lapidot et al., "A cell initiating human acute myeloid leukaemia after transplantation into SCID mice." Nature 367: 645-648, 1994.
Li et al., "Identification of pancreatic cancer stem cells." Cancer Research 67: 1030-1037, 2007.
Machida et al., "Higher susceptibility of NOG mice to xenotransplanted tumors," J. Toxicol. Sci. vol. 34, No. 1, pp. 123-127, 2009.
Machine English translation of PCT Publication No. WO 2010/126074, Matsumoto et al., published Nov. 4, 2010.
Machine translation of JP 2008-102012, Hirao et al., published May 1, 2008.
Mani et al., "The epithelial-mesenchymal transition generates cells with properties of stem cells," Cell 133(4):704-715, 2008.
Martin et al., "Expression of the transcription factors snail, slug, and twist and their clinical significance in human breast cancer," Annals of Surgical Oncology, 12(6):488-96, 2005.
McDonald et al., "Identification and cloning of an orphan G protein-coupled receptor of the glycoprotein hormone receptor subfamily." Biochemical and Biophysical Research Communications 247: 266-270, 1998.
Morisot et al., "Leukemia Stem Cells (LSCs) are Frequent in Childhood Precursor B Acute Lymphoblastic Leukemia (ALL)," 50th ASH Annual Meeting and Exposition, Dec. 6, 2008 (2 pages).
Munoz et al., "The Lgr5 Intestinal Stem Cell Signature: Robust Expression of Proposed Quiescent ' + 4' Cell Markers," EMBO J., vol. 31:3079-3091, 2012.
Non-Final Office Action dated Jan. 13, 2014, U.S. Appl. No. 13/519,059, 19 pages.
Non-Final Office Action from U.S. Appl. No. 14/343,364, dated Mar. 7, 2016 (10 pages).
O'Brien et al., "A human colon cancer cell capable of initiating tumour growth immunodeficient mice," Nature, vol. 445, pp. 106-110, 2007.
O'Brien et al., "A human colon cancer cell capable of initiating tumour growth in immunodeficient mice." Nature 445: 106-110, 2007 (Epub Dec. 9, 2008).
Office Action (Restriction Requirement) from U.S. Appl. No. 14/343,364, dated Nov. 12, 2015 (15 pages).
Office Action dated Apr. 27, 2017, issued in connection with U.S. Appl. No. 14/343,364 (13 pages).
Office Action dated Dec. 23, 2019, issued in connection with U.S. Appl. No. 13/519,059 (17 pages).
Office Action dated May 5, 2015 in U.S. Appl. No. 13/519,059.
Office Action dated Oct. 4, 2016, issued in connection with U.S. Appl. No. 14/343,364 (15 pages).
Office Action dated Oct. 5, 2016, issued in connection with U.S. Appl. No. 13/519,059 (13 pages).
Office Action issued in connection with U.S. Appl. No. 13/519,059 dated Jan. 18, 2018 (11 pages).
Office Action issued in connection with U.S. Appl. No. 14/343,364 dated Apr. 27, 2017 (11 pages).
Office Action issued in U.S. Appl. No. 13/519,059, dated Jun. 30, 2020 (24 pages).
Office Action dated Jun. 12, 2017, issued in connection with U.S. Appl. No. 13/519,059 (14 pages).
Oka et al., "Immunohistochemical evaluation of E-cadherin adhesion molecule expression in human gastric cancer," Virchows Archiv A Pathol Anat 421:149-159, 1992.
Pang et al., "A Subpopulation of CD26+ Cancer Stem Cells with Metastatic Capacity in Human Colorectal Cancer." Cell Stem Cell 6: 603-615, 2010.

(56) References Cited

OTHER PUBLICATIONS

Park et al., "Cancer stem cell-directed therapies: recent data from the laboratory and clinic." *Molecular Therapy* 17: 219-230, 2009.
Patrawala et al., "Highly purified CD44+ prostate cancer cells from xenograft human tumors are enriched in tumorigenic and metastatic progenitor cells." *Oncogene* 25: 1696-1708, 2006.
Perego et al., "Heterogeneous Phenotype of Human Melanoma Cells with In Vitro and In Vivo Features of Tumor-Initiating Cells," *J. Invest. Dermatol.*, vol. 130:1877-1886, 2010.
Petrova et al., "Transcription Factor PROX1 Induces Colon Cancer Progression by Promoting the Transition from Benign to Highly Dysplastic Phenotype," *Cancer Cell* 13:407-418, 2008.
Pollard et al., "Glioma Stem Cell Lines Expanded in Adherent Culture Have Tumor-Specific Phenotypes and are Suitable for Chemical and Genetic Screens," *Cell Stem Cell* 4(6):568-580, 2009.
Prince et al., "Identification of a subpopulation of cells with cancer stem cell properties in head and neck squamous cell carcinoma." *Proceedings of the National Academy of Sciences* 104:973-978, 2007.
Quintana et al., "Efficient tumour formation by single human melanoma cells," *Nature*, vol. 456, pp. 593-598, 2008.
Restriction Requirement dated Mar. 20, 2013, U.S. Appl. No. 13/519,059, 11 pages.
Reya et al., "Stem cells, cancer, and cancer stem cells." *Nature* 414: 105-111, 2001.
Ricci-Vitiani et al., "Identification and expansion of human colon-cancer initiating cells." *Nature* 445: 111-115, 2007 (Epub Nov. 19, 2006).
Sato et al., "Single Lgr5 stem cells build crypt villus structures in vitro without a mesenchymal niche." *Nature* 459: 262-265, 2009 (Epub Mar. 29, 2009).
Satpayev et al., "Abstract 2832: Development of AGS-22M6E, a novel antibody drug conjugate (ADC) targeting Nectin-4 for the treatment of solid tumors," *Cancer Res* 71(8 Supplement), Apr. 2011.
Schatton et al., "Identification of cells initiating human melanomas." *Nature* 451: 345-349, 2008.
Singh et al., "Identification of human brain tumour initiating cells." *Nature* 432: 396-401, 2004.
Suemizu et al., "Identification of a key molecular regulator of liver metastasis in human pancreatic carcinoma using a novel quantitative model of metastasis in NOD/SCID/$\gamma_c^{null}$ (NOG) mice," *Int J Oncol* 31:741-751, 2007.
Sun et al., "An ultra-metastatic model of human colon cancer in nude mice," *Clin Exp Metastasis* 17(1): 41-48, 1999.
Takano et al., "Identification of Nectin-4 Oncoprotein as a Diagnostic and Therapeutic Target for Lung Cancer," *Cancer Res* 69(16): 6694-6703, 2009.
Thenappan et al., "New Therapeutics Targeting Colon Cancer Stem Cells," *Curr. Colorectal Cancer Rep.*, vol. 5:209-216, 2009.
Translation of the International Preliminary Report on Patentability, International Application No. PCT/JP2011/073067, dated May 8, 2013.
Vermeulen et al., "Single-cell cloning of colon cancer stem cells reveals a multilineage differentiation capacity," *Proc. Natl. Acad. Sci. USA*, vol. 105, No. 36, pp. 13427-13432, 2008.
Vermeulen et al., "Wnt activity defines colon cancer stem cells and is regulated by the microenvironment," *Nature Cell Biology*, vol. 12, No. 5, pp. 468-476, 2010.
Walker et al., "LGR5 is a Negative Regulator of Tumourigenicity, Antagonizes Wnt Signalling and Regulates Cell Adhesion in Colorectal Cancer Cell Lines," *PLoS One*, vol. 6:e22733, 2011.
Wu et al., "Side population cells isolated from mesenchymal neoplasms have tumor initiating potential." *Cancer Research* 67: 8216-8222, 2007.
Yeung et al., "Cancer stem cells from colorectal cancer-derived cell lines," *Proc. Natl. Acad. Sci. USA*, vol. 107, No. 8, pp. 3722-3727, 2010.
Zahidunnabi et al., "Potential role of NK cells in tumor growth and metastasis of breast cancer cells in NOD/SCID/$\gamma c_{null}$ (NOG) mice: Implication of immune therapy," *Proc. Amer. Assoc. Cancer Res.*, vol. 46, Abstract #4683, 2005 (2 pages).
Zhou et al., "Internalizing Cancer Antibodies from Phage Libraries Selected on Tumor Cells and Yeast-Displayed Tumor Antigens," *J Mol Biol* 404(1):88-99, 2010.
U.S. Appl. No. 17/992,032, filed Nov. 22, 2022, Chugai Seiyaku Kabushiki Kaisha.

\* cited by examiner

PLR123
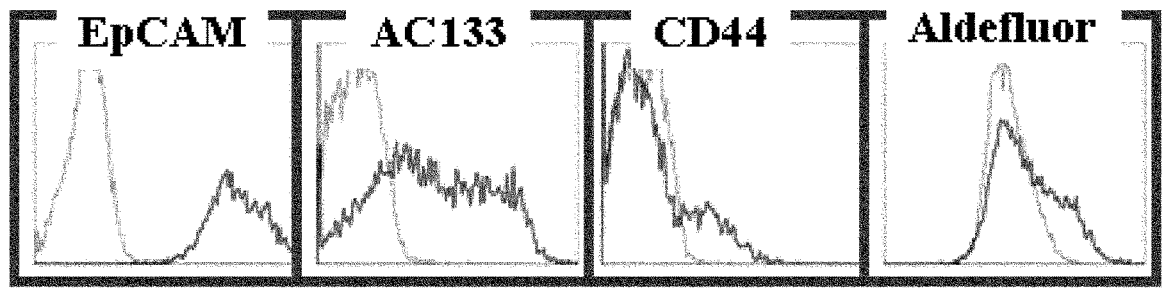
PLR59
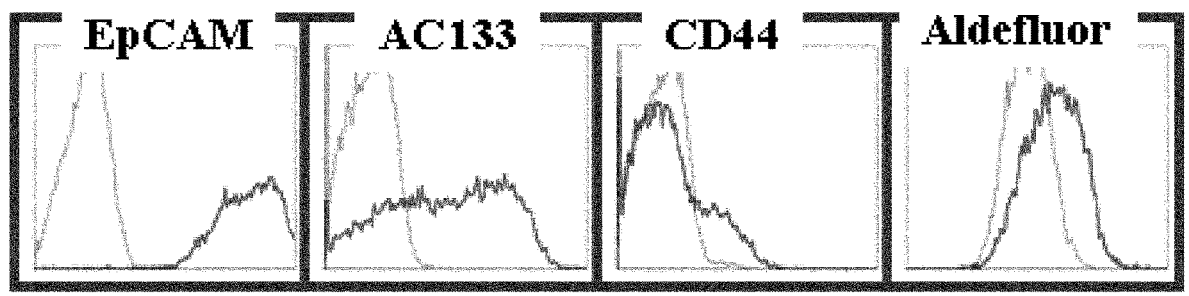
PLR325
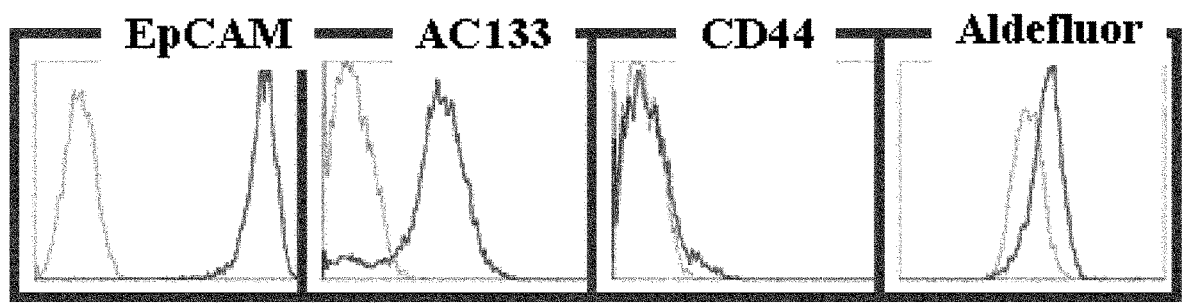
FIG. 2

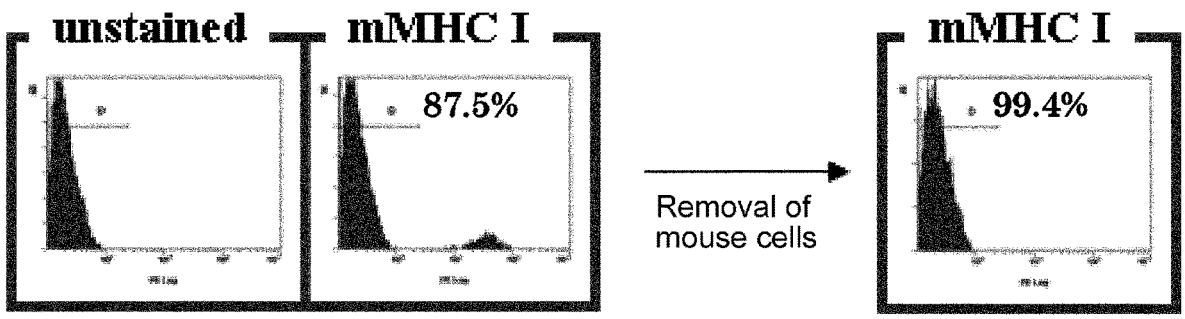
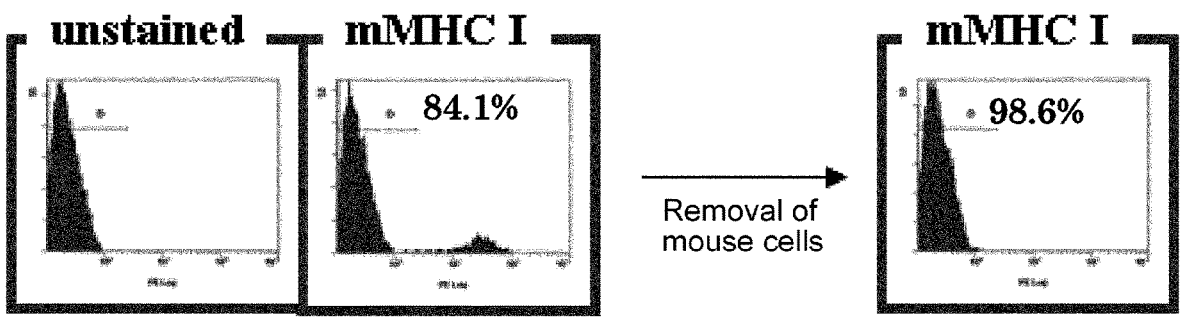
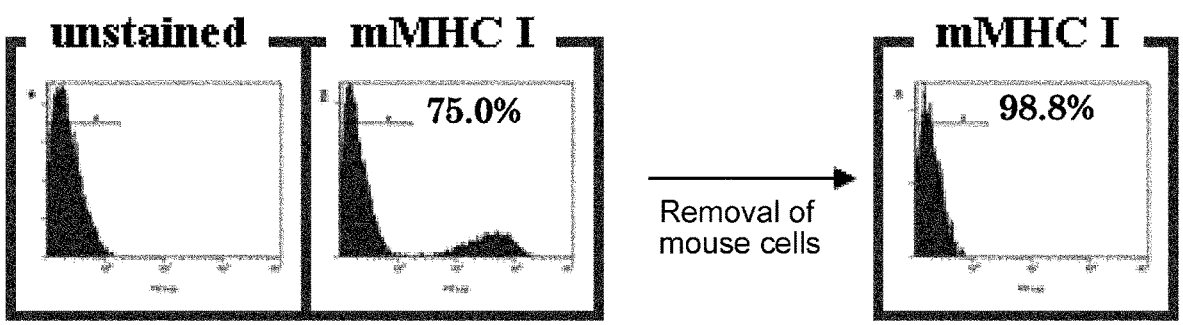
FIG. 3

HCT116
10 cells transplanted

LGR5 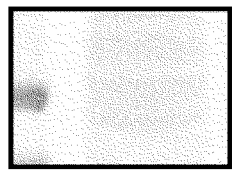
GAPDH 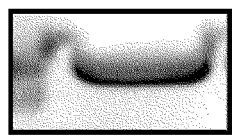
FIG. 8

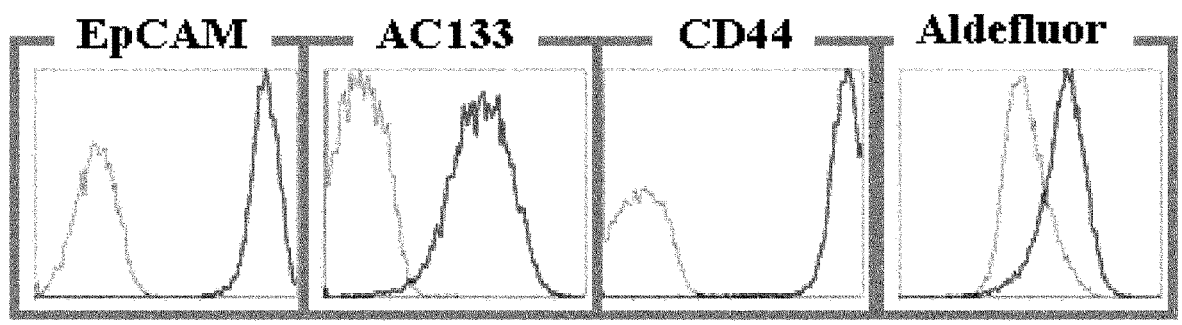
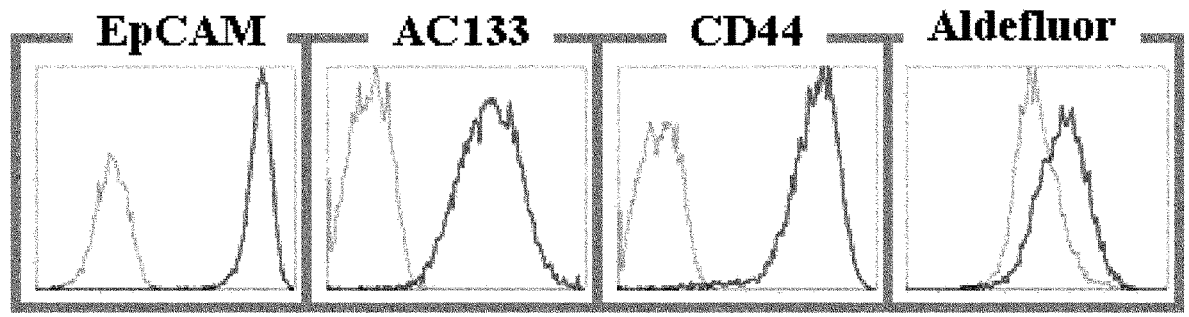
FIG. 11

In vitro PLR123
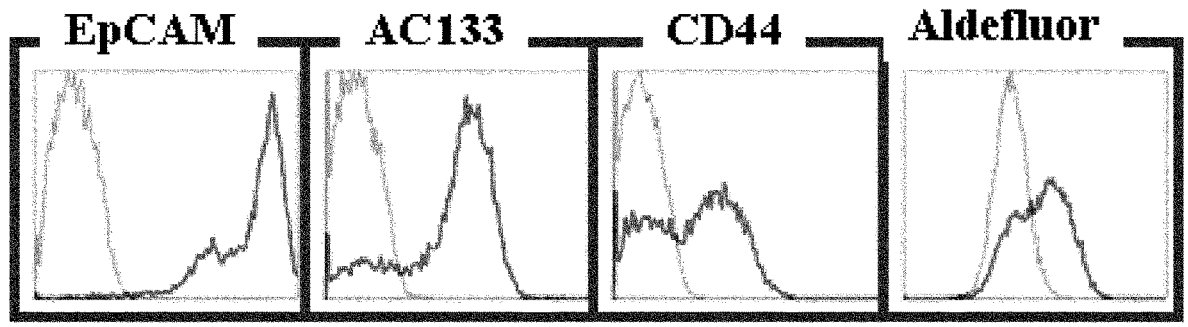
In vitro PLR123 (Cultured for 35 days)
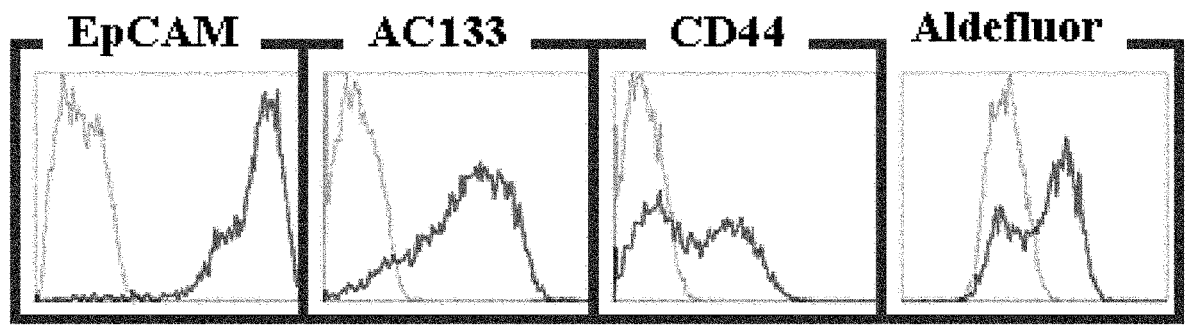
In vitro PLR59
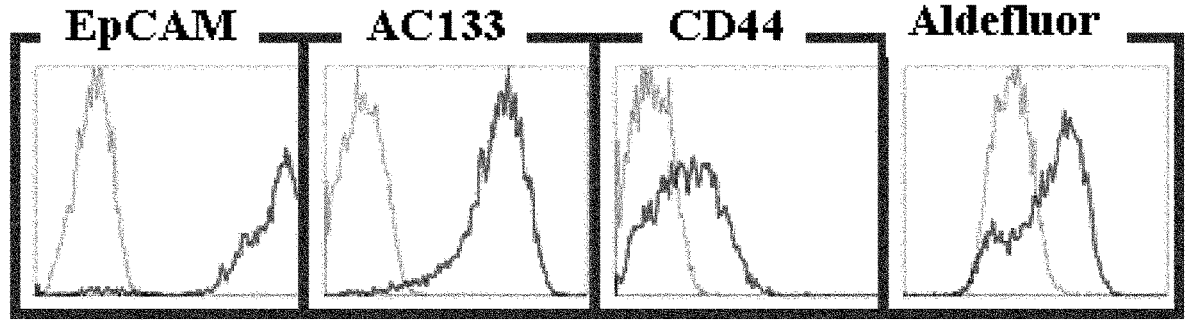
FIG. 15

| Hierarchical structure | Transplanted animals | Type of cancer | Transplanted cells | Frequency of cancer cell mass formation | | Literature |
|---|---|---|---|---|---|---|
| | | | | 100 | 10 | |
| present | NOG | Colon cancer | All cells | 6/6 | 6/6 | The present cancer stem cell population |
| | Nude | Colon cancer | TOP-GFP strongly positive | 2/6 | 3/6 | Nature Cell Biology (2010) 12:5 (468-476) |
| | NOD/SCID | Adenoid cystic carcinoma | ALDH strongly positive | 2/6 | - | BBRC (2010) 396:4 (843-848) |
| | RAG2-/gc- | Bladder cancer | CD44 positive | 1/4 | - | PNAS (2009) 106:33 (14016-14021) |
| | NOD/SCID | Brain tumor | CD133 positive | 2/2 | - | Nature (2004) 432:7015 (396-401) |
| | NOD/SCID | Colon cancer | CD133 positive | 1/4 | - | Nature (2007) 445:7123 (106-110) |
| | NOD/SCID | Ovarian cancer | All cells | 1/3 | - | Stem Cells (2009) 27:12 (2875-2883) |
| | NOD/SCID | Pancreatic cancer | CD44 positive, CD24 positive, ESA positive | 6/12 | - | Cancer Res (2007) 67:3 (1030-1037) |
| | NOD/SCID | Pancreatic cancer | CD44 positive, CD24 positive | 3/4 | - | Cell Stem Cell (2010) 3:7(3) (279-82) |
| absent | RAG2-/gc- | Melanoma | All cells | - | 3/3 | Nature (2010) 466:7302 (133-137) |
| | NOD-SCID Il2rg(-/-) | Melanoma | All cells | - | 6/6 | Nature (2008) 456:7222 (593-598) |
| | NOD-SCID | Lung cancer | All cells | 4/4 | 6/6 | Cell Stem Cell (2010) 3:7(3) (279-82) |
| | SCID | Colon cancer | CD44 strongly positive | 4/5 | 5/5 | Int J Cancer (2009) 124:6 (1312-1321) |
| | NOD/SCID | Prostate cancer | CD44 positive | 10/10 | 1/4 | Oncogene (2006) 25:12 (1696-1708) |
| | SCID | Melanoma | Spheroid | 3/3 | - | J Invest Dermatol (2010) 130:7 (1877-1886) |
| | Nude | Melanoma | Spheroid | 2/2 | - | Tumor Biol (2009) 30:5-6 (300-309) |
| | NOD/SCID | Mesenchymal tumor | Side population cells | 9/14 | - | Cancer Res (2007) 67:17 (8216-8222) |
| | NOD/SCID | Prostate cancer | All cells | 1/8 | - | Cancer Res (2008) 68:6 (1820-1825) |
| | NOD/SCID | Prostate cancer | CD45 positive | 5/5 | - | Br J Cancer (2008) 98:4 (756-765) |
| | | | | | -: Not performed | |

FIG. 17

| Cell line | Number of cells per inoculation site | | |
|---|---|---|---|
| | 1,000 | 100 | 10 |
| PLR59 | 6/6 | 6/6 | 6/6 |
| PLR123 | 6/6 | 6/6 | 6/6 |

FIG. 23

PLR123
| Floating to adherent | Adherent to floating |
|---|---|
| 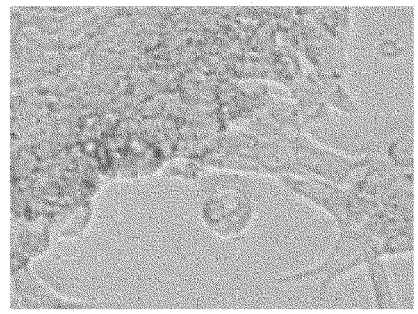 | 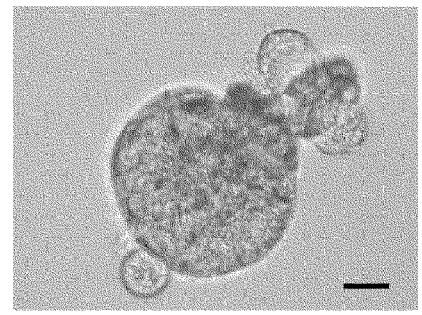 |
Scale bar : 10 μm
FIG. 35

| Organ | Incidence of tumor formation |
|---|---|
| Lung | 5/5 |
| Liver | 4/5 |
| Kidney | 1/5 |
| Brain, pia mater | 1/5 |
| Lymph node, armpit | 2/5 |
| Subcutaneous tissue | 5/5 |

FIG. 40

CANCER STEM CELL POPULATION AND METHOD FOR PRODUCTION THEREOF

CROSS REFERENCE TO RELATED APPLICATIONS

This is a divisional of U.S. application Ser. No. 13/878,181, filed Jul. 5, 2013, which is the U.S. National Stage of International Application No. PCT/JP2011/073067, filed Oct. 6, 2011, which in turn claims the benefit of JP Application No. 2010-226301, filed Oct. 6, 2010. The above-listed applications are incorporated herein in their entirety.

SEQUENCE LISTING

The Sequence Listing is submitted as an ASCII text file, created on Aug. 13, 2020, 1.61 KB, which is incorporated by reference herein.

TECHNICAL FIELD

The present invention relates to a cancer stem cell population having a feature of reproducing the hierarchical structure of cancer tissue, wherein cells having no cancer-forming ability are substantially removed, and a production method thereof. The present invention also relates to a method of searching for drug target molecules, a method of assessing drugs, and a method of screening for drugs, using a non-human animal model transplanted with the cancer stem cell population or a culture system of the cancer stem cell population under in vitro conditions.

BACKGROUND ART

Conventionally, it is considered that in cancer with a hierarchical structure, cancer cells at various differentiation stages self-replicate to form a large tumor mass. However, recently, cancer was found to form from restricted cancer cells that have both self-replicating ability and pluripotency at an early differentiation stage. This is referred to as a cancer stem cell model. The presence of cancer stem cells has been reported in various cancers such as blood, brain, breast, and colon cancers. It has been proposed that in the cancer stem cell model, cancer is constituted from heterogeneously differentiated populations, and only a limited type of cells, i.e., cancer stem cells, can form new cancer.

Cancer-forming cells such as CML and blood cancer, or poorly differentiated epithelial cancer, which are constituted of monoclonal cell populations without a hierarchical structure, may also be referred to as cancer stem cells. These cells have a self-replicating ability, but no hierarchical structure-forming ability (pluripotency). These cells deviate from the above cancer stem cell model, thus making the definition of cancer stem cell confusing. For example, in 2008, Quintana et al. reported that almost all human melanoma cells could form tumors in an experiment using severely immunodeficient mice lacking B-, T-, and NK-cells (Non-patent Document 1). However, these cells should not be included in the cancer stem cell because they lack pluripotency and do not differentiate, and therefore should be simply referred to as cancer-forming cells.

Cancer stem cells that form a hierarchical structure have been isolated and concentrated by flow cytometry using cancer stem cell markers such as CD133 and CD44, or by performing a floating culture method using cancer cells and a stem cell medium containing FGF and EGF. Flow cytometry has problems as a method of preparing high-purity intact cancer stem cells, because it damages cells during the procedure, and also CD133 and CD44 that are used as cancer stem cell markers are not cancer stem cell-specific surface markers. Actually, it was demonstrated in a cancer stem cell population collected by flow cytometry from cancer with a hierarchical structure, when the cancer-forming ability was evaluated using limiting dilution, the frequency of cancer stem cells was about 1/262, and it contained many cells besides cancer stem cells (Non-patent Document 2).

In addition, it was reported that a spheroid (cell mass) formed from floating culture contains cancer stem cells that form cancer having a hierarchical structure. The cell population that constitutes the spheroid was a non-homogeneous population. It contained large quantities of cells besides cancer stem cells, and the frequency of cancer stem cells was about 1/240 (Non-patent Document 3). Thus, due to the low purity of cancer stem cells, it is difficult to elucidate the properties of cancer stem cells with a hierarchical structure using these cell populations. In addition, a method has been reported for concentrating cancer stem cells by transplanting a human cancer tissue into an immunodeficient animal followed by repeated passage (Non-patent Document 4). The frequency of most concentrated cancer stem cells by this method was about 1/180 for pancreatic cancer.

In addition, it was reported that p75NTR-positive cells isolated using p75NTR, a stem cell marker, from a cell line immortalized by introducing a human papillomavirus oncogene into human cervical epithelial cells were adherently cultured in a medium containing TGFβ and TNFα (Patent Document 1). These cells do not form a hierarchical structure, and therefore do not fall into the category of cancer stem cells.

So far there is no known method for preparing high-purity cancer stem cells that form a hierarchical structure in large quantities, and thus there is a strong demand for its development.

PRIOR ART DOCUMENTS

Patent Documents

[Patent Document 1] Japanese Patent Application Kokai Publication no. (JP-A) 2008-182912

Non-Patent Documents

[Non-patent Document 1] Quintana E. et al., Nature. 2008 Dec. 4; 456(7222): 593-8
[Non-patent Document 2] O'Brien C A. et al., Nature. 2007 Jan. 4; 445(7123): 106-10
[Non-patent Document 3] Vermeulen L. et al., Nat Cell Biol. 2010 May; 12(5): 468-76
[Non-patent Document 4] Ishizawa K. et al., Cell Stem Cell. 2010 Sep. 3; 7(3): 279-82

DISCLOSURE OF THE INVENTION

Problems to be Solved by the Invention

An objective of the present invention is to provide a population of cancer stem cells from which cells having no cancer-forming ability have been substantially removed, wherein the population has a feature of reproducing the cancer-tissue hierarchical structure. In addition, another objective of the present invention is to provide a method for producing a population of cancer stem cells from which cells having no cancer-forming ability have been substantially removed, which comprises the step of adherently culturing a cell group containing cancer stem cells. Furthermore, another objective of the present invention is to provide a method of searching for drug target molecules, a method for assessing drugs, and a method for screening for drugs, using a non-human animal model transplanted with the cancer stem cell population or a culture system of the cancer stem cell population under in vitro conditions.

Means for Solving the Problems

To solve the above problems, the present inventors conducted extensive studies.

The inventors established a cancer cell line in severely immunodeficient mice to compare and analyze cancers with or without a hierarchical structure using the established cell line. In addition, due to the lack of methods for isolating, concentrating, homogenizing, and mass-culturing cancer stem cells for cancer with a hierarchical structure that belongs to the cancer stem cell model, analysis and drug screening using cancer stem cells is compromised, and the inventors attempted to solve these problems.

The inventors transplanted a human cancer tissue into NOD/SCID/gamma$_c^{null}$ mice which have no functional T, B, and natural killer cells (Fujii E. et al., Pathol Int. 2008; 58: 559-567) (hereinafter, these mice and NSG mice (NOD-scid, IL-2Rg$^{null}$ mice) are referred to as "NOG mouse" in the present application) to establish several human cancer cell lines. These lines can form cancer tissue with the same morphology as that of the original cancer tissue even after repeated subcutaneous passage in NOG mice, suggesting that human cancer stem cells can be stored in the cell population. Thus, human cancer stem cells that can be passaged in NOG mice are a very useful research tool.

The inventors repeatedly grew human cancer tissues in NOG mice, and then isolated cancer cells for comparing various culture methods. As a result, the present invention is completed by successfully obtaining a homogeneous cancer stem cell composition in which cells having cancer-forming ability and cells without cancer-forming ability does not substantially coexist by an adherent culture method using a serum-free stem cell medium, rather than by a routine floating culture method.

Cancer stem cells obtained by this method were stably maintained for over a month without phenotypic change by repeated passage of the adherent culture using a serum-free stem cell medium. These cells expressed various colon cancer stem cell markers (CD133, CD44, EpCAM, CD166, CD24, CD26, and CD29) reported previously, as well as demonstrated cancer-forming ability with a nearly 100% frequency, and reconstructed tumor with the same histopathological properties (hierarchical structure) as those of original primary tumor. These cells are characterized as being highly proliferative under adherent culture conditions and positive for the cell surface marker Lgr5. In addition, when injected into the mouse tail vein, Lgr5-positive cancer stem cells with a high proliferating ability formed tumor masses in organs such as lungs and liver, suggesting that they play an important role in cancer metastasis.

Lowly proliferative, Lgr5-negative cancer stem cells could be isolated by culturing cancer stem cells that demonstrate high proliferation under adherent culture conditions and which are positive for the cell surface marker Lgr5 in suspension, or treating them with anticancer agents such as irinotecan and 5-FU. These cells also showed a high cancer-forming ability. Furthermore, it was demonstrated that lowly proliferative, Lgr5-negative cancer stem cells transform into highly proliferative, Lgr5-positive cancer stem cells by isolation and culturing again under adherent culture conditions. Thus, highly proliferative, Lgr5-positive cancer stem cells and lowly-proliferative, Lgr5-negative cancer stem cells are mutually inter-convertible, and have self-transforming ability.

More specifically, the present invention provides [1] to [33] below:

[1] a population of cancer stem cells from which cells with no cancer-forming ability have been substantially removed, wherein the population is characterized by reproducing the hierarchical structure of a cancer tissue;

[2] the cancer stem cell population of [1], wherein the cancer stem cells are derived from a human tumor tissue;

[3] the cancer stem cell population of [2], wherein the human tumor tissue is derived from epithelial cancer;

[4] the cancer stem cell population of [3], wherein the epithelial cancer is pancreatic cancer, prostate cancer, breast cancer, skin cancer, gastrointestinal cancer, lung cancer, hepatocellular carcinoma, cervical cancer, endometrial cancer, ovarian cancer, fallopian tube cancer, vaginal cancer, liver cancer, bile duct cancer, bladder cancer, urinary tract cancer, thyroid cancer, adrenal cancer, kidney cancer, or other glandular tissue cancer;

[5] the cancer stem cell population of any one of [1] to [4], which is substantially homogeneous;

[6] the cancer stem cell population of any one of [1] to [5], wherein the frequency of cancer stem cells in extreme limiting dilution analysis is 1/20 or higher;

[7] the cancer stem cell population of any one of [1] to [6], which comprises $1 \times 10^4$ or more cancer stem cells;

[8] the cancer stem cell population of any one of [1] to [7], which is produced by a method comprising the step of adherently culturing a cell group containing cancer stem cells;

[9] the cancer stem cell population of any one of [1] to [8], which is produced by a method comprising the steps of:
(1) transplanting a cell group containing cancer stem cells into a non-human animal that belongs to the same or different species to produce a cancer cell mass;
(2) fragmenting the produced cancer cell mass; and
(3) adherently culturing the cell population obtained in step (2) in a stem cell medium;

[10] the cancer stem cell population of any one of [1] to [9], wherein the non-human animal is a nude mouse, a SCID mouse, a NOD-SCID mouse, a NOG mouse, or a nude rat;

[11] a method of producing a population of cancer stem cells from which cells with no cancer-forming ability have been substantially removed, wherein the method comprises adherently culturing a cell group containing cancer stem cells;

[12] the method of [11], wherein the cell group containing cancer stem cells reproduces the hierarchical structure of a cancer tissue;

[13] the method of [12], wherein the cell group that reproduces the hierarchical structure of a cancer tissue is a cancer cell line established in a non-human animal, spheroid, or cells positive for at least one or more cancer stem cell markers selected from CD24, CD29, CD34, CD44, CD49f, CD56, CD90, CD117, CD133, CD135, CD166, CD184, CD271, CD326, Aldefluor, ABCG2, ABCG5, LGR5, and Msi1;

[14] the method of any one of [11] to [13], wherein the cell group containing cancer stem cells is allowed to proliferate before performing adherent culture;

[15] the method of [14], wherein the cell group containing cancer stem cells is allowed to proliferate by spheroid culture;
[16] the method of [14], wherein the cell group is proliferated by being transplanted to and passaged in a non-human animal;
[17] the method of any one of [11] to [16], wherein the cancer stem cells are derived from a human tumor tissue;
[18] the method of [17], wherein the human tumor tissue is derived from epithelial cancer;
[19] the method of [18], wherein the epithelial cancer is pancreatic cancer, prostate cancer, breast cancer, skin cancer, gastrointestinal cancer, lung cancer, hepatocellular carcinoma, cervical cancer, endometrial cancer, ovarian cancer, fallopian tube cancer, vaginal cancer, liver cancer, bile duct cancer, bladder cancer, urinary tract cancer, thyroid cancer, adrenal cancer, kidney cancer, or other glandular tissue cancer;
[20] the method of any one of [11] to [19], wherein the non-human animal is a nude mouse, a SCID mouse, a NOD-SCID mouse, a NOG mouse, or a nude rat;
[21] a method of searching for a target molecule of a drug, wherein assessment is performed in a non-human animal model transplanted with the cancer stem cell population of any one of [1] to [10], or in a culture system of the cancer stem cell population under in vitro conditions, by using as an index a hierarchical structure formed from cancer stem cells, a cancer development process originating from cancer stem cells, or a biological property of cancer stem cells;
[22] the method of [21], wherein the method comprises the steps of:
(1) producing a non-human animal model by transplanting the cancer stem cell population of any one of [1] to [10] to a non-human animal;
(2) collecting a tissue section showing a tissue structure characteristic of a cancer development process of said cancer stem cell population or showing a biological property thereof,
(3) examining the tissue section collected in (2) for the expression of a DNA, RNA, protein, peptide, or metabolite; and
(4) identifying a DNA, RNA, protein, peptide or metabolite that varies depending on a hierarchical structure formed from the cancer stem cells, a cancer development process originating from the cancer stem cells, or a biological property of the cancer stem cells, in the tissue section;
[23] the method of [21], wherein the method comprises the steps of:
(1) culturing the cancer stem cell population of any one of [1] to [10] under in vitro conditions to reproduce a characteristic structure of a cancer development process originating from cancer stem cells, or a biological property of cancer stem cells;
(2) examining the expression of a DNA, RNA, protein, peptide or metabolite in cultured cells with the reproduced characteristic structure; and
(3) identifying a DNA, RNA, protein, peptide or metabolite that varies depending on a hierarchical structure formed from the cancer stem cells, a cancer development process originating from the cancer stem cells, and a biological property of the cancer stem cells, in the cultured cells;
[24] the method of any one of [21] to [23], wherein the drug is an anticancer agent;
[25] the method of any one of [21] to [24], wherein the target molecule is a cancer cell marker;
[26] a method of assessing a drug, wherein assessment is performed in a non-human animal model transplanted with the cancer stem cell population of any one of [1] to [10], or in a culture system of the cancer stem cell population under in vitro conditions, by using as an index a hierarchical structure formed from cancer stem cells, a cancer development process originating from cancer stem cells, or a biological property of cancer stem cells;
[27] the method of [26], wherein the method comprises the steps of:
(1) producing a non-human animal model by transplanting the cancer stem cell population of any one of [1] to [10] to a non-human animal;
(2) administering a test substance to the non-human animal model of (1);
(3) collecting a tissue section showing a tissue structure characteristic of a cancer development process originating from cancer stem cells or showing a biological property thereof;
(4) observing a change in the cancer stem cells over time, cancer development process, or a biological property thereof, in the tissue section; and
(5) identifying formation of a hierarchical structure formed from the cancer stem cells, a cancer development process originating from the cancer stem cells, or a biological property of the cancer stem cells, that is inhibited by the test substance;
[28] the method of [26], wherein the method comprises the steps of:
(1) culturing the cancer stem cell population of any one of [1] to [10] under in vitro conditions to reproduce a characteristic structure of a cancer development process originating from cancer stem cells or a biological property of cancer stem cells;
(2) treating the cultured cells of (1) with a test substance;
(3) observing changes in a hierarchical structure formed from the cancer stem cells, a cancer development process originating from the cancer stem cells, or a biological property of the cancer stem cells; and
(4) identifying a hierarchical structure formed from the cancer stem cells, a cancer development process originating from the cancer stem cells, or a biological property of the cancer stem cells, that is inhibited by the test substance;
[29] a method of screening for a drug, wherein assessment is performed in a non-human animal model transplanted with the cancer stem cell population of any one of [1] to [10], or in a culture system of the cancer stem cell population under in vitro conditions, by using as an index a hierarchical structure formed from cancer stem cells, a cancer development process originating from cancer stem cells, or a biological property of cancer stem cells;
[30] the method of [29], wherein the method comprises the steps of:
(1) producing a non-human animal model by transplanting the cancer stem cell population of any one of [1] to [10] to a non-human animal;
(2) administering a test substance to the non-human animal model of (1);
(3) collecting a tissue section that shows a tissue structure characteristic of a cancer development process originating from cancer stem cells, or shows a biological property thereof;
(4) observing a change in the cancer stem cells over time, cancer development process, or a biological property thereof, in the tissue section; and
(5) identifying a test substance that inhibits formation of a hierarchical structure formed from specific cancer stem cells, a cancer development process originating from cancer stem cells, or a biological property of cancer stem cells;

[31] the method of [29], wherein the method comprises the steps of:
(1) culturing the cancer stem cell population of any one of [1] to [10] under in vitro conditions to reproduce a characteristic structure of a cancer development process originating from cancer stem cells or a biological property of cancer stem cells;
(2) treating the cultured cells of (1) with a test substance;
(3) observing a change in a hierarchical structure formed from cancer stem cells, a cancer development process originating from cancer stem cells, or a biological property of cancer stem cells; and
(4) identifying a test substance that inhibits formation of a hierarchical structure formed from specific cancer stem cells, a cancer development process originating from cancer stem cells, or a biological property of cancer stem cells;
[32] the method of any one of [26] to [31], wherein the drug is an anticancer agent; and
[33] the method of any one of [21], [23], [26], [28], [29], and [31], wherein the culture system under in vitro conditions is spheroid culture.

BRIEF DESCRIPTION OF THE DRAWINGS

FIG. 2 shows results of the flow cytometric analysis using cancer stem cell markers for cells that are negative for both mouse MHC class I and the 7-AAD Viability Dye by EPICS ALTRA. Cancer stem cell marker-positive cells were observed in cancer cell masses formed from colon cancer lines PLR123, PLR59, and PLR325. Moderately differentiated colon cancer lines, PLR123 and PLR59, generated a mixture of marker-positive and -negative cells, i.e., a heterogeneous cell population. A poorly differentiated colon cancer line, PLR325, generated cells that were all positive for EpCAM, AC133, and Aldefluor and all negative for CD44, i.e., a homogeneous cell population.

FIG. 3 shows results of the flow cytometric analysis using EPICS ALTRA for cells from which mouse cells have been removed. In cancer cell masses formed from colon cancer lines PLR123, PLR59, and PLR325, 95% or more of the cells were negative for mouse MHC class I after the removal of mouse cells.

FIG. 8 shows LGR5 protein expression by Western blotting. No LGR5 protein was detected in the commercially available colon cancer line HCT116.

FIG. 11 shows results of the flow cytometric analysis using cancer stem cell markers for 7-AAD Viability Dye-negative cells by EPICS ALTRA. The moderately differentiated colon cancer lines PLR123 and PLR59 that were adherently cultured in vitro were all positive for the cancer stem cell markers, suggesting homogeneous cell populations.

FIG. 15 shows results of the flow cytometric analysis of cells negative for both mouse MHC class I and the 7-AAD Viability Dye by EPICS ALTRA using cancer stem cell markers. In cancer cell masses formed from 10 cells of the moderately differentiated colon cancer lines PLR123 and PLR59 adherently cultured in vitro, cancer stem cell marker-negative cells were observed, suggesting that differentiated cells without cancer-forming ability were generated from cancer stem cells.

FIG. 17 presents a table that shows the frequency of cancer cell mass formation by 100 or less cells in the cancer stem cell populations of the present invention and in literature. Cancer formation and hierarchical structure were observed in all transplantations of the cancer stem cell populations.

FIG. 23 shows flow cytometric analysis (FIG. 22) of adherent cancer stem cells derived from PLR59 and PLR123 xenografts after being cultured for one month, and their injection into NOG mice. The number of adherent cancer stem cells shown in the drawing was injected subcutaneously into the flanks of NOG mice to examine tumorigenic activity in the NOG mice. This drawing shows results of tumorigenesis determined at 47 days post-inoculation. Even a subcutaneous injection of 10 adherent cancer stem cells caused tumor formation at all the injection sites. The histopathological morphology of the tumors was highly similar to that of the original tumor.

FIG. 35 presents a photograph showing alternate changes of the cancer stem cell morphology. Lgr5-negative colon cancer stem cells were dissociated and cultured in a flat-bottom plate. Some cells adhered to the plate bottom and became positive for Lgr5, showing a mesenchymal cell-like morphology (left). Lgr5-positive adherent colon cancer stem cells were cultured in an ultra-low attachment plate. Some cells stopped growing and formed a spheroid-like structure. The scale bar indicates 10 μm.

FIG. 40 shows the tumorigenic activity of adherent cancer stem cells in various organs. $5 \times 10^5$ adherent cancer stem cells of PLR123 cells were injected into the tail vein (n=5). The incidence rates of tumor formation in various organs on day 40 post-administration are shown.

BEST MODE FOR CARRYING OUT THE INVENTION

Figure 1:
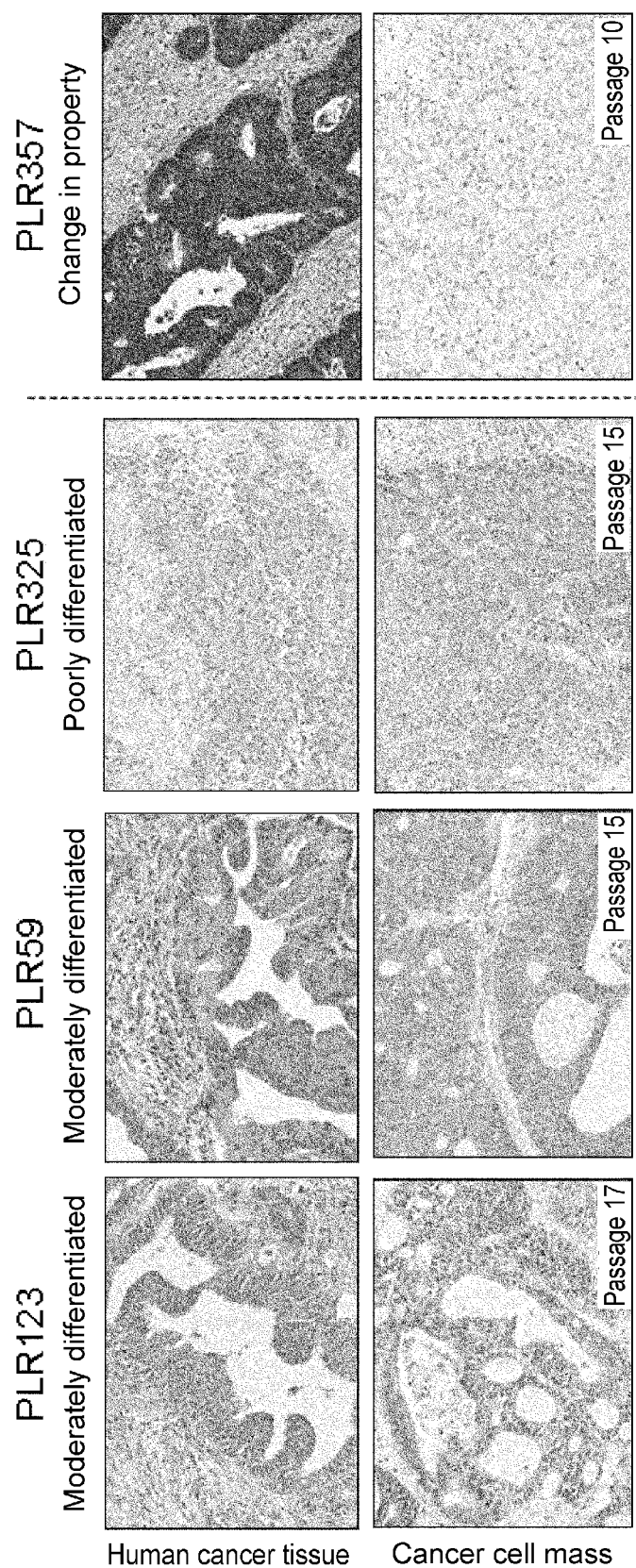
FIG. 1 presents a photograph showing an HE-stained tissue specimen. Colon cancer lines, PLR123, PLR59, and PLR325, that had been transplanted into mice showed morphological structures similar to those observed in human tissues, suggesting there was no mouse influence. On the other hand, the colon cancer line PLR357 that had been transplanted into NOG mice showed morphological changes, suggesting that it is not suitable for mouse transplantation experiments.

The present invention relates to a population of cancer stem cells which can be effectively used in the development of drugs for the treatment or prevention of human cancer diseases. Specifically, the present invention relates to a population of cancer stem cells from which cells having no cancer-forming ability have been substantially removed, wherein the population characterized by reproducing the hierarchical structure of a cancer tissue.

The origin of the cancer stem cell population of the present invention is not particularly limited, but is preferably a human tumor tissue.

A first aspect of the present invention provides a population of cancer stem cells from which cells having no cancer-forming ability have been substantially removed, wherein the population reproduces the hierarchical structure of a cancer tissue.

In the present invention, "cancer" typically refers to a physiological condition in mammals characterized by uncontrolled cell proliferation, or to a related physiological condition. The types of cancer in the present invention include, but are not limited to, carcinomas (epithelial cancers), such as pancreatic cancer, prostate cancer, breast cancer, skin cancer, gastrointestinal cancer, lung cancer, hepatocellular carcinoma, cervical cancer, endometrial cancer, ovarian cancer, fallopian tube cancer, vaginal cancer, liver cancer, bile duct cancer, bladder cancer, urinary tract cancer, thyroid cancer, adrenal cancer, kidney cancer, and other glandular tissue cancers. Sarcomas (non-epithelial carcinomas) include liposarcoma, leiomyosarcoma, rhabdomyosarcoma, synovial sarcoma, angiosarcoma, fibrosarcoma, malignant peripheral nerve tumor, gastrointestinal stromal tumor, desmoid tumor, Ewing's sarcoma, osteosarcoma, chondrosarcoma, leukemia, lymphoma, myeloma, and other solid organ tumors, e.g., melanoma or brain tumor (Kumar V, Abbas A K, Fausio N. Robbins and Cotran Pathologic Basis of Disease. 7th Ed. Unit I: General Pathology, 7: Neoplasia, Biology of tumor growth: Benign and malignant neoplasms. 269-342, 2005). The cancer stem cell population of the present invention may be derived from tumor tissues derived from the above epithelial cancers.

In the present invention, "cancer stem cells" refer to cells having the abilities of i) and/or ii) below.
i) Self-replicating ability. Self-replicating ability refers to the ability of one or both of two divided daughter cells to produce cells that retain abilities and degree of differentiation equivalent to those of the parent cells according to the cell lineage.
ii) Ability of differentiating into multiple types of cancer cells that constitute a cancer cell mass. As with normal stem cells, multiple types of cancer cells differentiated from a cancer stem cell form a hierarchical structure in which the cancer stem cell is at the apex according to the cell lineage. The stepwise production of various types of cancer cells from a cancer stem cell leads to formation of a cancer cell mass having various properties.

Cancer stem cells are cancer cells that have cancer-forming ability and possess pluripotency and self-replicating ability like normal stem cells. In addition, they may be positive for at least one or more cancer stem cell markers selected from CD24, CD29, CD34, CD44, CD49f, CD56, CD90, CD117, CD133, CD135, CD166, CD184, CD271, CD326, Aldefluor, ABCG2, ABCG5, LGR5, and Msi1, but are not necessarily required to be positive for these markers. Preferably, at least one or more markers selected from CD326, CD133, CD44, and ALDH are positive. More preferably, at least two or more markers selected from CD326, CD133, CD44, and ALDH are positive. Even more preferably, at least three or more markers selected from CD326, CD133, CD44, and ALDH are positive. Most preferably, all of CD326, CD133, CD44, and ALDH are positive.

In addition, the ability of epithelial-mesenchymal transition, which is a biological activity that can be exhibited by cancer stem cells, may be one of the properties of cancer stem cells. Normal and tumor cells are present in various differentiation states in vitro and in vivo. These differentiation states are regulated at least in part through the integration of complex signals arising from tissue microenvironment to which the cells belong. Cells (e.g., cancer cells) may be led to undergo epithelial-mesenchymal transition (EMT) through many genetic perturbations, for example, through the overexpression of specific factors (e.g., Twist, Snail, TGF-β, or MMPs) or inhibition of adhesion junction proteins such as E-cadherin. Regardless of what method is used, cells which are led to EMT express similar phenotypic traits and marker proteins (e.g., biomarkers), suggesting that the EMT is a major differentiation program. The present invention relates to a discovery that cells which are led to EMT share many of the properties of cancer stem cell, including expression of cell surface markers associated with cancer stem cells, growth in suspension culture, tumor formation in vivo from a small number of cells, and resistance to specific standard chemotherapeutic agents. Thus, the state of cell differentiation as shown by cells that underwent epithelial-mesenchymal transition, which is also referred to as mesenchymal or epithelial-mesenchymal transdifferentiation, can be employed to identify a treatment that specifically targets cancer stem cells. In one non-limiting embodiment of the present invention, there is provided a method of inducing epithelial-mesenchymal transition in order to, for example, generate test cells.

Cancer stem cells form a hierarchical structure in which the cancer stem cell is at the apex. The stepwise production of various types of cancer cells from a cancer stem cell leads to formation of a cancer cell mass having various characteristics. On the other hand, cancer-forming cells are cancer cells having no pluripotency and having cancer-forming ability. A cancer formation test allows evaluation of cancer-forming and self-replicating abilities. Pathological analyses and analyses using differentiation markers allow evaluation of pluripotency. To demonstrate being a cancer stem cell, not only cancer-forming ability but also self-replicating ability and pluripotency should be evaluated.

A cancer cell mass is a mass formed by cells etc. that are not separated but adhered to one another like human tumor tissues, and refers to a mass constructed with cancer cells, cells other than cancer cells such as stromal and blood cells, and extracellular matrices such as collagen and laminin.

The hierarchical structure refers to a part of the unique structure characteristic of a normal tissue that is histopathologically detected in the structures of a tumor originating from the normal tissue. In general, this hierarchical structure is highly reproduced in highly-differentiated cancer. For example, the formation of lumens, occurrence of mucous cells, and the like are seen in tumors of glandular lumen-forming organs (e.g., stomach cancer, colon cancer, pancreatic cancer, liver cancer, bile duct cancer, breast cancer, lung adenocarcinoma, and prostate cancer). The formation of epithelial multilayer structure and keratinization are seen in tumors with a squamous cell structure (squamous cell carcinomas of the lungs, skin, and vaginal mucosa). Lowly differentiated cancers insufficiently reproduce the hierarchical structure and are highly atypical (Kumar V, Abbas A K., Fausio N. Robbins and Cotran Pathologic Basis of Disease. 7th Ed. Unit I: General Pathology, 7: Neoplasia, Biology of tumor growth: Benign and malignant neoplasms. 272-281, 2005). Since this hierarchical structure may be reproduced as a result of various biological reactions of cancer, a non-human animal model to reproduce this hierarchical structure is highly valuable.

"Reproducing a hierarchical structure" means that a unique structure characteristic of a cancer tissue is similarly observed when transplanted from a donor cancer patient to a non-human animal.

"Having cancer-forming ability" means that cells or a cell population transplanted to a non-human animal forms a cancer cell mass, preferably, a cancer cell mass having a hierarchical structure.

"Having no cancer-forming ability" means that cells or a cell population transplanted to a non-human animal cannot form a cancer cell mass.

Substantial removal of cells having no cancer-forming ability can be confirmed by transplanting to an immunodeficient animal a cell population that has been subjected to limiting dilution. In the present invention, the phrase "cells having no cancer-forming ability have been substantially removed" means that the frequency of formation of a cancer cell mass formed when subcutaneously transplanting 10 cells per spot in an immunodeficient animal, preferably an NOG mouse, is 60% or higher, preferably 70% or higher, more preferably 80% or higher, even more preferably 90% or higher, and most preferably 100%. The methods described in Hu Y & Smyth G K., J Immunol Methods. 2009 Aug. 15; 347(1-2): 70-8 and Ishizawa K & Rasheed Z A. et al., Cell Stem Cell. 2010 Sep. 3; 7(3): 279-82 can also be employed. In this method, 1,000, 100, or 10 cells are transplanted into an immunodeficient animal and the frequency of cancer cell mass formation is analyzed using extreme limiting dilution analysis (Hu Y & Smyth G K., J Immunol Methods. 2009 Aug. 15; 347(1-2): 70-8). In the present invention, a "homogeneous cancer stem cell population" from which cells having no cancer-forming ability have been substantially removed means that the frequency of cancer stem cells in this analysis is 1/20 or higher, preferably 1/10 or higher, more preferably 1/5 or higher, even more preferably 1/3 or higher, even more preferably 1/2 or higher, and most preferably 1/1.

Extreme limiting dilution analysis (ELDA) is a software application for limiting dilution analysis (LDA) in accordance with the needs of stem cell assays. ELDA is a limiting dilution analysis software to provide meaningful confidence intervals for all LDA data sets, including those with 0% or 100% responses, which includes a test of the adequacy of the single-hit hypothesis, tests for frequency differences between multiple data sets, and such. Those skilled in the art can conduct an analysis method based on the ELDA proposed by Hu et al. (J Immunol Methods. (2009) 347 (1-2), 70-78) by applying the method described in the above non-patent documents or using the online analysis tool provided at http://bioinf.wehi.edu.au/software/elda/.

By using the present invention, cancer stem cells can be prepared in large quantities. In principle, a desired number of cancer stem cells can be obtained by increasing flasks for adherent culture. For example, when a T150 flask is used, $4 \times 10^7$ or more cells can be generally obtained when cultured to confluence, and therefore $2 \times 10^8$ or more cells can be prepared by using five flasks. Thus, a desired number of cells can be prepared in the present invention.

In the cancer stem cell population of the present invention, preferably, cells having no cancer-forming ability have been substantially removed. Also, the population may contain $1 \times 10^4$ or more cancer stem cells, more preferably $1 \times 10^5$ or more, even more preferably $1 \times 10^6$ or more, even more preferably $1 \times 10^7$ or more, still more preferably $1 \times 10^8$ or more, and most preferably $1 \times 10^9$ or more cancer stem cells.

A second aspect of the present invention provides a method for preparing the cell population of the present invention.

The cell population of the present invention can be prepared, for example, by adherently culturing a cell group containing cancer stem cells.

Cell groups containing cancer stem cells that can be used include cells into which a gene of a cancer virus (e.g., SV40) or an oncogene such as Ras has been introduced, or cell lines established from cancer tissues.

The cell group containing cancer stem cells is preferably a cell group reproducing the hierarchical structure of a cancer tissue. For example, collected cancer tissues may be used. Preferably, established cancer cell lines prepared by transplanting and passaging cancer in a non-human animal can be used. More preferably, established cancer cell lines prepared by transplanting and passaging cancer in an immunodeficient animal can be used. Most preferably, NOG established cell line prepared by transplanting and passaging a cancer tissue in an NOG mouse can be used.

Furthermore, the cell group containing cancer stem cells may be a spheroid formed by spheroid culture, or a cell group containing cells positive for at least one or more cancer stem cell markers selected from CD24, CD29, CD34, CD44, CD49f, CD56, CD90, CD117, CD133, CD135, CD166, CD184, CD271, CD326, Aldefluor, ABCG2, ABCG5, LGR5, and Msi1.

The source of the cell group is not particularly limited, and it is possible to use those derived from mammals such as human, monkey, chimpanzee, dog, cow, pig, rabbit, rat, and mouse, but it is preferred to use those derived from human.

NOG established cancer cell lines can be prepared by methods known to those skilled in the art. For example, the method described in Fujii E. et al., Pathol int. 2008; 58: 559-567 can be used. Such cell lines can be established by physically mincing surgically-resected human colon cancer, stomach cancer, lung cancer, breast cancer, pancreatic cancer, or the like with scissors, and subcutaneously transplanting and passaging it in NOG mice. NOG established cancer cell lines maintain the characteristics of original human cancer tissue even after passages.

In the adherent culture step, the medium to be used is not particularly limited as long as it is for adherent culture, but a serum-free stem cell medium is preferably used.

Adherent culture refers to culturing and passaging cells while allowing them to adhere to an adherent culture flask, plate, or dish after seeding, i.e., culturing without floating cells. Confluently grown cells are detached with Accutase and passaged in a new adherent culture flask, plate, or dish to continue culture.

Culture solutions that can be used in the present invention are not particularly limited as long as they can be used to culture cancer stem cells. For example, a conventionally-known basal culture solution supplemented with EGF, bFGF, hLIF, HGF, NGF, NSF-1, TGFβ, TNFα, heparin, BSA, insulin, transferrin, putrescine, selenite, progesterone, hydrocortisone, D-(+)-glucose, sodium bicarbonate, HEPES, L-glutamine, and N-acetylcysteine, or a mixture of these can be used as a culture solution. The concentration of EGF is not particularly limited but is 0.1-100 ng/mL, preferably 0.5-50 ng/mL, and more preferably 1-20 ng/mL. The concentration of bFGF is not particularly limited but is 0.1-100 ng/mL, preferably 0.5-50 ng/mL, and more preferably 1-20 ng/mL. The concentration of hLIF is not particularly limited but is 0.1-100 ng/mL, preferably 0.5-50 ng/mL, and more preferably 1-20 ng/mL. The concentration of HGF is not particularly limited but is 0.1-100 ng/mL, and preferably 1-50 ng/mL. The concentration of NGF is not particularly limited but is 0.1-100 ng/mL, and preferably 1-50 ng/mL. The concentration of NSF-1 is not particularly limited but is 0.1-100 ng/mL, and preferably 1-50 ng/mL. The concentration of TGFβ is not particularly limited but is 0.1-100 ng/mL, and preferably 1-50 ng/mL. The concentration of TNFα is not particularly limited but is 0.1-100 ng/mL, and preferably 1-50 ng/mL. The concentration of heparin is not particularly limited but is 10 ng/mL-10 μg/mL, and preferably 2-5 μg/mL. The concentration of BSA is not particularly limited but is 0.1-10 mg/mL, and preferably 1-8 mg/mL. The concentration of insulin is not particularly limited but is 1-100 μg/mL, and preferably 10-50 μg/mL. The concentration of transferrin is not particularly limited but is 10-500 μg/mL, and preferably 50-200 μg/mL. The concentration of putrescine is not particularly limited but is 1-50 μg/mL, and preferably 10-20 μg/mL. The concentration of selenite is not particularly limited but is 1-50 nM, and preferably 20-40 nM. The concentration of progesterone is not particularly limited but is 1-50 nM, and preferably 10-30 nM. The concentration of hydrocortisone is not particularly limited but is 10 ng/mL-10 μg/mL, and preferably 100 ng/mL-1 μg/mL. The concentration of D-(+)-glucose is not particularly limited but is 1-20 mg/mL, and preferably 5-10 mg/mL. The concentration of sodium bicarbonate is not particularly limited but is 0.1-5 mg/mL, and preferably 0.5-2 mg/mL. The concentration of HEPES is not particularly limited but is 0.1-50 mM, and preferably 1-20 mM. The concentration of L-glutamine is not particularly limited but is 0.1-10 mM, and preferably 1-5 mM. The concentration of N-acetylcysteine is not particularly limited but is 1-200 μg/mL, and preferably 10-100 μg/mL. The known basal culture solution is not particularly limited as long as it is suitable for culturing cancer cells from which cancer stem cells originate, but includes, for example, DMEM/F12, DMEM, F10, F12, IMDM, EMEM, RPMI-1640, MEM, BME, Mocoy's 5A, and MCDB131. Of these, DMEM/F12 is preferred.

The most preferable stem cell media include D-MEM/F12 medium supplemented with 20 ng/mL EGF, 10 ng/mL bFGF, 4 μg/mL heparin, 4 mg/mL BSA, 25 μg/mL insulin, 100 μg/mL transferrin, 16 μg/mL putrescine, 30 nM selenite, 20 nM progesterone, and 2.9 mg/mL D-(+)-glucose.

Preferably, the cell group containing cancer stem cells is allowed to proliferate in advance of adherent culture.

Allowing a cell group to proliferate refers to, for example, allowing it to grow by spheroid culture or by transplanting and passaging it in a non-human animal, but is not particularly limited thereto.

Spheroid culture refers to seeding and culturing cells in a floating state in a non-adherent culture flask, plate, or dish with the above-mentioned medium that can be used for culturing stem cells. A cell mass formed in such floating culture is called spheroid.

An immunodeficient animal can be used as a non-human animal as it is less likely to cause rejection reaction. As an immunodeficient animal, it is preferred to use a non-human animal deficient in functional T cells, such as a nude mouse and rat, and a non-human animal deficient in functional T and B cells, such as a SCID mouse and a NOD-SCID mouse. Particularly, a mouse deficient in T, B, and NK cells (for example, a severely immunodeficient mouse obtained by crossing a SCID, RAG2KO, or RAG1KO mouse with an IL-2Rg$^{null}$ mouse, which includes NOD/SCID/gammac$^{null}$ mouse, NOD-scid, IL-2Rg$^{null}$ mouse, and BALB/c_Rag2$^{null}$, IL-2 Rg$^{null}$ mouse), which shows excellent transplantability, is preferably used.

Regarding the age of non-human animals, when athymic nude mice, SCID mice, NOD/SCID mice, or NOG mice are used, those of 4-100 weeks old are preferably used.

NOG mice can be produced, for example, by the method described in WO 2002/043477, or can be obtained from the Central Institute for Experimental Animals or the Jackson Laboratory (NSG mice).

Cells to be transplanted may be any types of cells including a cell mass, a tissue section, singly dispersed cells, cells cultured after isolation, and cells transplanted to another animal and again isolated from the animal. However, dispersed cells are preferred. The number of cells to be transplanted may be $10^6$ or less, but a greater number of cells may be transplanted.

Subcutaneous transplantation is preferable because of its simple transplantation techniques. However, the site of transplantation is not particularly limited and preferably appropriately selected depending on the animal used. The procedure for transplanting NOG established cancer cell lines is not particularly limited, and any conventional transplantation procedures can be used.

The cell population in the present method can be prepared, for example, by adherently culturing a cancer tissue collected from a patient in a serum-free stem cell medium. It does not matter what culture process the cell group has undergone for additional proliferation before the adherent culture. For example, the cell population in the present method can also be prepared by spheroid culture of a cancer tissue collected from a patient, followed by adherent culture using a serum-free stem cell medium. In addition, the cell population can also be prepared by transplanting and passaging a cancer tissue collected from a patient in a non-human animal, and then adherently culturing it using a serum-free stem cell medium. Furthermore, it is most preferred to prepare the cell population by transplanting and passaging in a NOG mouse a cancer tissue collected from a patient, and then adherently culturing a thus produced NOG established cancer cell line using a serum-free stem cell medium, because the cell population of the present invention can be efficiently obtained in large quantities.

The cell population of the present invention can be used to search for drug target molecules and to assess drugs. Assessment methods for drugs include screening for drugs and screening for anticancer agents.

Methods of searching for target molecules include, but are not limited to, methods for identifying genes such as DNAs and RNAs highly expressed in cancer stem cells (e.g., cancer stem cell markers) using Gene-chip analysis, and methods for identifying proteins, peptides, or metabolites highly expressed in cancer stem cells using proteomics.

Screening methods for searching for target molecules include methods in which substances that inhibit the growth of cancer stem cells are screened from a small molecule library, antibody library, micro RNA library, or RNAi library, using cell growth inhibition assay. After an inhibitor is obtained, its target can be revealed.

After antibodies are obtained through immunization with cancer stem cells, binding antibodies can be screened by ELISA, or growth-inhibiting antibodies can be screened by cell growth inhibition assay. After binding or functional antibodies are obtained, their antigens can be identified to reveal target molecules.

The cancer stem cell population of the present invention can be used to evaluate the effects of existing drugs and drugs under development on cancer stem cells and find new pharmaceutical effects.

Concentrating homogeneous cancer stem cells makes the following things possible, for example.

1. efficiently identifying nucleic acids (DNA and RNA), proteins, etc. specifically expressed in cancer stem cells, and elucidating the functions of these molecules;
2. efficiently identifying nucleic acids (DNA and RNA), proteins, etc. specifically expressed in cancer stem cells, and searching/screening for drug candidates that inhibit them;
3. using results of biological function analyses of concentrated cancer stem cells (invasiveness, division rate, and such) as indices for prognosis of cancer;
4. using results of biological function analyses of concentrated cancer stem cells (invasiveness, division rate, and such) as indices to reclassify cancers and search/screen for anticancer agents in each classification;
5. studying the process in which concentrated cancer stem cells produce differentiated cells constituting the majority of cancer tissue, and searching/screening for anticancer agents (cancer silencers) that suppress this process;
6. detecting biological reactions characteristic of cancer stem cells by adjusting culture conditions for cancer stem cells (oxygen partial pressure, nutrient conditions, and anticancer agent treatment) toward poor conditions, and examining the causes of the durability of cancer stem cells; and
7. detecting biological reactions characteristic of cancer stem cells by adjusting culture conditions for cancer stem cells (oxygen partial pressure, nutrient conditions, and anticancer agent treatment) toward poor conditions, and searching/screening for anticancer agents that inhibit the durability of cancer stem cells.

Methods of Searching for Drug Target Molecules

The present invention relates to methods of searching for drug target molecules, in which assessment is performed using as an index a hierarchical structure formed from cancer stem cells, a cancer development process originating from cancer stem cells, or a biological property of cancer stem cells, in a non-human animal model transplanted with the cancer stem cell population of the present invention, or a culture system of the cancer stem cell population of the invention under in vitro conditions.

In this method, when a non-human animal model transplanted with a cancer stem cell population is used, drug target molecules can be searched for by the following steps (1) to (4):

(1) producing a non-human animal model by transplanting a cancer stem cell population to a non-human animal;
(2) collecting a tissue section showing a tissue structure characteristic of the cancer development process of a cancer stem cell population or showing a biological property thereof;
(3) examining the tissue section collected in (2) for the expression of DNAs, RNAs, proteins, peptides, or metabolites; and
(4) identifying DNAs, RNAs, proteins, peptides or metabolites that vary depending on a hierarchical structure formed from cancer stem cells, a cancer development process originating from cancer stem cells, and a biological property of cancer stem cells, in the tissue section.

In this method, when a culture system of the cancer stem cell population under in vitro conditions is used, drug target molecules can be searched for by the following steps (1) to (3):

(1) culturing a cancer stem cell population under in vitro conditions to reproduce a characteristic structure of a cancer development process originating from cancer stem cells or a biological property of cancer stem cells;
(2) examining the expression of DNAs, RNAs, proteins, and peptides or metabolites in the cultured cells with the reproduced characteristic structure; and
(3) identifying DNAs, RNAs, proteins, peptides or metabolites that vary depending on a hierarchical structure formed from cancer stem cells, a cancer development process originating from cancer stem cells, and a biological property of cancer stem cells, in the cultured cells.

In the present invention, structures of tissues or cell lines characteristic of a cancer development process can be observed by HE staining and immunohistochemical (IHC) staining of sliced tissue specimens prepared by known specimen preparation methods such as AMeX. If a hierarchical structure, cancer development process, or a biological property specific for the above-mentioned human tumor tissue is observed in the test tissue, the tissue is regarded as a cancer-related tissue, and the expression of DNAs, RNAs, proteins, peptides and metabolites is examined. The expression of DNAs, RNAs, proteins, peptides, and metabolites can be examined by, without particular limitation, any conventional expression examination methods. RNA molecules include micro RNAs, siRNAs, tRNAs, snRNAs, mRNAs, and non-coding RNAs. For example, the mRNA of each gene is extracted according to a standard method, and the transcription level of each gene can be measured by northern hybridization or RT-PCR using this mRNA as a template. In addition, the expression level of each gene can be measured using DNA array techniques. Furthermore, fractions containing a protein encoded by each gene are collected according to a standard method, and the translation level of each gene can be measured by detecting the expression level of each protein by electrophoresis methods such as SDS-PAGE. Moreover, the translation level of each gene can be measured by detecting the expression of each protein by Western blotting using an antibody against each protein. By these methods, target molecules of anticancer agents can be searched for.

A non-limiting embodiment of the above drug target molecules preferably includes CD133, CD44, EpCAM, CD166, CD24, CD29, and LGR5, which are specifically expressed in the cancer stem cells of the present invention as described in the Examples.

In the present invention, the above-mentioned drugs include, but are not particularly limited to, anti-inflammatory agents, immunosuppressive agents, antiviral agents, angiogenesis inhibitors, steroids, enzyme inhibitors, antibiotics, antihistamines, anticoagulants, anti-infectives, analgesics, agents for treating diabetes, agents for treating arthritis, anti-asthmatic agents, anti-insomnia agents, antiemetics, agents for treating migraine, anticonvulsants, antidepressants, antipsychotics, antipyretics, agents for treating Parkinson's disease, agents for treating Alzheimer's disease, sympathomimetics, agents for treating arrhythmia, antihypertensives, diuretics, antidiuretics, anticoagulants, vasodilators, and sedatives. However, anticancer agents are preferred. Also, the above drugs include, but are not particularly limited to, protein agents, nucleic acid agents, small molecule agents, and cellular agents. In the present invention, the target molecules include, but are not particularly limited to, membrane receptors, enzymes, ion channels, transcription factors, and nuclear receptors, and preferably are cancer cell markers.

Methods for Assessing Drugs

The present invention relates to methods for assessing drugs, in which assessment is performed using as an index a hierarchical structure formed from cancer stem cells, a cancer development process originating from cancer stem cells, or a biological property of cancer stem cells, in a non-human animal model transplanted with the cancer stem cell population of the present invention or a culture system of the cancer stem cell population under in vitro conditions.

In this method, when a non-human animal model transplanted with the cancer stem cell population of the present invention is used, drugs can be assessed by the following steps (1) to (5):

(1) producing a non-human animal model by transplanting a cancer stem cell population into a non-human animal;
(2) administering a test substance to the non-human animal model of (1);
(3) collecting a tissue section showing a tissue structure characteristic of a cancer development process originating from cancer stem cells or showing a biological property thereof;
(4) observing a change in cancer stem cells over time, a cancer development process, or a biological property thereof, in the tissue section; and
(5) identifying a hierarchical structure formed from cancer stem cells, a cancer development process originating from cancer stem cells, or a biological property of cancer stem cells, that is inhibited by the test substance.

In this method, when a culture system of the cancer stem cell population under in vitro conditions is used, drugs can be assessed by the following steps (1) to (3):

(1) culturing a cancer stem cell population under in vitro conditions to reproduce a characteristic structure of a cancer development process originating from cancer stem cells or a biological property of cancer stem cells;
(2) treating the cultured cells of (1) with a test substance;
(3) observing a change in a hierarchical structure formed from cancer stem cells, a cancer development process originating from cancer stem cells, or a biological property of cancer stem cells; and
(4) identifying a hierarchical structure formed from cancer stem cells, a cancer development process originating from cancer stem cells, or a biological property of cancer stem cells, that is inhibited by the test substance.

Methods of Screening for Drugs

The present invention relates to methods of screening for medicaments, in which assessment is performed by using as an index a hierarchical structure formed from cancer stem cells, a cancer development process originating from cancer stem cells, or a biological property of cancer stem cells, in a non-human animal model transplanted with the cancer stem cell population of the present invention or a culture system of the cancer stem cell population under in vitro conditions.

In this method, when a non-human animal model transplanted with the cancer stem cell population of the present invention is used, drugs can be screened by the following steps (1) to (5):

(1) producing a non-human animal model by transplanting a cancer stem cell population into a non-human animal;

(2) administering a test substance to the non-human animal model of (1);
(3) collecting a tissue section showing a tissue structure characteristic of a cancer development process originating from cancer stem cells or showing a biological property thereof;
(4) observing a change in cancer stem cells over time, a cancer development process, or a biological property thereof, in the tissue fragment; and
(5) identifying a test substance that inhibits formation of a hierarchical structure formed from specific cancer stem cells, a cancer development process originating from cancer stem cells, or a biological property of cancer stem cells.

In this method, when a culture system of the cancer stem cell population under in vitro conditions is used, drugs can be screened by the following steps (1) to (4):
(1) culturing a cancer stem cell population under in vitro conditions to reproduce a characteristic structure of each cancer development process or a biological property thereof;
(2) treating the cultured cells of (1) with a test substance;
(3) observing a change in a hierarchical structure of cancer stem cells over time, a cancer development process, or a biological property thereof, in the cultured cells; and
(4) identifying formation of a hierarchical structure of cancer stem cells, a cancer development process, or a biological property thereof, that is inhibited by the test substance.

Anticancer agents can be screened by the above screening methods.

The "test substances" in the methods of the present invention include, but are not particularly limited to, for example, single compounds such as natural compounds, organic compounds, inorganic compounds, proteins, antibodies, peptides, and amino acids, and compound libraries, expression products from gene libraries, cell extracts, cell culture supernatants, products from fermentative microorganisms, extracts from marine organisms, plant extracts, prokaryotic cell extracts, unicellular eukaryotic cell extracts, or animal cell extracts. These may be purified products or may be crude products such as extracts from plants, animals, microorganisms, and such. In addition, methods of producing test substances are not particularly limited, and such substances may be isolated from natural products, chemically or biochemically synthesized, or prepared by genetic engineering.

The above test samples may be suitably labeled as needed. Labels include, for example, radioactive labels and fluorescent labels. In addition to the above test samples, mixtures of two or more of these test samples are included.

In this method, methods of administering a test substance to a non-human animal model are not particularly limited. Depending on the type of the test substance to be administered, oral administration or parenteral administration such as subcutaneous, intravenous, topical, transdermal, and enteral (rectal) administration can be appropriately selected.

In this method, methods of treating cultured cells of the cancer stem cell population with a test substance are not particularly limited. The treatment can be conducted by adding a test sample to the culture solution of the cells or their cell extract. When the test sample is a protein, for example, a vector containing DNA encoding the protein can be introduced into a cancer stem cell population, or the vector can be added to the cell extract of a cancer stem cell population. In addition, for example, a two-hybrid method using yeast or animal cells can be used.

Test substances can be assessed by removing the transplanted tissue (tissue transplanted with a cancer stem cell population) from the animal model and observe the histological characteristics of the transplanted tissue, or by measuring the histological characteristics in a cell culture system.

Specifically, test substances can be assessed in the non-human animal model or the culture system of the cancer stem cell population under in vitro conditions by observing a hierarchical structure formed from cancer stem cells of the transplanted tissue or culture system to check the formation of a hierarchical structure unique to human cancer cells or check the effects on a cancer development process characteristic of human cancer diseases. Structures of tissues or cell lines characteristic of a cancer development process can be observed by HE staining and immunohistochemical (IHC) staining of sliced tissue specimens prepared by known specimen preparation methods such as AMeX.

More specifically, the above assessment of test substances can be performed as follows: the hierarchical structure of cancer stem cells of the transplanted tissue or culture system is also observed in the control non-human animal model or cancer stem cell population which has received no test substance to check the formation of a hierarchical structure unique to human cancer cells, and then the hierarchical structure of cancer stem cells is compared between the non-human animal model or cancer stem cell population which have received a test substance and the above control animal. In this case, if any hierarchical structure unique to human cancer cells is, as compared to the control animal, not observed or is reduced in percentage in the transplanted tissue or culture system to which the test substance is administered, the test substance can be selected as an active substance having therapeutic or prophylactic effects on human cancer diseases.

More specifically, the above assessment of test substances can be performed as follows: the cancer development process of the transplanted tissue or culture system is also observed in the control non-human animal model or cancer stem cell population which has received no test substance to check if a cancer development process unique to human cancer cells can be observed, and the cancer development process of cancer stem cells is compared between the non-human animal model or cancer stem cell population which has received a test substance and the above control animal. In this case, if any cancer development process unique to human cancer cells is, as compared to the control animal, not observed in the transplanted tissue or culture system to which the test substance is administered, the test substance can be selected as an active substance having therapeutic or prophylactic effects on human cancer diseases.

Further, more specifically, the above assessment of test substances can be performed as follows: the biological properties of cancer stem cells in the transplanted tissue or culture system are also observed in the control non-human animal model or cancer stem cell population which has received no test substance to check if a biological property unique to human cancer cells can be observed, and the property of cancer stem cells is compared between the non-human animal model or cancer stem cell population which has received the test substance and the above control animal. In this case, if any biological property unique to human cancer cells is, as compared to the control animal, not observed in the transplanted tissue or culture system to which the test substance is administered, the test substance can be selected as an active substance having therapeutic or prophylactic effects on human cancer diseases.

If necessary, prophylactically or therapeutically effective substances for human cancer diseases selected by the above screening methods of the present invention can be further selected as more effective and highly applicable prophylactically or therapeutically active substances by conducting other efficacy and safety tests and by further conducting clinical trials on human cancer patients.

Prophylactically or therapeutically effective substances thus selected can also be produced industrially through chemical synthesis, biochemical synthesis (fermentation), or genetic manipulation, based on the results of their structural analyses.

All prior art references cited in the present specification are herein incorporated by reference.

EXAMPLES

Hereinafter, the present invention will be described in detail by these Examples, but the present invention is not limited thereto.

[Example 1] Preparation and Evaluation of Cancer Stem Cells and Cancer-Forming Cells Using Human Cancer Cell Lines (1) Morphological Evaluation of Colon Cancer Lines Transplanted into Mice Colon cancer specimens were obtained from patients with consent under the approval of the ethics committees of the PharmaLogicals Research (Singapore) and the Parkway Laboratory Services (Singapore). Tumors were minced with scissors and transplanted into the flanks of NOG mice. Human colon cancer xenografts were maintained through passage in NOG mice provided by the Central Institute for Experimental Animals (Japan). Mice used in this study were treated according to the animal experimentation guidelines of the PharmaLogicals Research. Colon cancer cell lines established in NOG or SCID mice were subcutaneously transplanted into NOG mice to generate cancer cell masses. The cancer cell masses were excised, fixed for 16-24 hours in 4% paraformaldehyde at 4° C., and embedded by the AMeX method to prepare sliced tissue specimens. The tissue specimens were HE-stained. Results are shown in FIG. 1. Colon cancer lines PLR123, PLR59, and PLR325 that had been transplanted into NOG mice showed morphological structures similar to those observed in human tissue, suggesting no influence from NOG mice. The colon cancer line PLR357 that had been transplanted into NOG mice showed morphological changes, suggesting that it is not suitable for transplantation experiments in NOG mice.

(2) Preparation of Cells from Cancer Cell Masses

Cancer cell masses were removed from NOG mice, and physically minced with scissors. Subsequently, the tissue was suspended several times in DPBS (Invitrogen, Cat. No. 14190144) and transferred into an enzyme solution containing Collagenase/Dispase (Roche, Cat. No. 10 269 638 001) and DNase I (Roche, Cat. No. 11 284 932 001), followed by 3 hours of stirring at 37° C. Furthermore, Lysing Buffer (BD, Cat. No. 555899) was added to cells that had been fragmented by repeated pipetting to remove mouse erythrocytes. Finally, the cell solution was passed through a 40 µm cell strainer (BD, Cat. No. 352340), and suspended several times in DPBS to prepare a cell solution.

(3) Detection of Cancer Stem Cell Marker-Positive Cells

Cells prepared from a cancer cell mass were suspended in FACS buffer (2% fetal bovine serum/DPBS), and allowed to react for 30 minutes at 4° C. after the addition of Rat mAb to mouse MHC class I (Abcam, Cat. No. ab15680). The cells were washed once with FACS buffer, and allowed to react at 4° C. for 30 minutes with PE-labeled goat Ab to rat IgG2a (BioLegend, Cat. No. 405406) or APC-labeled goat Ab to rat IgG2a (BioLegend, Cat. No. 405407) as a secondary antibody, the 7-AAD Viability Dye (Beckman Coulter, Cat. No. A07704) for staining dead cells, or as a cancer stem cell marker, FITC-labeled mouse mAb to human CD326 (Ep-CAM) (Miltenyi Biotec, Cat. No. 130-080-301), PE-labeled mouse mAb to human CD133/1 (AC133) (Miltenyi Biotec, Cat. No. 130-080-801), or PE-labeled mouse mAb to human CD44 (BD Pharmingen, Cat. No. 550989). Subsequently, the cells were washed once with FACS buffer and subjected to flow cytometric analysis. Aldehyde dehydrogenase (ALDH) activity was detected using the AldeFluor Kit (Stemcell Technologies, Cat. No. 01700) according to the manufacturer's recommended procedures. EPICS ALTRA (Beckman Coulter) was used for flow cytometric analysis to analyze cancer stem cell markers for cells that are negative for mouse MHC class I- and 7-AAD Viability Dye. Results are shown in FIG. 2. Cancer stem cell marker-positive cells were observed in cancer cell masses formed from colon cancer lines PLR123, PLR59, and PLR325. The moderately differentiated colon cancer lines, PLR123 and PLR59, generated a mixture of marker-positive and -negative cells, i.e., a heterogeneous cell population. The poorly differentiated colon cancer line PLR325 generated cells that were all positive for EpCAM, AC133, and ALDH and all negative for CD44, i.e., a homogeneous cell population.

(4) Removal of Mouse Cells from a Cell Solution

Cells prepared from a cancer cell mass were suspended in FACS buffer, and allowed to react at 4° C. for 15 minutes after the addition of Rat mAb to mouse MHC class I. The cells were washed once with FACS buffer, and allowed to react at 4° C. for 15 minutes with PE-labeled goat Ab to rat IgG2a as a secondary antibody. Furthermore, the cells were washed once with FACS buffer. Subsequently, mouse cells were removed by cell sorting using EPICS ALTRA or the EasySep Mouse PE Positive Selection Kit (Stemcell Technologies, Cat. No. 18554) according to the manufacturer's recommended procedures. Cell purity was analyzed using EPICS ALTRA. Results are shown in FIG. 3. In cancer cell masses formed from the colon cancer lines PLR123, PLR59, and PLR325, 95% or more of the cells were negative for mouse MHC class I after the removal of mouse cells.

(5) Cancer Formation Test of Colon Cancer Lines

After mouse cells were removed from the above cell solution prepared in (2), the cancer cells were confirmed microscopically to be single cells, and the cells were counted. Matrigel Basement Membrane Matrix, diluted to 50% with Hank's Balanced Salt Solution, was used to prepare 10,000, 1,000, or 100 cells/mL solutions. Each cell solution was subcutaneously transplanted into NOG mice at 100 µL/spot, i.e., 1,000, 100, and 10 cells/spot to evaluate the number of tumors formed. Results are shown in Table 1. The moderately differentiated colon cancer lines PLR123 and PLR59 formed cancer when 100 cells/spot or more were transplanted. The poorly differentiated colon cancer line PLR325 formed cancer when 10 cells/spot or more were transplanted. The ratio of cells with cancer-forming ability was analyzed using an extreme limiting dilution analysis. Colon cancer lines PLR123, PLR59, and PLR325 contained cells with cancer-forming ability at a ratio of 1/161, 1/195, or 1/14, respectively.

TABLE 1

| Name of cells | Days after transplantation | Cancer formation ratio | | | Frequency |
|---|---|---|---|---|---|
| | | 1,000 cells | 100 cells | 10 cells | |
| NOG established colon cancer line PLR123 Moderately differentiated | 49 days | 12/12 | 6/12 | 0/12 | 1/161 |
| NOG established colon cancer line PLR59 Moderately differentiated | 49 days | 12/12 | 5/12 | 0/12 | 1/195 |
| NOG established colon cancer line PLR325 Poorly differentiated | 49 days | 6/6 | 6/6 | 3/6 | 1/14 |

Figure 4:
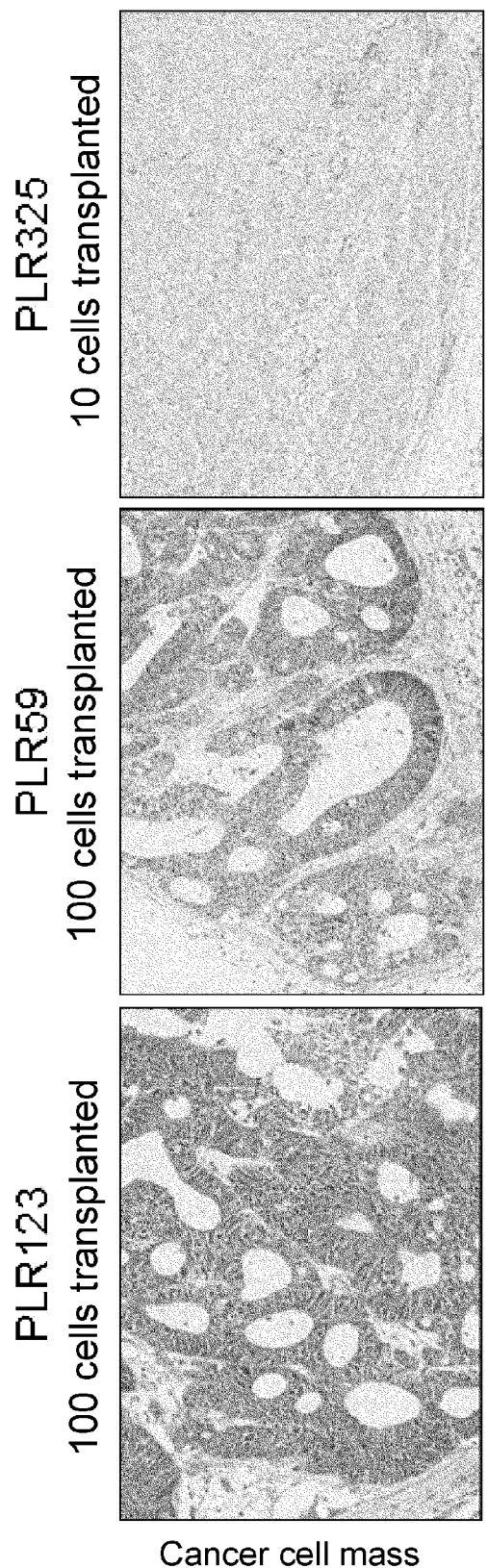
FIG. 4 presents a photograph showing an HE-stained tissue specimen. The moderately differentiated colon cancer lines PLR123 and PLR59 showed a hierarchical structure. On the other hand, hierarchical structure was not observed in the poorly differentiated colon cancer line PLR325.

(6) Histological Evaluation of Hierarchical Structure Formation in Colon Cancer Lines Cancer cell masses that were formed from 100 or 10 cells were excised, fixed for 16-24 hours in 4% paraformaldehyde at 4° C., and embedded by the AMeX method to prepare sliced tissue specimens. The tissue specimens were subjected to HE staining. Results are shown in FIG. 4. The moderately differentiated colon cancer lines PLR123 and PLR59 showed a hierarchical structure, suggesting that the colon cancer lines PLR123 and PLR59 are cancer stem cells. On the other hand, hierarchical structure was not observed in the poorly differentiated colon cancer line PLR325, suggesting that the colon cancer line PLR325 is cancer-forming cells.

(7) Detection of Normal Intestinal Stem Cell Marker LGR5 Protein

Figure 5:
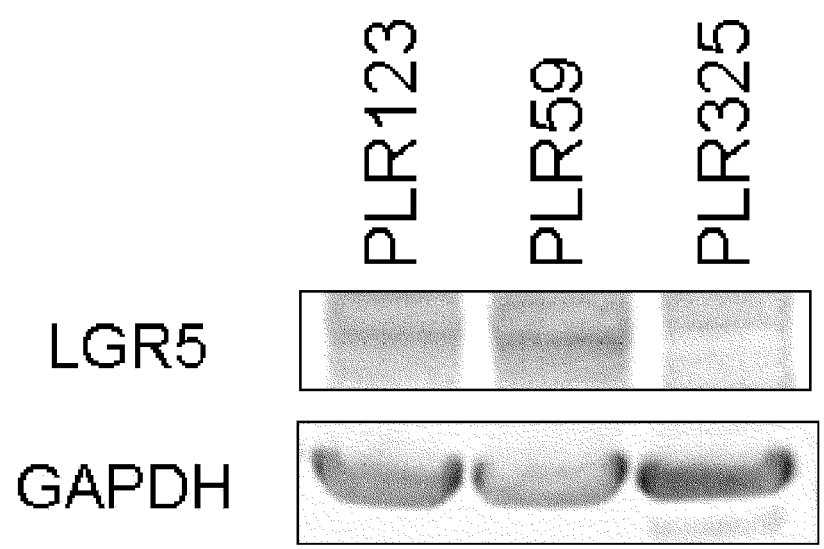
FIG. 5 shows the LGR5 protein expression by Western blotting. The LGR5 protein was detected in the moderately differentiated colon cancer lines PLR123 and PLR59, suggesting the presence of normal intestinal stem cell marker-positive cells. On the other hand, no LGR5 protein was detected in the poorly differentiated colon cancer line PLR325.

After mouse cells were removed from the above cell solution prepared in (2), cell lysates of colon cancer lines, PLR123, PLR59, and PLR325 were prepared using RIPA buffer (Sigma, Cat. No. R0278), and then SDS-PAGE and Western blotting were carried out. Rabbit mAb to human GPR49 (Abcam, Cat. No. Ab75850) was used to detect LGR5 protein. Mouse mAb to human GAPDH (Santa Cruz, Cat. No. Sc-69778) was used as a positive control. Results are shown in FIG. 5. LGR5 protein was detected in the moderately differentiated colon cancer lines PLR123 and PLR59, suggesting the presence of normal intestinal stem cell marker-positive cells. No LGR5 protein was detected in the poorly differentiated colon cancer line PLR325.

[Example 2] Characterization of Commercially Available In Vitro Cancer Cell Lines (1) Culture of Commercially Available In Vitro Cancer Cell Lines Commercially available in vitro cancer cell lines were cultured according to a standard method (e.g., at 37° C. and in the presence of 5% $CO_2$) in a medium recommended by ATCC (http://www.atcc.org/). The fetal bovine serum in all the media used was inactivated by incubation at 56° C. for 30 minutes or longer before use.

(2) Detection of Cancer Stem Cell Marker-Positive Cells

Figure 6:
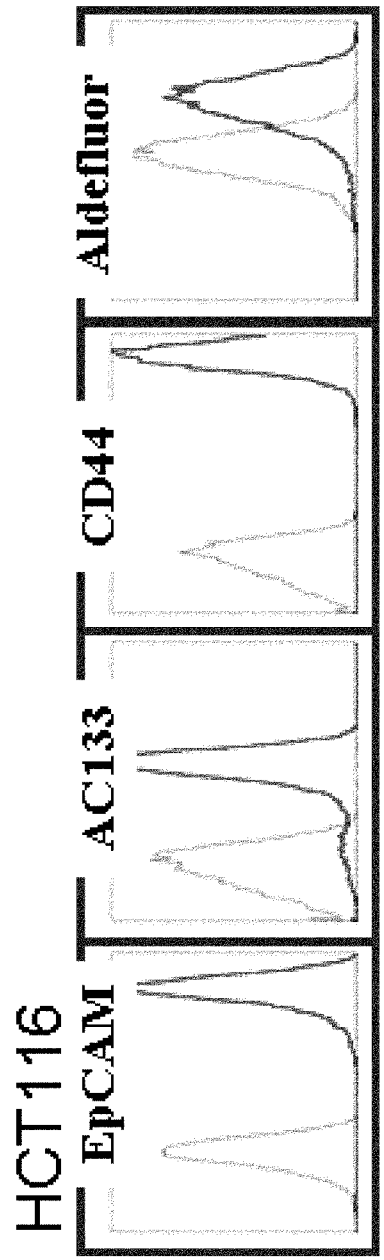
FIG. 6 shows results of the flow cytometric analysis sing cancer stem cell markers for 7-AAD Viability Dye-negative cells by EPICS ALTRA. The commercially available colon cancer line HCT116 was a homogeneous cell population characterized in that most cells were positive for the stem cell markers.

The cancer cells cultured in vitro were detached from the flask with Accutase (ICT, Cat. No. AT104), suspended in FACS buffer, and allowed to react at 4° C. for 30 minutes with the 7-AAD Viability Dye (Beckman Coulter, Cat. No. A07704) for staining dead cells, or as a cancer stem cell marker, FITC-labeled mouse mAb to human CD326 (Ep-CAM), PE-labeled mouse mAb to human CD133/1 (AC133), or PE-labeled mouse mAb to human CD44. Subsequently, the cells were washed once with FACS buffer and subjected to flow cytometric analysis. Aldehyde dehydrogenase (ALDH) activity was detected using the AldeFluor Kit according to the manufacturer's recommended procedures. EPICS ALTRA (Beckman Coulter) was used for the flow cytometric analysis to analyze cancer stem cell markers in the 7-AAD Viability Dye-negative cells. Results are shown in FIG. 6. HCT116 was a homogeneous cell population characterized in that most cells were positive for the stem cell markers.

(3) Cancer Formation Test of Commercially Available In Vitro Cell Lines

The cancer cells cultured in vitro were detached from the flask with Accutase, and confirmed microscopically to be single cells, followed by counting. Matrigel Basement Membrane Matrix, diluted to 50% with Hank's Balanced Salt Solution, was used to prepare 10,000, 1,000, or 100 cells/mL solutions. Each cell solution was subcutaneously transplanted into NOG mice at 100 µL/spot, i.e., 1,000, 100, and 10 cells/spot to evaluate the number of tumors formed. Results are shown in Table 2. In HCT116, cancer formation was confirmed when 10 cells/spot or more were transplanted. The ratio of cells with cancer-forming ability was analyzed using an extreme limiting dilution analysis. It demonstrated that the ratio of cells with cancer-forming ability was 1/9 in HCT116.

TABLE 2

| Name of cells | Days after transplantation | Cancer formation ratio | | | Frequency |
|---|---|---|---|---|---|
| | | 1,000 cells | 100 cells | 10 cells | |
| HCT116 Commercially available in vitro cell line | 48 days | — | 6/6 | 4/6 | 1/9 |

Figure 7:
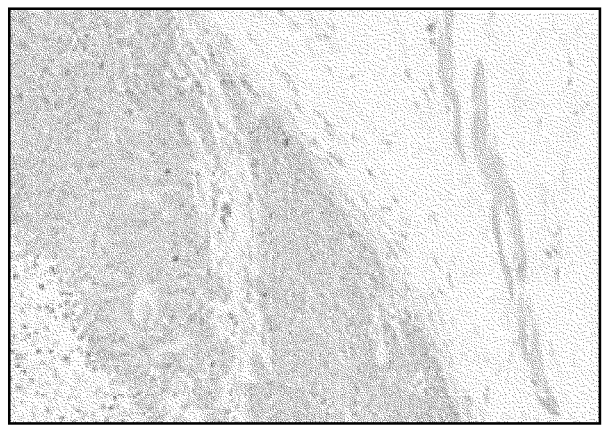
FIG. 7 presents a photograph showing an HE-stained tissue specimen. Hierarchical structure was not observed in the commercially available colon cancer line HCT116.

(4) Histological Evaluation of Hierarchical Structure Formation in Commercially Available In Vitro Cell Lines Cancer cell masses formed from 10 cells were excised, fixed for 16-24 hours in 4% paraformaldehyde at 4° C., and embedded by the AMeX method to prepare sliced tissue specimens. The tissue specimens were subjected to HE staining. Results are shown in FIG. 7. HCT116 showed no hierarchical structure, suggesting that HCT116 is cancer-forming cells.

(5) Detection of Normal Intestinal Stem Cell Marker LGR5 Protein

RIPA buffer was used to prepare HCT116 cell lysate for SDS-PAGE and Western blotting. Rabbit mAb to human GPR49 was used to detect LGR5 protein. Mouse mAb to human GAPDH was used as a positive control. Results are shown in FIG. 8. No LGR5 protein was detected in HCT116.

(6) Detection of Cells Positive for Normal Intestinal Stem Cell Marker LGR5

Figure 9:
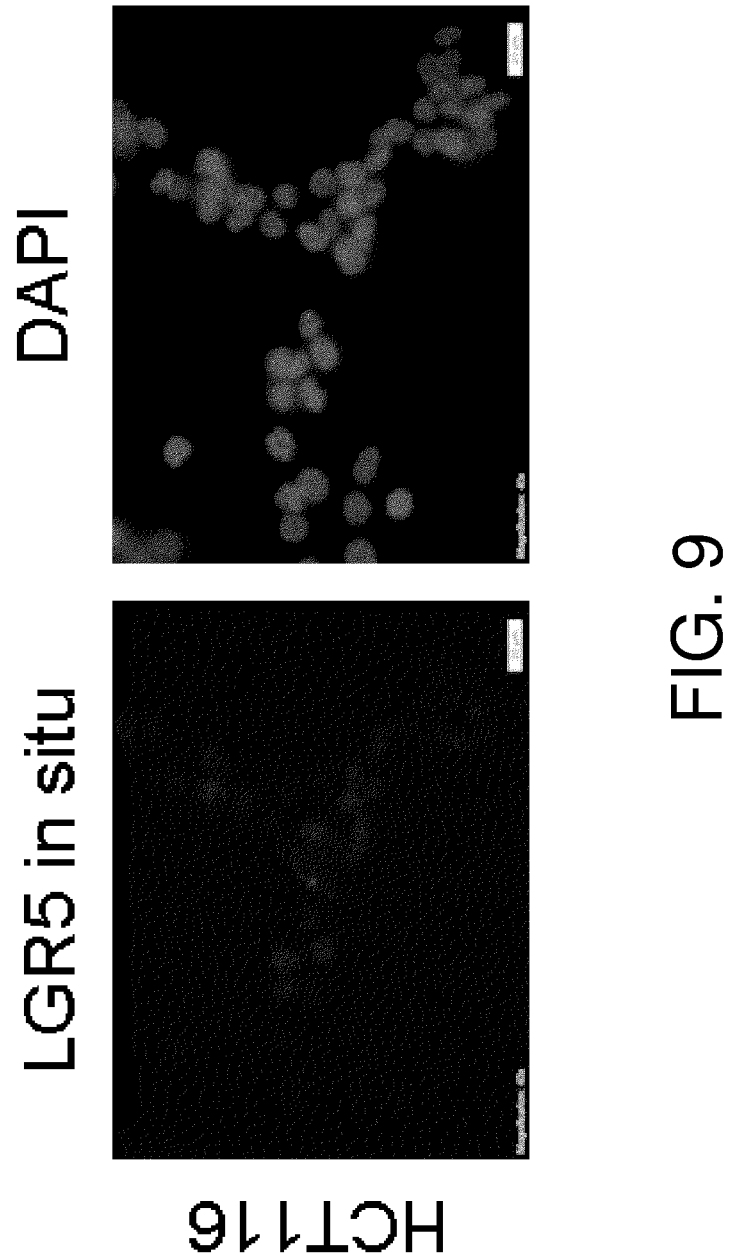
FIG. 9 presents a photograph showing LGR5-positive cells by in situ hybridization. The commercially available colon cancer line HCT116 showed no LGR5-positive cells.

HCT116 was plated and cultured at 5,000 cells/well on Lab-Tek Chamber Slides (Thermo Scientific, Cat. No. 177402). After about 24 hours, the slides were used for in situ hybridization. In situ hybridization analysis was conducted using the QuantiGene ViewRNA Plate-Based Assay Kit (Panomics, Cat. No. QVP0010), QuantiGene ViewRNA Plate-Based Signal Amplification Kit (Panomics, Cat. No. QVP0200), and QuantaGene ViewRNA GPR49 (LGR5) Probe set (Panomics, Cat. No. VA1-10587) according to the manufacturer's recommended procedures. DAPI (Invitrogen, Cat. No. D21490) was used for nuclear staining. Results are shown in FIG. 9. No HCT116 cells were confirmed to be positive for the LGR5 probe.

[Example 3] In Vitro Establishment of Cancer Stem Cells (1) In Vitro Adherent Culture of Cancer Stem Cells (Hereinafter Simply Referred to as Adherent Culture in Some Cases)

Figure 10:
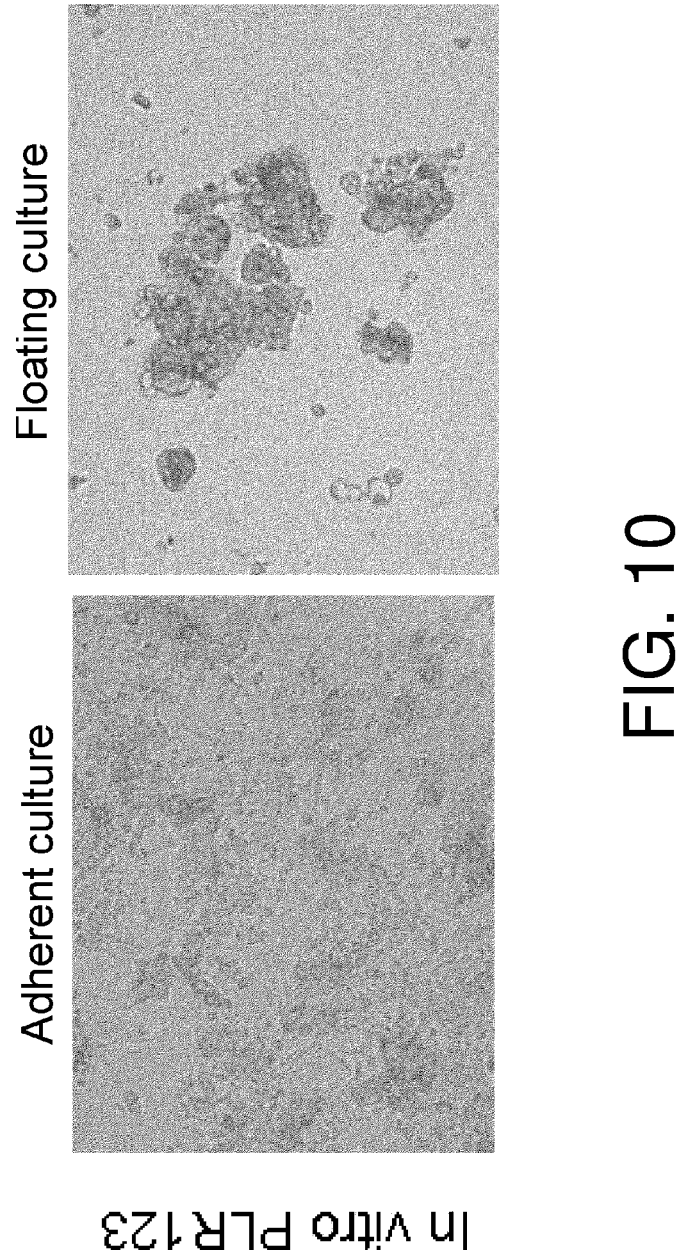
FIG. 10 presents a photograph showing the morphology of the moderately differentiated colon cancer line PLR123 cultured in vitro. A cell mass called spheroid was formed only in a floating state.

Cells were cultured based on a standard method (e.g., at 37° C. and in the presence of 5% $CO_2$) in a stem cell medium described below. The stem cell medium was prepared by supplementing DMEM/F12 (Invitrogen, Cat. No. 11330057) medium with 1×N-2 supplement (Invitrogen, Cat. No. 17502014), 20 ng/mL Recombinant Human EGF (Invitrogen, Cat. No. 11330032), 10 ng/mL Fibroblast Growth Factor-basic Human Recombinant (Sigma, Cat. No. F0291), 4 µg/mL Heparin Sodium Salt (Sigma, Cat. No. H3149), 4 mg/mL AlbuMax Lipid Rich BSA (Invitrogen, Cat. No. 11010021), 20 µg/mL insulin, Human Recombinant, Zinc solution (Invitrogen, Cat. No. 12585014), 2.9 mg/mL D-(+)-Glucose Solution (45%) (Sigma, Cat. No. G8769), and 1× Antibiotic-Antimycotic (Invitrogen, Cat. No. 15240062) at their final concentrations. Cancer cells containing cancer stem cells were cultured using the stem cell medium in a 6-well plate for adherent culture (BD, Cat. No. 353046). Several days later, cells that adhered to the plate and floating cells were observed. The floating cells were removed, and only the adherent cells were cultured. Adherent cells grown to confluence were detached with Accutase and cultured in a new 6-well plate for adherent culture, or T25 (BD, Cat. No. 353109), T75 (BD, Cat. No. 356485), and T150 (BD, Cat. No. 355001) flasks for adherent culture. Passage of the adherent cells was continued until all the cells became positive for cancer stem cell markers as described in (2) below. Some of the cells were suspended in a cell storage solution, Bambanker (Wako, Cat. No. 302-14681), and stored at −80° C. or below. Morphology of the moderately differentiated colon cancer line PLR123 cultured in vitro is shown in FIG. 10. A cell mass called spheroid was formed only in a floating state.

(2) Detection of Cancer Stem Cell Marker-Positive Cells

The cancer cells adherently cultured in vitro in the stem cell medium were detached from the flask with Accutase, suspended in FACS buffer, and allowed to react at 4° C. for 30 minutes with the 7-AAD Viability Dye for staining dead cells, or as a cancer stem cell marker, FITC-labeled mouse mAb to human CD326 (EpCAM), PE-labeled mouse mAb to human CD133/1 (AC133), or PE-labeled mouse mAb to human CD44. Subsequently, the cells were washed once with FACS buffer and subjected to flow cytometric analysis. Aldehyde dehydrogenase (ALDH) activity was detected using the AldeFluor Kit according to the manufacturer's recommended procedures. EPICS ALTRA was used for flow cytometric analysis to analyze cancer stem cell markers in 7-AAD Viability Dye-negative cells. Results are shown in FIG. 11. The moderately differentiated colon cancer lines PLR123 and PLR59 adherently cultured in vitro were all positive for the cancer stem cell markers, suggesting homogeneous cell populations.

(3) Detection of Normal Intestinal Stem Cell Marker LGR5 Protein

Figure 12:
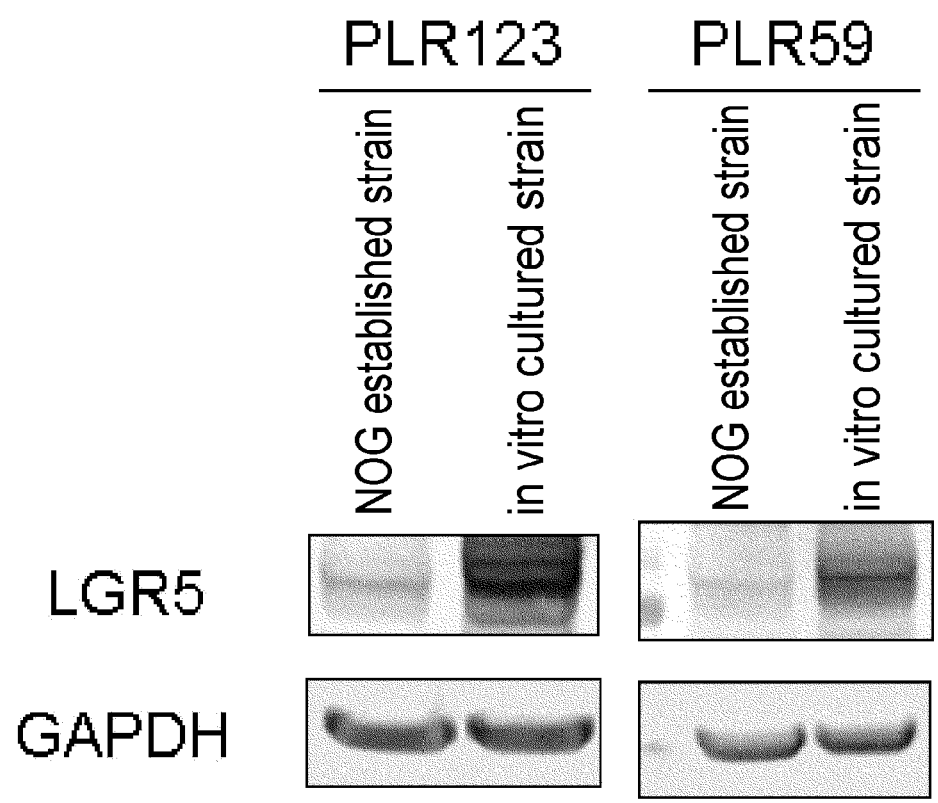
FIG. 12 shows LGR5 protein expression by Western blotting. Increase of the LGR5 protein was detected in the moderately differentiated colon cancer lines that were adherently cultured in vitro in a stem cell medium. This suggests that the normal intestinal stem cell marker-positive cells were concentrated by in vitro culture in a stem cell medium.

After mouse cells were removed from the cell solution, RIPA buffer was used to prepare lysates for the moderately differentiated colon cancer lines PLR123 and PLR59, colon cancer line PLR123 adherently cultured in vitro in the stem cell medium, and colon cancer line PLR59 adherently cultured in vitro in the stem cell medium for SDS-PAGE and Western blotting. Rabbit mAb to human GPR49 was used to detect LGR5 protein. Mouse mAb to human GAPDH was used as a positive control. Results are shown in FIG. 12. Increase of the LGR5 protein was detected in the colon cancer lines that were adherently cultured in the stem cell medium in vitro. Thus, the normal intestinal stem cell marker-positive cells were concentrated by in vitro culture in the stem cell medium.

(4) Detection of Normal Intestinal Stem Cell Marker LGR5-Positive Cells

Figure 13:
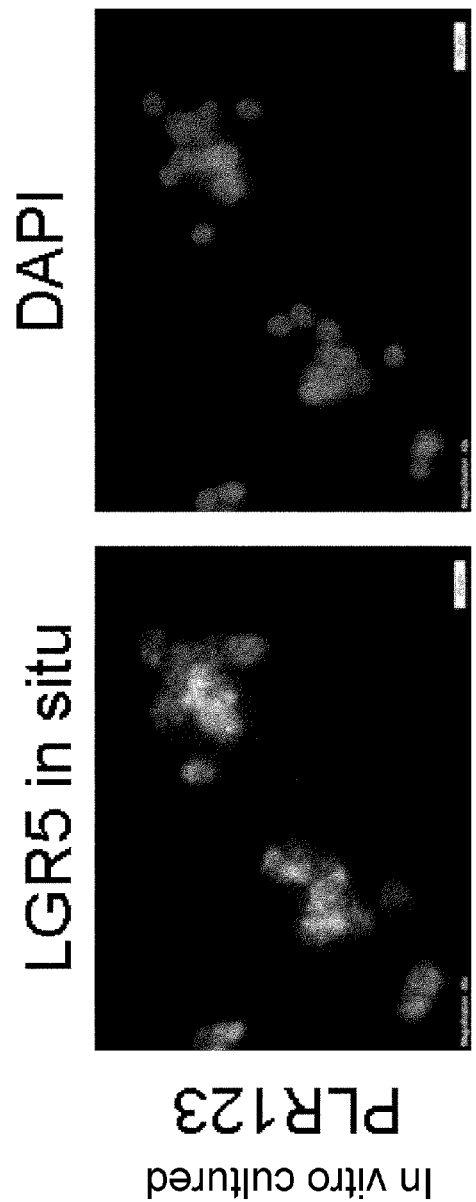
FIG. 13 presents a photograph showing LGR5-positive cells by in situ hybridization. The moderately differentiated colon cancer line PLR123 that was adherently cultured in vitro in a stem cell medium was all positive for the LGR5 probe. Thus, the normal intestinal stem cell marker-positive cells were concentrated by in vitro culture in a stem cell medium, suggesting that all the cells were homogeneous cells positive for the normal intestinal stem cell marker LGR5.

The moderately differentiated colon cancer line PLR123 that was adherently cultured in the stem cell medium in vitro was plated and cultured at 50,000 cells/well on Lab-Tek Chamber Slides. After about 24 hours, the slides were used for in situ hybridization. In situ hybridization analysis was conducted using the QuantiGene ViewRNA Plate-Based Assay Kit, QuantiGene ViewRNA Plate-Based Signal Amplification Kit, and QuantaGene ViewRNA GPR49 (LGR5) Probe set according to the manufacturer's recommend procedures. DAPI was used for nuclear staining. Results are shown in FIG. 13. The moderately differentiated colon cancer line PLR123 that was adherently cultured in the stem cell medium in vitro was confirmed to be all positive for the LGR5 probe. It was demonstrated that the normal intestinal stem cell marker-positive cells were concentrated by in vitro culture in the stem cell medium, suggesting that all the cells were homogeneous cells positive for the normal intestinal stem cell marker LGR5.

(5) Cancer Formation Test of In Vitro Adherently Cultured Cells

The cancer cells adherently cultured in vitro were detached from the flask with Accutase and washed with DPBS several times. The cell solution was passed through a 40 µm cell strainer. The cells were confirmed microscopically to be single cells, and then counted. Matrigel Basement Membrane Matrix, diluted to 50% with Hank's Balanced Salt Solution, was used to prepare 10,000, 1,000, or 100 cells/mL solutions. Each cell solution was subcutaneously transplanted into NOG mice at 100 µL/spot, i.e., 1,000, 100, and 10 cells/spot to evaluate the number of tumors formed. Results are shown in Table 3. The moderately differentiated colon cancer lines PLR123 and PLR59 that were adherently cultured in vitro all formed cancer when transplanted. This demonstrated that the moderately differentiated colon cancer lines PLR123 and PLR59 that were adherently cultured in vitro had cancer-forming ability.

TABLE 3

| Name of cells | Days after transplantation | Cancer formation ratio | | | Frequency |
| --- | --- | --- | --- | --- | --- |
| | | 1,000 cells | 100 cells | 10 cells | |
| PLR123 adherently cultured in vitro | 35 days | 6/6 | 6/6 | 6/6 | 1 |
| PLR59 adherently cultured in vitro | 46 days | 6/6 | 6/6 | 6/6 | 1 |

(6) Evaluation of Cancer Stem Cells Established In Vitro

For comparison of cancer-forming ability, the moderately differentiated colon cancer line PLR123 that was adherently cultured in vitro was cultured for one additional month or longer. The cancer cells adherently cultured in vitro were detached from the flask with Accutase, and suspended with DPBS several times. The cell solution was passed through a 40-μm cell strainer. The cells were confirmed microscopically to be single cells, and then counted. Matrigel Basement Membrane Matrix, diluted to 50% with Hank's Balanced Salt Solution, was used to prepare 10,000, 1,000, or 100 cells/mL solutions. Each cell solution was subcutaneously transplanted into NOG mice at 100 μL/spot, i.e., 1,000, 100, and 10 cells/spot to evaluate the number of tumors formed. Results are shown in Table 4. The moderately differentiated colon cancer line PLR123 that had been cultured for one month or longer all formed cancer when transplanted. Thus, the cancer forming ability was maintained at 100% in the in vitro culture, and cancer stem cells were successfully established in vitro.

(8) Analysis of Cancer Stem Cell Markers in Cells Prepared from Human Cancer Cell Masses Formed from 10 Cancer Cells Adherently Cultured In Vitro Cells prepared from cancer cell masses formed from 10 cells of the moderately differentiated colon cancer lines PLR123 and PLR59 that were adherently cultured in vitro were suspended in FACS buffer, and allowed to react at 4° C. for 30 minutes after the addition of Rat mAb to mouse MHC class I. The cells were washed once with FACS buffer, and allowed to react at 4° C. for 30 minutes with PE-labeled goat Ab to rat IgG2a or APC-labeled goat Ab to rat IgG2a as a secondary antibody, the 7-AAD Viability Dye for staining dead cells, or as a cancer stem cell marker, FITC-labeled mouse mAb to human CD326 (EpCAM), PE-labeled mouse mAb to human CD133/1 (AC133), or PE-labeled mouse mAb to human CD44. Subsequently, the cells were washed once with FACS buffer and subjected to flow cytometric analysis. Aldehyde dehydrogenase (ALDH) activity was detected using the AldeFluor Kit according to the manufacturer's recommended procedures. EPICS ALTRA was used for flow cytometric analysis to analyze cancer stem cell markers in mouse MHC class I- and 7-AAD Viability Dye-negative cells. Results are shown in FIG. 15. In cancer cell masses formed from 10 cells of the moderately differentiated colon cancer lines PLR123 and PLR59 that were adherently cultured in vitro, cancer stem cell marker-negative cells were observed, suggesting that cancer stem cell marker-negative cells were generated from cancer stem cell marker-positive cells.

(9) Cancer Formation Test of Cells (Second Generation) Prepared from a Human Cancer Cell Mass (First Generation) Formed from 10 Adherently Cultured In Vitro Cancer Cells

TABLE 4

| Name of cells | Days after transplantation | Cancer formation ratio | | | Frequency | |
| --- | --- | --- | --- | --- | --- | --- |
| | | 1000 cells | 100 cells | 10 cells | | |
| PLR123 adherently cultured in vitro Date of transplantation: 20100603 | 35 days | 6/6 | 6/6 | 6/6 | 1 | Cultured for 35 days |
| PLR123 adherently cultured in vitro Date of transplantation: 20100708 | 39 days | 6/6 | 6/6 | 6/6 | 1 | |

Figure 14:
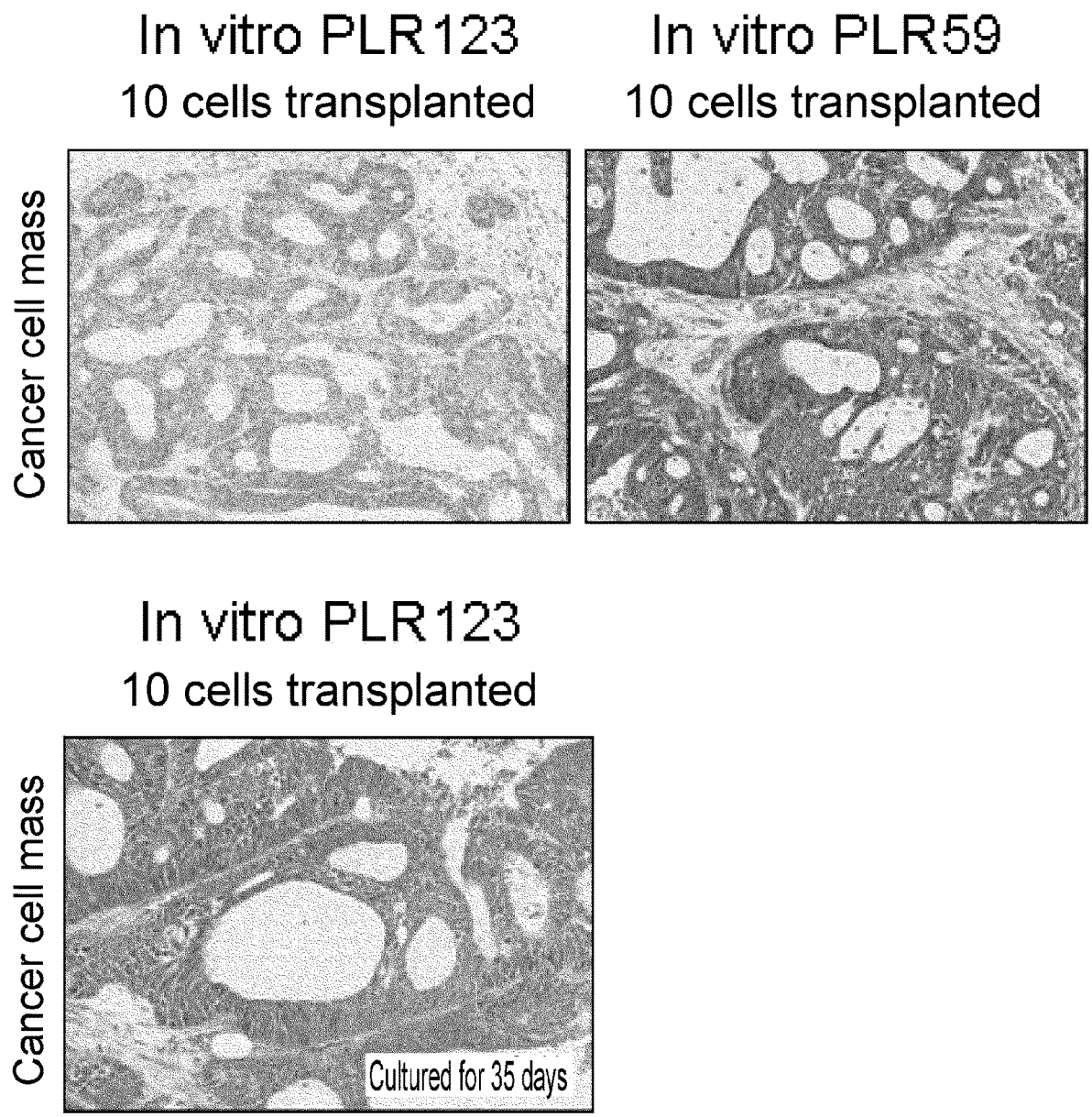
FIG. 14 presents a photograph showing an HE-stained tissue specimen. In cancer cell masses formed from 10 cells of the moderately differentiated colon cancer lines PLR123 and PLR59 adherently cultured in vitro, a hierarchical structure similar to those of human tissues and NOG established cancer cell lines was observed. Also, in a cancer cell mass formed from the moderately differentiated colon cancer line PLR123 adherently cultured in vitro for one month or longer, a hierarchical structure similar to those of human tissues and NOG established cancer cell lines was observed. Thus, the moderately differentiated colon cancer lines PLR123 and PLR59 that were adherently cultured in vitro were all cancer stem cells with pluripotency.

(7) Histological Evaluation of Hierarchical Structure Formation in Cancer Cell Masses Formed from 10 Cancer Cells Adherently Cultured In Vitro The cancer cell masses formed from 10 cells of the moderately differentiated colon cancer lines PLR123 and PLR59 that were adherently cultured in vitro were excised, fixed for 16-24 hours in 4% paraformaldehyde at 4° C., and embedded by the AMeX method to prepare sliced tissue specimens. The tissue specimens were subjected to HE staining. Results are shown in FIG. 14. In cancer cell masses formed from 10 cells of the moderately differentiated colon cancer lines PLR123 and PLR59 that were adherently cultured in vitro, a hierarchical structure similar to those of human tissues and established cancer cell lines was observed. Also, in a cancer cell mass formed from the moderately differentiated colon cancer line PLR123 that was adherently cultured in vitro for one month or longer, a hierarchical structure similar to those of human tissues and NOG established cancer cell lines was observed. Thus, the moderately differentiated colon cancer lines PLR123 and PLR59 that were adherently cultured in vitro were all cancer stem cells with pluripotency.

After mouse cells were removed from a cell solution prepared with the cancer cell mass (first generation) formed from 10 cells of the moderately differentiated colon cancer line PLR123 that was adherently cultured in vitro, the human cancer cells were confirmed microscopically to be single cells, and then counted. Matrigel Basement Membrane Matrix, diluted to 50% with Hank's Balanced Salt Solution, was used to prepare 10,000, 1,000, or 100 cells/mL solutions. Each cell solution was subcutaneously transplanted into NOG mice at 100 μL/spot, i.e., 1,000, 100, and 10 cells/spot to evaluate morphology and the number of tumors formed. Results are shown in Table 5. Cancer having a hierarchical structure was formed at 10 or more spots, suggesting that cells contained in the cancer cell mass had self-replicating ability as cancer stem cells. The ratio of cancer stem cells contained in the cancer cell mass was 1/95, suggesting that differentiated cells with no cancer-forming ability were generated from cancer stem cells adherently cultured in vitro.

TABLE 5

| Name of cells | Days after transplantation | Cancer formation ratio | | | Frequency |
| --- | --- | --- | --- | --- | --- |
| | | 1,000 cells | 100 cells | 10 cells | |
| PLR123 adherently cultured in vitro First generation | 45 days | 6/6 | 3/6 | 2/6 | 1/95 |

Figure 16:
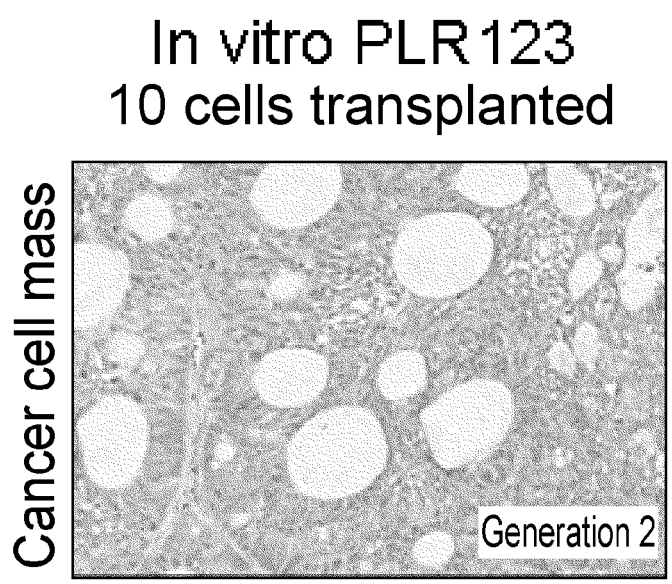
FIG. 16 presents a photograph showing an HE-stained tissue specimen. In a second-generation cancer cell mass formed from the moderately differentiated colon cancer line PLR123 adherently cultured in vitro, a hierarchical structure similar to those of human tissues and the original cancer cell line was observed.

(10) Histological Evaluation of Hierarchical Structure Formation in a Second-Generation Cancer Cell Mass Formed from Cancer Cells Adherently Cultured In Vitro A second-generation cancer cell mass formed from cancer cells adherently cultured in vitro were excised, fixed for 16-24 hours in 4% paraformaldehyde at 4° C., and embedded by the AMeX method to prepare sliced tissue specimens. The tissue specimens were subjected to HE staining. Results are shown in FIG. 16. In the second-generation cancer cell mass formed from the moderately differentiated colon cancer line PLR123 that was adherently cultured in vitro, a hierarchical structure similar to those of human tissues and NOG established cancer cell lines was observed.

[Reference Example 1] Lgr5 Protein Expression Analysis (1) Establishment of Cells Expressing Full-Length Human Lgr4, Lgr5, or Lgr6

Full-length human Lgr4, Lgr5, and Lgr6 cDNAs were cloned by PCR based on the sequences of NM_018490 (Lgr4), NM_001017403 (Lgr5), and NM_003667 (Lgr6). The cloned genes were expressed with or without the addition of an HA tag at the N terminus. The expression plasmids were transfected into the Chinese hamster ovary cell line CHO DG44 (Invitrogen) using Gene Pulser (Bio-Rad). Stable cell lines, HA-Lgr4/DG, HA-Lgr5/DG, and HA-Lgr6/DG, were selected using G418.

(2) Preparation of Soluble Lgr5-Fc Protein

Soluble Lgr5 (amino acids 1-555) protein was expressed as a fusion protein with the Fc portion of mouse IgG2a of CHO DG44. Transfectants were screened by sandwich ELISA using goat anti-mouse IgG2a (Bethyl labotratories) and HRP rat anti-mouse IgG2amAb (Serotec). The clone that produced the largest amount of sLgr5-Fc was named 2D3. The culture supernatant of 2D3 was collected for affinity purification of the Lgr5-Fc protein on a Protein A-Sepharose column (Pharmacia). Lgr5-Fc served as an antigen for protein immunization and ELISA screening.

(3) Production of Anti-Lgr5 Monoclonal Antibody by Immunization with the Lgr5-Fc Protein (WO2009063970)

Balb/c mice (Charles River Japan) were subcutaneously immunized with 50 μg of Lgr5-Fc emulsified in complete Freund's adjuvant. Two weeks later, weekly injection was repeated for two weeks using the same amount in Freund's incomplete adjuvant. Three days before cell fusion, 25 μg of Lgr5Fc was intravenously injected into mice. Spleen lymphocytes derived from immunized mice were fused with P3-X63Ag8U1 mouse myeloma cells (ATCC) by the conventional method (Kremer L and Marquez G (2004) Methods Mol. Biol., 239, 243-260). Hybridoma culture supernatants were screened using ELISA for antibodies that show reactivity with sLgr5-Fc. Lgr5-specific mouse mAbs, 2T15E-2 and 2U2E-2, were established.

(4) Immunofluorescence Staining of Cultured Cells and Xenograft Tissue

For immunofluorescence cytochemistry, the cells fixed with 4% paraformaldehyde and methanol were incubated with a mouse anti-human E-cadherin (Abcam), rabbit anti-human Snail (Abcam), or rabbit anti-human β-catenin (Sigma) antibody, followed by visualization using an AlexaFluor 488-labeled goat anti-mouse or -rabbit IgG antibody, respectively. For immunofluorescence histochemistry, slices from paraffin blocks of the above xenograft tumor were incubated with a mouse anti-human Lgr5 (2U2E-2) or rabbit anti-human Snail (Abcam) antibody. After incubation with a primary antibody, Lgr5 protein was detected using a goat anti-mouse antibody coupled with polymer-HRP (DAKO), followed by visualization with AlexaFluor 488-labeled tyramide (Invitrogen). Snail protein was detected with a biotinylated goat anti-rabbit antibody (VECTOR), followed by visualization with AlexaFluor 568-labelled streptavidin (Invitrogen). These cells and samples were also stained with DAPI (Invitrogen).

(5) Flow Cytometric Analysis

CSC was incubated with a labeled antibody and analyzed using EPICS ALTRA (Beckman Coulter) and FACSCalibur (Becton Dickinson). The antibodies used were PE-labeled mouse anti-human CD133 (Miltenyi Biotec), PE-labeled mouse anti-human CD44 (BD Pharmingen), FITC-labeled mouse anti-human CD326 (EpCAM) (Miltenyi Biotec), PE-labeled mouse anti-human CD166 (R & D Systems), PE-labeled mouse anti-human CD24 (BD Pharmingen), PE-labeled mouse anti-human CD26 (BD Pharmingen), and PE-labeled mouse anti-human CD29 (BD Pharmingen) antibodies.

Subsequently, the CSC was incubated with a mouse anti-human Lgr5 antibody (2T15E-2) and then a PR-labeled rat anti-mouse IgG (Invitrogen) antibody for Lgr5 staining. Aldehyde dehydrogenase activity was measured using the AldeFluor Kit (Stemcell Technologies). Mouse cells and human CSC were distinguished by staining with an anti-mouse MHC class I antibody (Abcam) and a PE- or APC-labeled goat anti-human IgG2a (BioLegend) antibody. Dead cells were removed with the 7-AAD Viability Dye (Beckman Coulter).

Figure 18:
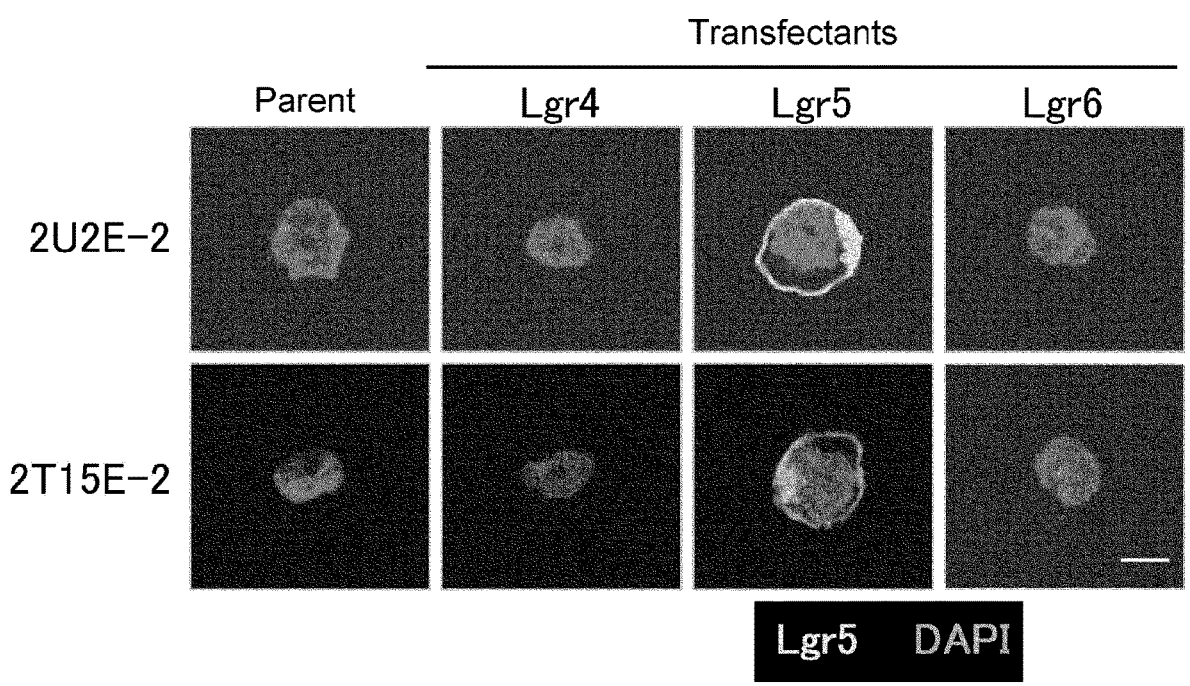
FIG. 18 presents a photograph showing results on the specificities of anti-human Lgr5 monoclonal antibodies (mAbs), 2U2E-2 and 2T15E-2, as demonstrated by the immunofluorescence microscopic observations of DG44 cells transfected with Lgr4, Lgr5, or Lgr6 cDNA. Non-transfected parent cells and transfectants were fixed and treated with 5 µg/mL antibody. Strong fluorescence (green signal on the right) was observed in the Lgr5 cDNA-containing cells, but not in the parental and Lgr4 or Lgr6 cDNA-containing cells. The scale bar indicates 5 µm.
Figure 19:
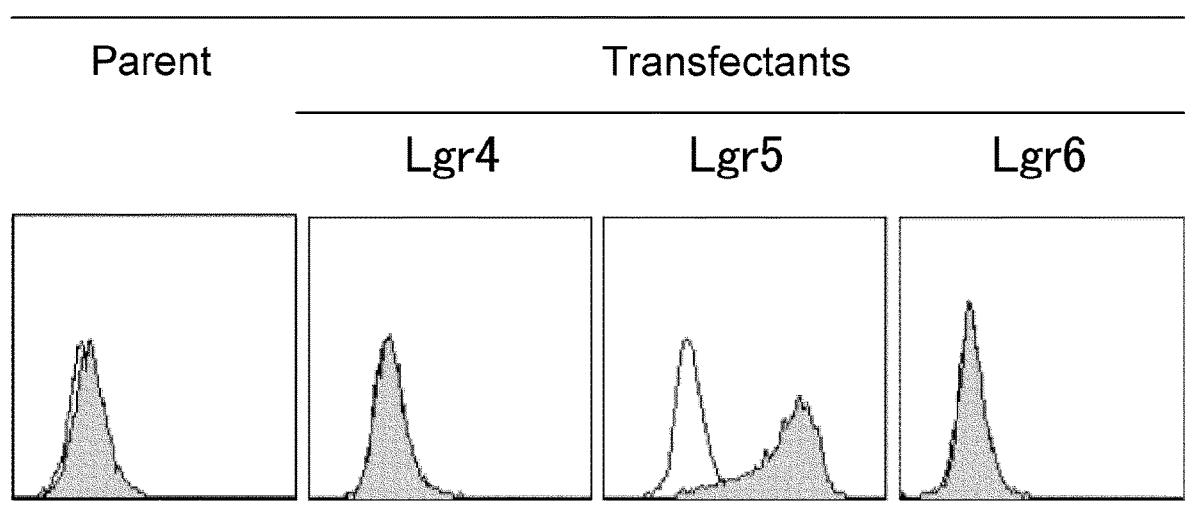
FIG. 19 shows results on the specificity of anti-human Lgr5 monoclonal antibody (mAb), 2T15E-2, as demonstrated by the flow cytometry of DG44 cells transfected with Lgr4, Lgr5, or Lgr6 cDNA. Non-transfected parent cells and transfectants were incubated with the 2T15E-2 monoclonal antibody and analyzed by FACS. The 2T15E-2 antibody reacted with the Lgr5 cDNA-containing cells, but did not with the parental and Lgr4 or Lgr6 cDNA-containing cells. Lgr4, Lgr5, and Lgr6 expressions in the transfectants were confirmed by Western blot analysis.

These antibodies were highly specific to Lgr5, but they did not cross-react with Lgr4 and 6 which both have high homology to Lgr5 (FIGS. 18 and 19). The inventors used these antibodies to demonstrate Lgr5 expression in the adherent cancer stem cells.

[Reference Example 2] Tumor Reconstruction Ability of Lgr5-Positive and -Negative Colon CSC If a characteristic of colon cancer stem cell populations is Wnt signaling, only Lgr5-positive adherent cells can form tumors in vivo. To examine this, the inventors investigated the tumorigenicity of Lgr5-positive adherent cells and Lgr5-negative floating cells.

As a result, tumorigenicity was higher in Lgr5-positive adherent cells than in Lgr5-negative floating cells. Both Lgr5-positive and -negative cells retained tumorigenicity in NOG mice. Subcutaneous injection of 10 Lgr5-positive cells formed tumors at all the injection sites (6 of 6 sites). Tumors were formed at 2 sites (PLR123-derived cells) and 1 site (PLR59-derived cells) of the 6 sites injected with Lgr5-negative cells (Table 6).

TABLE 6

| Cell line* | Specimen† | Number of cells per injection site | | |
|---|---|---|---|---|
| | | 1,000 | 100 | 10 |
| PLR59 | Primary | 12⁺/12‡ (100) | 5/12 (42) | 0/12 (0) |
| | Floating (Lgr5⁻) | 6/6 (100) | 6/6 (100) | 1/6 (17) |
| | Adherent (Lgr5⁺) | 6/6 (100) | 6/6 (100) | 6/6 (100) |
| PLR123 | Primary | 12/12 (100) | 5/12 (42) | 0/12 (0) |
| | Floating (Lgr5⁻) | 6/6 (100) | 5/6 (83) | 2/6 (33) |
| | Adherent (Lgr5⁺) | 6/6 (100) | 6/6 (100) | 6/6 (100) |

Figure 20:
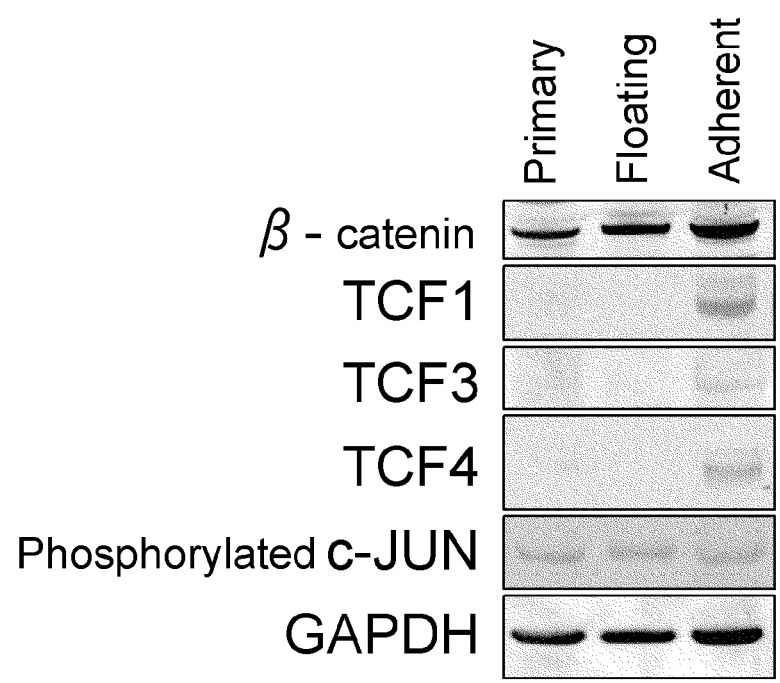
FIG. 20 presents a photograph showing results of the Western blot analysis of β-catenin, TCF1, TCF3, TCF4, and phosphorylated c-JUN protein in the primary cells, floating cancer stem cells, and adherent cancer stem cells of PLR123 cells. All the protein expressions were up-regulated in Lgr5-positive adherent cancer stem cells as compared with those of the primary cells. GAPDH was also visualized as a reference protein for protein loading.
Figure 21:
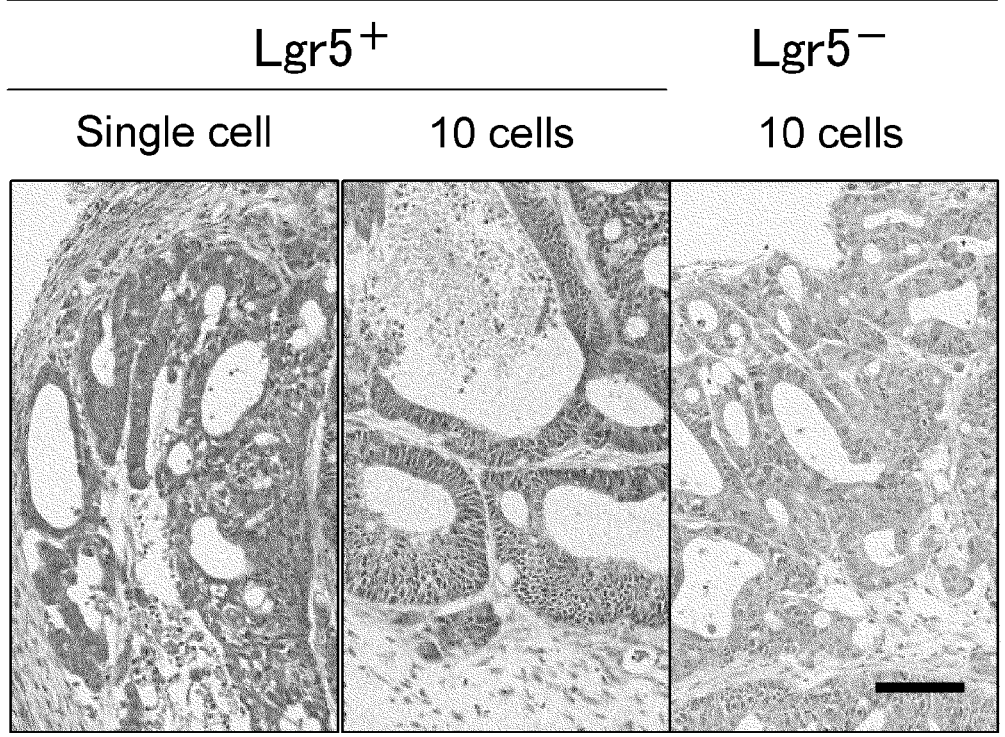
FIG. 21 presents a photograph showing results of the histopathology of xenograft tumors derived from one and ten PLR123-derived Lgr5-positive cell(s) as well as ten PLR123-derived Lgr5-negative cells. All the tumors showed a hierarchical structure with histopathological properties similar to those of the original tumors. The scale bar indicates 100 µm.
Figure 22:
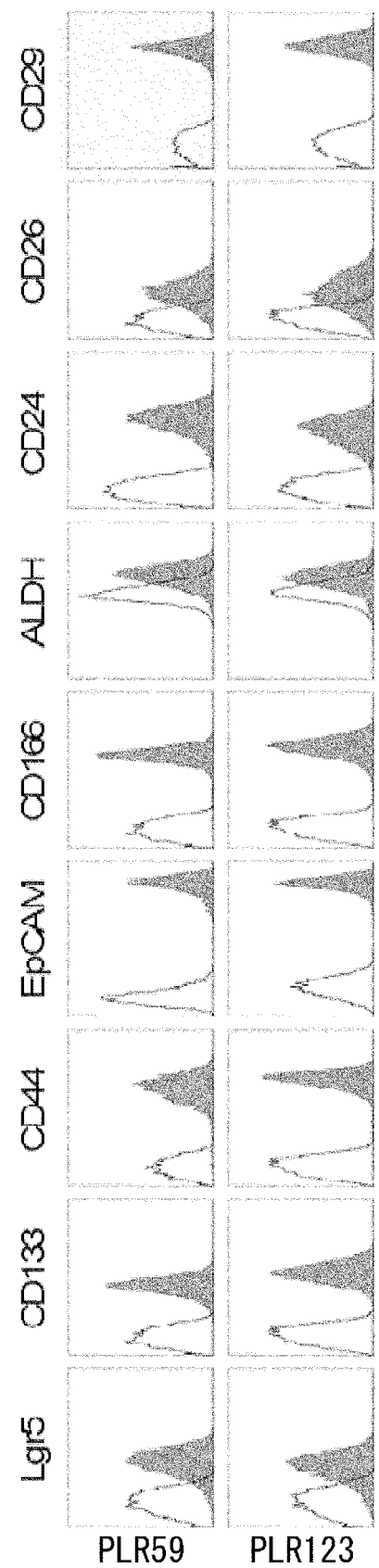
FIG. 22 shows results of the flow cytometric analysis of the reported cancer stem cell markers in adherent stem cells derived from PLR59 or PLR123 xenografts cultured for one month. Even after one month of culture in vitro, both adherent cancer stem cells derived from PLR59 or PLR123 were positive for all the cancer stem cell markers reported. The gray indicates fluorescence intensity or ALDH activity after staining cells with the indicated antibodies, while the white indicates fluorescence intensity after staining cells with a control isotype antibody or treating cells with the ALDH activity by an ALDH inhibitor.

For Lgr5-positive cells, of the 12 injection sites in which only a single cell was injected per site, 2 sites (PLR123-derived cells) and 1 site (PLR59-derived cells) had tumor reconstruction (FIG. 20). Tumors derived from Lgr5-positive and -negative cells showed almost the same histopathological features as the original ones (FIG. 21). In addition, the cell surface marker expression and tumorigenicity of Lgr5-positive CSC showed no change even after 1 month of subculture (FIGS. 22 and 23).

These results demonstrate that Lgr5-positive and -negative cells derived from PLR59 and PLR123 are high-purity colon CSC, and that Lgr5-positive and -negative cells represent two different states of CSC in colon cancer.

[Reference Example 3] Effects of TCF and β-Catenin

Western blot analysis was conducted as described below. Proteins were extracted using RIPA buffer (Sigma) supplemented with Complete Mini Protease Inhibitor Cocktail (Roche). Proteins were fractionated in a NuPAGE gel (Invitrogen) and transferred onto a PVDF membrane. After blocking with PBS containing 1% skim milk, the membrane was probed with a rabbit anti-human β-catenin (Sigma), rabbit anti-human phospho c-JUN (Sigma), rabbit anti-human TCF1 (Cell Signaling), rabbit anti-human TCF3 (Cell Signaling), rabbit anti-human TCF4 (Cell Signaling), rabbit anti-human Lgr5 (Abcam), mouse anti-human E-cadherin (Abcam), rabbit anti-human Snail (Abcam), or mouse anti-human GAPDH (Santa Cruz) antibody. Reactive bands were detected using the BCIP/NBT substrate (KPL).

Figure 24:
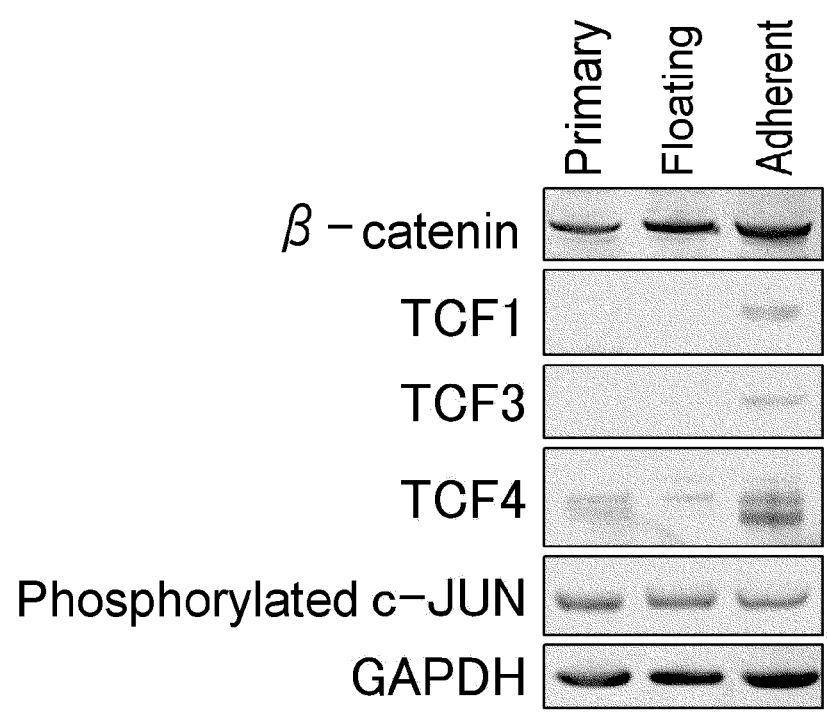
FIG. 24 presents a photograph showing results of the Western blot analysis of β-catenin, TCF1, TCF3, TCF4, and phosphorylated c-JUN protein in the primary cells, floating cancer stem cells, and adherent cancer stem cells of PLR59. All the protein expressions were up-regulated in Lgr5-positive adherent cancer stem cells as compared with those of the primary cells. GAPDH was also visualized as a reference for protein loading.

Consistent with the Lgr5 expression, protein levels of β-catenin, TCF1, TCF3, and TCF4 were up-regulated in Lgr5-positive cells, but not in Lgr5-negative cells (FIGS. 20 and 24).

Phosphorylation of c-Jun at the N-terminal region was not detected in Lgr5-positive cancer stem cells as compared with Lgr5-negative cancer stem cells (FIGS. 20 and 24).

To determine whether or not the Wnt signaling promotes the growth of colon cancer stem cells, the inventors examined the effects of FH535 (β-catenin/TCF inhibitor) and cardamonin (Wnt/β-catenin inhibitor that induces β-catenin degradation) on the growth of colon cancer stem cells. Cell growth was evaluated as described below. Floating and adherent cancer stem cells were seeded at about 100 and $1 \times 10^4$ cells per well, respectively, in 96-well plates. On days 0 and 3, living cells were counted using the Cell Counting Kit-8 assay (Doujindo) according to the manufacturer's protocol. The average absorbance on day 0 was expressed as 100%. For chemical sensitivity analysis, floating and adherent cancer stem cells were seeded at about 100 and $1 \times 10^4$ cells per well in 96-well plates, respectively. After 24-hour incubation, 10 µg/mL 5-FU (Hospira), 10 µg/mL irinotecan (Hospira), 50 mM TCF inhibitor FH535 (Merck), or 50 mM β-catenin inhibitor cardamonin (Merck) was added. After 3-day culture in the presence of a drug, Cell Counting Kit-8 was added to the cells. The average absorbance of cells exposed to DMSO or the medium alone was expressed as 100%. All the experiments were conducted in triplicate.

Figure 25:
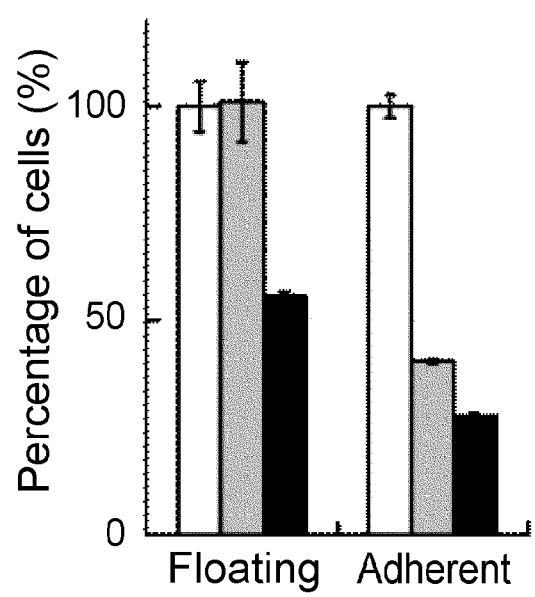
FIG. 25 shows growth inhibition of Lgr5-positive adherent cancer stem cells by FH535 (50 µM) or cardamonin (50 µM) in PLR123 cells. The number of living cells after three days of culturing together with FH535 (gray column) or cardamonin (black column) is expressed as a percentage relative to the number for DMSO alone (white column). The results are the mean values of three experiments. The bars at the top of each column show the standard deviations.
Figure 26:
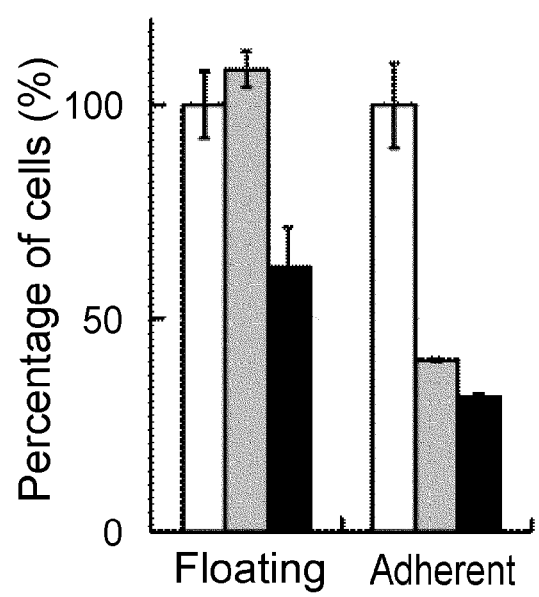
FIG. 26 shows growth inhibition of Lgr5-positive adherent cancer stem cells by FH535 (50 µM) or cardamonin (50 µM) in PLR59 cells. The number of living cells after three days of culturing together with FH535 (gray column) or cardamonin (black column) is expressed as a percentage relative to the number for day 0 (white column).

As a result, 50 µM FH535 significantly reduced the growth of Lgr5-positive colon cancer stem cells, but had no effect on the growth of Lgr5-negative colon cancer stem cells (FIGS. 25 and 26). On the other hand, 50 µM cardamonin reduced the number of living cells to 70% in Lgr5-positive colon cancer stem cells and to about 50% in Lgr5-negative colon cancer stem cells (FIGS. 25 and 26).

Figure 27:
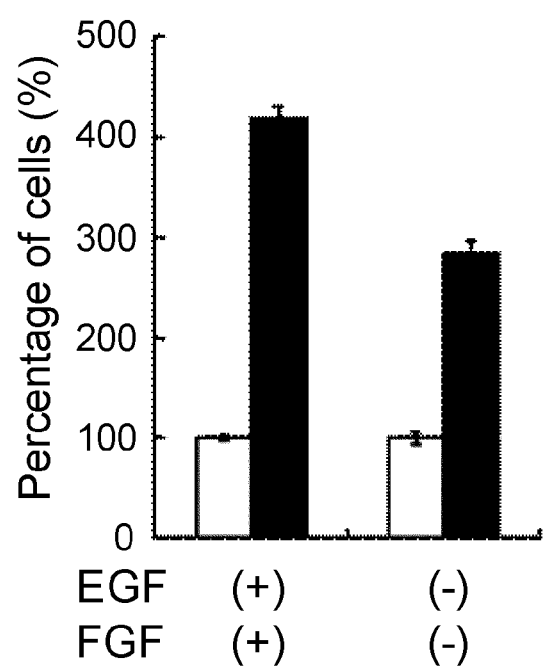
FIG. 27 shows the growth of PLR123 cells in the presence or absence of EGF and FGF. Adherent cancer stem cells were cultured for three days in the presence or absence (black column). The number of living cells is shown as percentage relative to the number for day 0 (white column). The results are the mean values of three experiments. The bars at the top of each column show the standard deviations.
Figure 28:
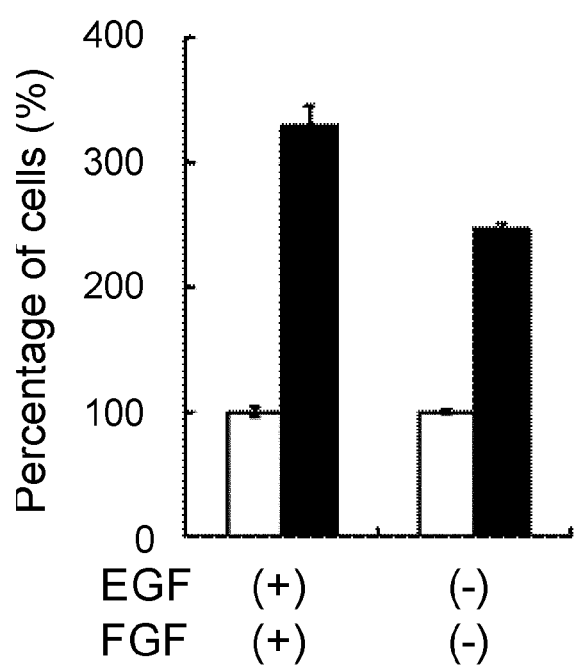
FIG. 28 shows the growth of PLR59 cells in the presence or absence of EGF and FGF. Adherent cancer stem cells were cultured for three days in the presence or absence (black column). The number of living cells is shown as a percentage relative to the number for day 0 (white column).

These results suggest that TCF mediates the growth of Lgr5-positive cells and that β-catenin is involved in the survival of colon cancer stem cells. Interestingly, Lgr5-positive cells grew even without the supplementation of EGF and FGF (FIGS. 27 and 28), suggesting that colon cancer stem cells have an endogenous autocrine mechanism to activate Wnt signaling for their growth.

Figure 29:
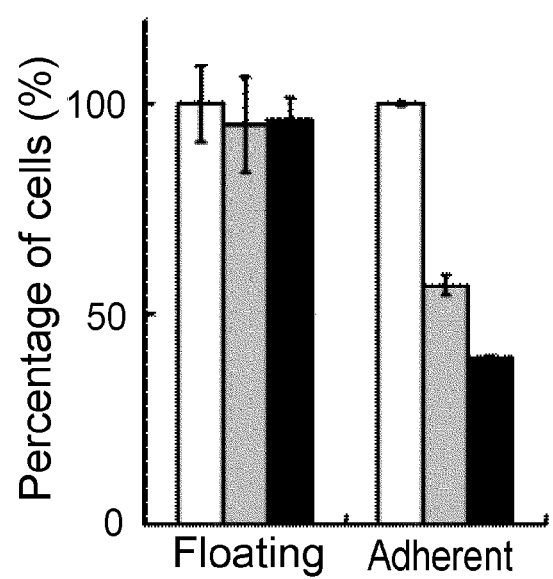
FIG. 29 shows the effects of chemotherapeutic agents on the growth of the Lgr5-positive adherent cancer stem cells and Lgr5-negative floating cancer stem cells of PLR123 cells. The number of living cells after treatment with 5-FU (10 µg/mL, gray column) or irinotecan (10 µg/mL, black column) is expressed as a percentage relative to the number of living cells cultured without the use of chemotherapeutic agents (white column). The results are the mean values of three experiments. The bars at the top of each column show standard deviations.
Figure 30:
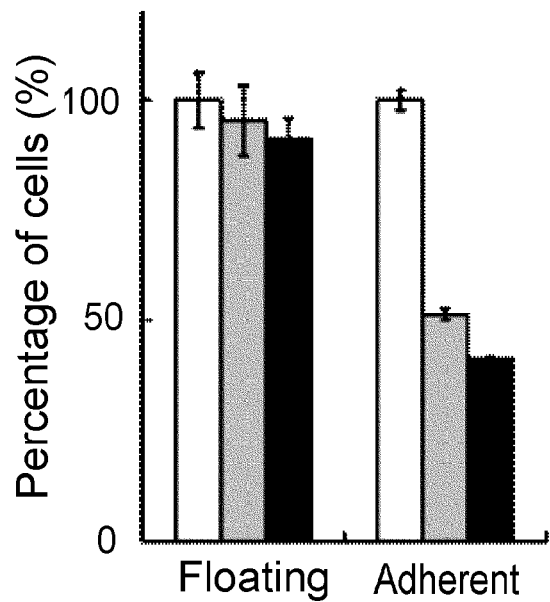
FIG. 30 shows the effects of 5-FU (10 µg/mL) or irinotecan (10 µg/mL) on the growth of the Lgr5-positive adherent cancer stem cells and Lgr5-negative floating cancer stem cells of PLR59 cells. The number of living cells after treatment with 5-FU (gray column) or irinotecan (black column) is expressed as a percentage relative to the number of living cells cultured in the absence of the above agents (white column).
Figure 31:
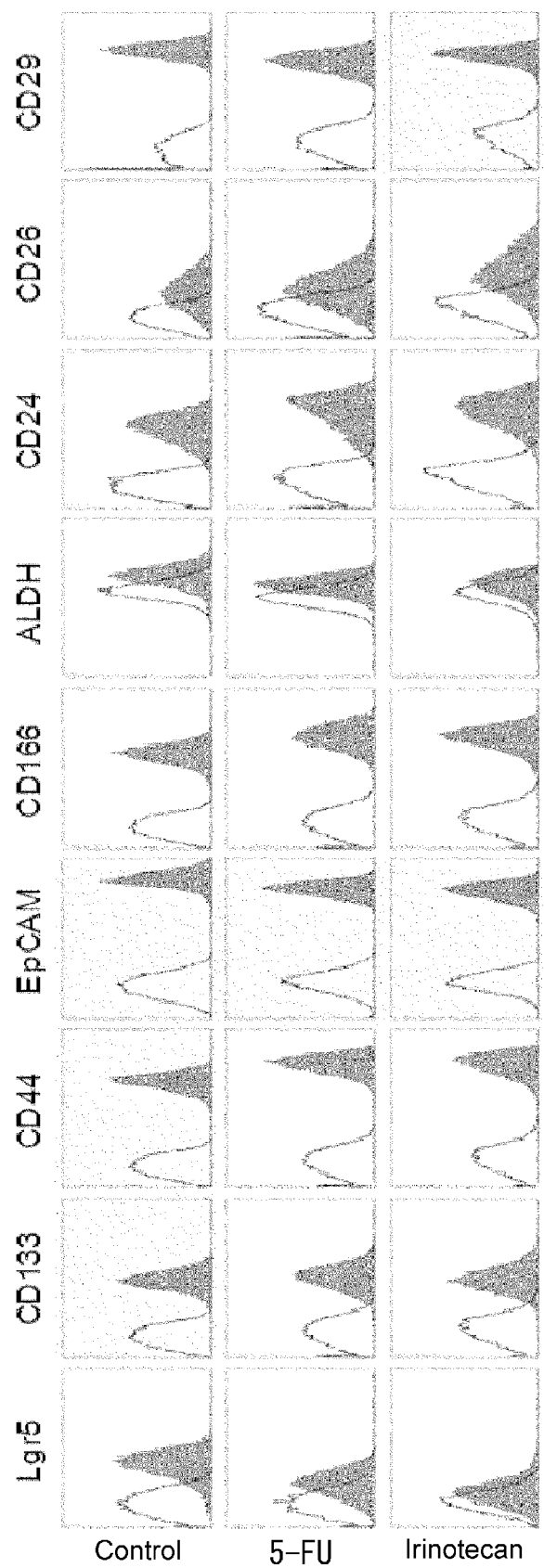
FIG. 31 shows changes of the Lgr5 expression in the adherent cancer stem cells of PLR123 cells after treatment with chemotherapeutic agents. The results of flow cytometry are shown. The upper indicates no chemotherapeutic agent (control). The middle indicates 5-FU-treated cells. The lower indicates irinotecan-treated cells. Gray indicates fluorescence intensity or ALDH activity after staining cells with the antibodies described. White indicates fluorescence intensity or ALDH activity of an ALDH inhibitor after staining cells with a control isotype antibody.
Figure 32:
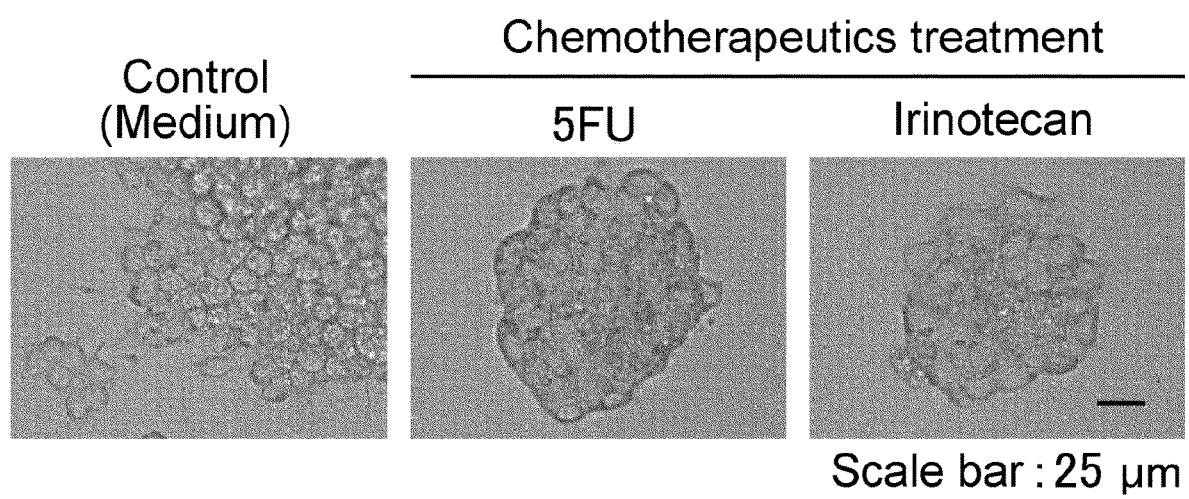
FIG. 32 presents a photograph showing alternate changes of the colon cancer stem cell phenotype as a result of culture conditions and chemotherapeutic agent treatment. The sensitivity of Lgr5-positive cancer stem cells to 5-FU and irinotecan was examined. Both 5-FU and irinotecan significantly inhibited the growth of Lgr5-positive cancer stem cells. After 3-day exposure to 5-FU or irinotecan, cells resistant to these chemotherapeutic agents appeared. The morphology of the drug-resistant cells was aggregation at high density. The scale bar indicates 25 μm.
Figure 33:
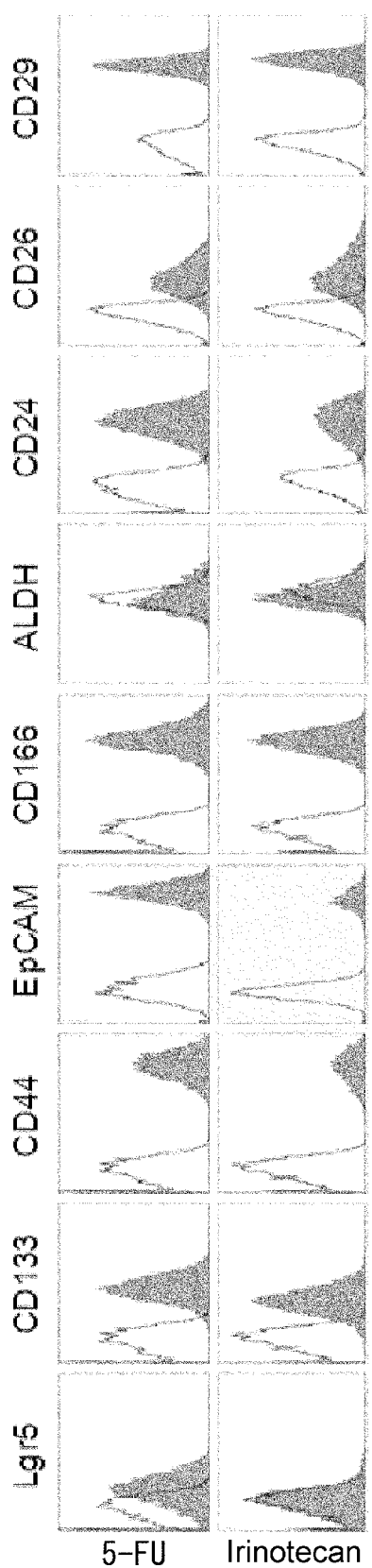
FIG. 33 shows results of the flow cytometric analysis of cancer stem cell markers after treating the adherent cancer stem cells of PLR59 with 5-FU or irinotecan. The upper indicates 5-FU-treated cells. The lower indicates irinotecan-treated cells. Gray indicates fluorescence intensity or ALDH activity after staining cells with the antibodies described. White indicates fluorescence intensity or ALDH activity of an ALDH inhibitor after staining cells with a control isotype antibody.

[Reference Example 4] Ability of Colon Cancer Stem Cells to Alternate from Lgr5-Positive to Lgr5-Negative One of the characteristics of cancer stem cells is their resistance to chemotherapeutic agents. Thus, the inventors investigated the sensitivity of colon cancer stem cells to 5-FU and irinotecan. As described above, Lgr5-positive cells grew with a doubling time of about 2.5 days, while Lgr5-negative cancer stem cells were in a static state in terms of growth. Treatment with 5-FU (10 µg/ml) or irinotecan (10 µg/ml) significantly inhibited the growth of Lgr5-positive colon cancer stem cells, but had no effect on the growth and survival of Lgr5-negative colon cancer stem cells (FIGS. 29 and 30). After 3 days of exposing Lgr5-positive colon cancer stem cells to 5-FU (10 µg/ml) or irinotecan (10 µg/ml), some of the cells became resistant to these chemotherapeutic agents. Surprisingly, the drug-resistant cells were negative for Lgr5 and their morphology was altered (FIGS. 31, 32, and 33), suggesting alteration from an Lgr5-positive state to an Lgr5-negative state.

Figure 34:
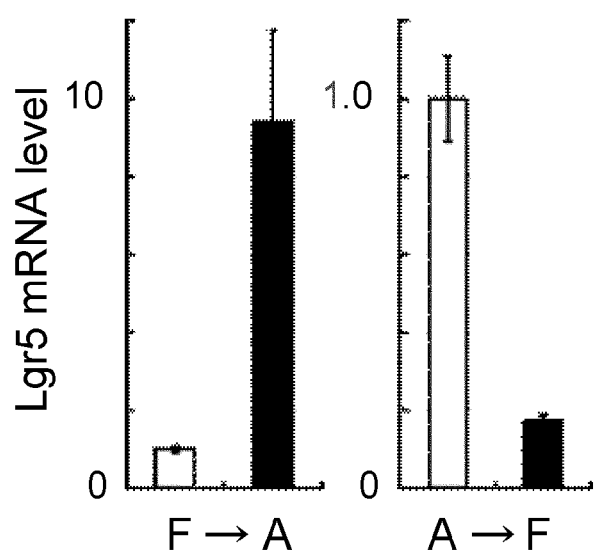
FIG. 34 shows the Lgr5 mRNA levels of PLR123 cells in adherent and floating cultures before (indicated as 1) and after transfer. FA indicates transfer from floating to adherent culture. A→F indicates transfer from adherent to floating culture. The results are the mean values of three experiments. The bars at the top of each column show the standard deviations.

To examine the alteration of Lgr5-negative colon cancer stem cells to an Lgr5-positive state, the inventors prepared Lgr5-negative colon cancer stem cells by irinotecan treatment, and adherently cultured them again in a serum-free stem cell culture solution. The cells became positive for Lgr5 and showed mesenchymal cell-like morphology (FIGS. 34 and 35), and at the same time started to grow. On the other hand, when Lgr5-positive adherent colon cancer stem cells were cultured in an ultra-low attachment plate, the inventors observed that some of the cells stopped growing, forming a spheroid-like structure, and showed a very low Lgr5 mRNA level (FIGS. 34 and 35).

Lgr5 mRNA was examined by quantitative real-time polymerase chain reaction as described below. Specifically, cDNA was synthesized with the First-Strand cDNA Synthesis Kit (SABiosciences) using as a template, total RNA isolated with the RNeasy Mini Kit including DNase treatment (Qiagen). Quantitative real-time PCR (QRT-PCR) analysis was conducted using the SYBR Green/Rox qPCR (SABiosciences) in the Mx3005P Real-Time PCR System (Stratagene). Values of fold induction were calculated using the 2-ΔΔCt method. GAPDH and ACTB were used as references. All the experiments were conducted in triplicate.

The following primers were used as primers for quantitative real-time PCR analysis to amplify the transcription products of the reaction:

```
Lgr5:
Forward primer:
                                          (SEQ ID NO: 1)
5'-AGTTTATCCTTCTGGTGGTAGTCC-3', Reverse primer:
                                          (SEQ ID NO: 2)
5'-CAAGATGTAGAGAAGGGGATTGA-3', GAPDH:
Forward primer:
                                          (SEQ ID NO: 3)
5'-CTCTGCTCCTCCTGTTCGAC-3', Reverse primer:
                                          (SEQ ID NO: 4)
5'-ACGACCAAATCCGTTGACTC-3', ACTB:
Forward primer:
                                          (SEQ ID NO: 5)
5'-AAGTCCCTTGCCATCCTAAAA-3', Reverse primer:
                                          (SEQ ID NO: 6)
5'-ATGCTATCACCTCCCCTGTG-3'
```

Based on the above results, the inventors concluded that colon cancer stem cells altered from an Lgr5-positive to an Lgr5-negative state, and that such alteration would require neither exogenous factors nor environmental niche.

Figure 36:
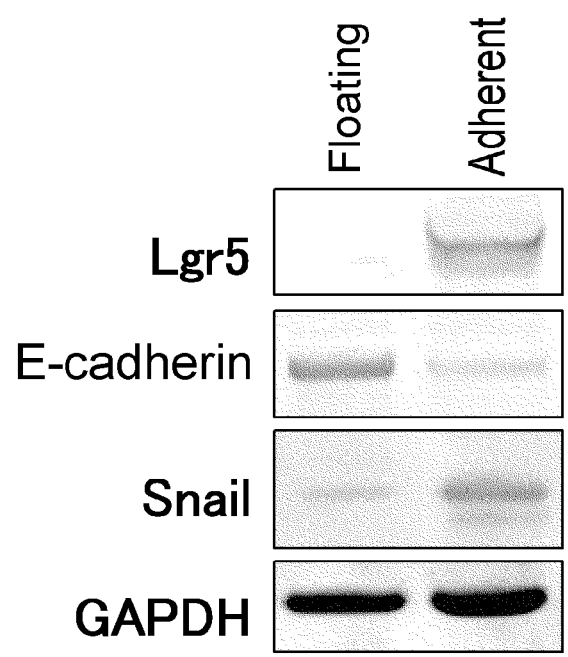
FIG. 36 presents a photograph showing results of the Western blot analysis of E-cadherin and Snail in the Lgr5-negative floating cancer stem cells and Lgr5-positive adherent cancer stem cells of PLR123 cells. The floating cancer stem cells expressed a high level of E-cadherin. The adherent cancer stem cells expressed a high level of Snail. GADPH was used as a loading control.
Figure 37:
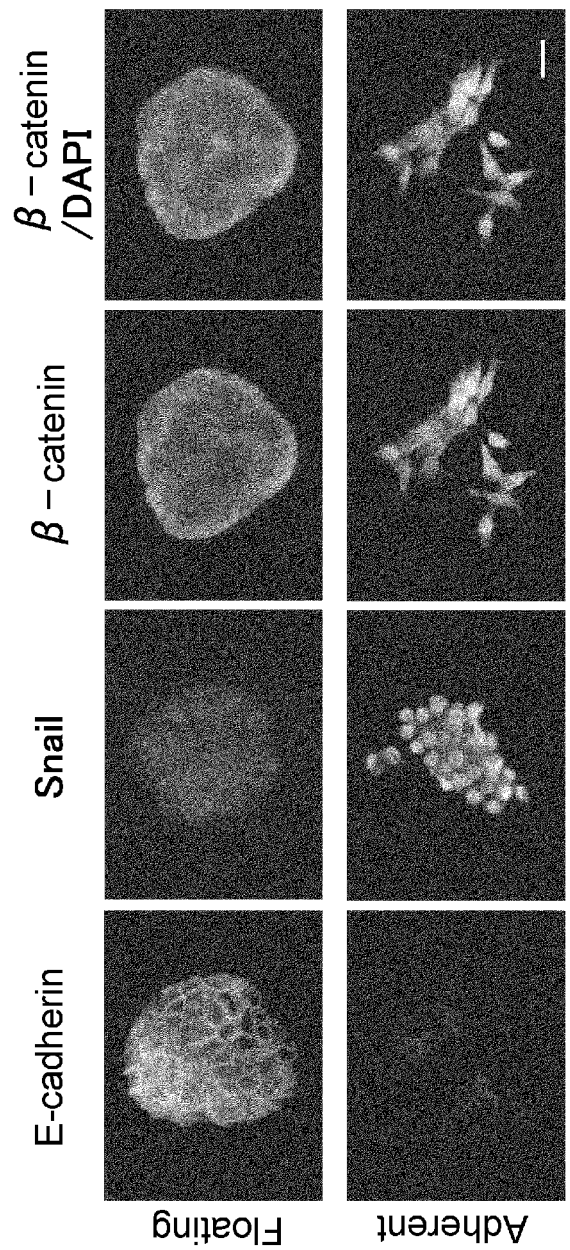
FIG. 37 presents a photograph showing results of immunocytochemistry with E-cadherin, Snail, and β-catenin antibodies in the Lgr5-negative floating cancer stem cells and Lgr5-positive adherent cancer stem cells of PLR123 cells. The floating cancer stem cells were epithelial-like cells expressing high levels of E-cadherin and β-catenin on the cell surface. The adherent cancer stem cells were mesenchymal-like cells with Snail and β-catenin localized in the nuclei. The scale bar indicates 25 μm.
Figure 38:
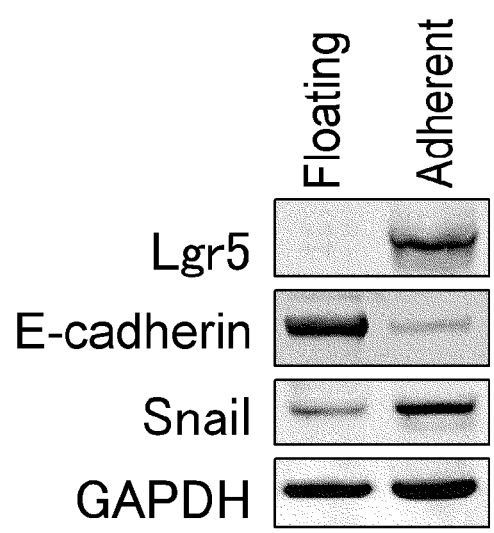
FIG. 38 presents a photograph showing results of the Western blot analysis of E-cadherin and Snail in the Lgr5-negative floating cancer stem cells and Lgr5-positive adherent cancer stem cells of PLR59 cells. The floating cancer stem cells expressed a high level of E-cadherin. The adherent cancer stem cells expressed a high level of Snail. GADPH was used as a loading control.
Figure 39:
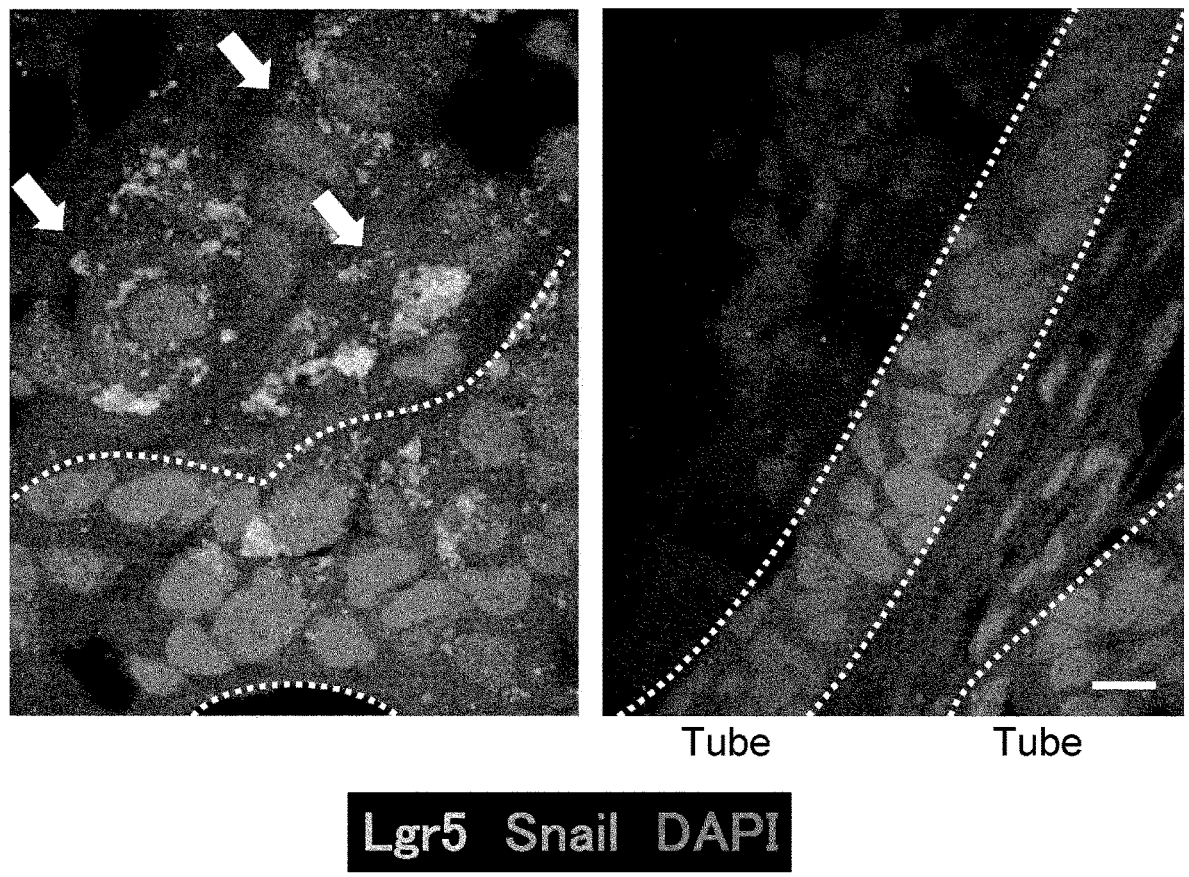
FIG. 39 presents a photograph showing results of immunohistochemistry of xenograft tissues (derived from PLR123 cells) with anti-Lgr5 and anti-Snail antibodies. Coexpression of nuclear Snail and cytoplasmic Lgr5 was detected in the budding area of EMT-like cells (left panel), but not in the tube (right panel). The arrow indicates an Lgr5-positive budding cell. The scale bar indicates 10 μm.

[Reference Example 5] EMT of Lgr5-Positive Colon Cancer Stem Cells In Vitro and In Vivo Mesenchymal-like cells expressing nuclear β-catenin are mobile or metastatic cancer stem cells that undergo EMT (Brabletz T, Jung A, Spaderna S, Hlubek F, Kirchner T (2005) Opinion: migrating cancer stem cells—an integrated concept of malignant tumor progression. Nat Rev Cancer 5: 744-749.). Lgr5-positive colon cancer stem cells are morphologically similar to mesenchymal cells. Thus, the inventors examined whether or not Lgr5-positive cancer stem cells are equivalent to mobile colon cancer stem cells. Western blot analysis demonstrated low-level expression of cell surface E-cadherin, high-level expression of Snail, and expression of nuclear localizing β-catenin (characteristic of EMT) in Lgr5-positive colon cancer stem cells (FIGS. 36, 37, and 38). On the other hand, Lgr5-negative colon cancer stem cells showed no signs of EMT. Specifically, cell surface E-cadherin was expressed at a high level, Snail was expressed at a low level, and no nuclear localization of β-catenin was observed. In addition, Snail and Lgr5 were co-expressed in cells that underwent EMT in the budding region of xenograft tumor tissue (FIG. 39), supporting the view that Lgr5-positive colon cancer stem cells are equivalent to mobile stem cells.

Figure 41:
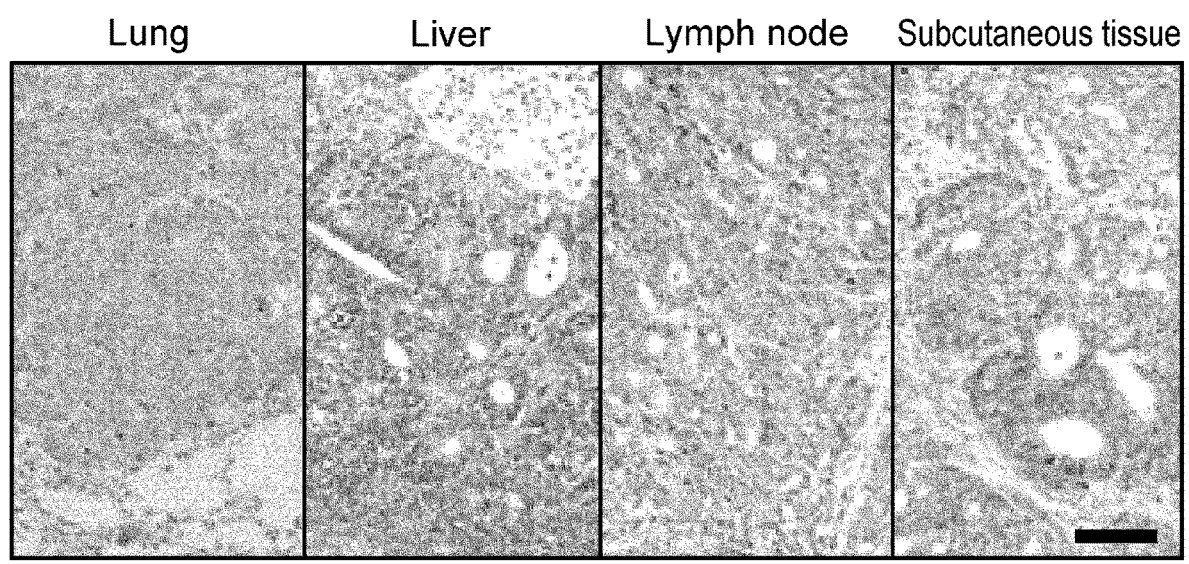
FIG. 41 presents a photograph showing results of the histopathological experiments with tumors in lungs, liver, lymph nodes, and subcutaneous tissues. In the lungs, the tumor cells showed undifferentiated tumor nests. In the liver and other organs, the tumor cells showed a tubular structure at multiple differentiation stages. The scale bar indicates 100 μm.

Furthermore, the inventors demonstrated that Lgr5-positive colon cancer stem cells formed tumors in multiple tissues including lungs, liver, and lymph nodes, and under the skin. Interestingly, until at least 40 days after intravenous injection of tumor cells, tumor with an epithelial tube structure was reconstructed in the liver, lymph nodes, and under the skin, but not in the lungs (FIGS. 40 and 41).

INDUSTRIAL APPLICABILITY

The invention provides a homogeneous cancer stem cell composition in which cells that have cancer-forming ability does not substantially coexist and those that have not, and which reproduces the cancer-tissue hierarchical structure; and a production method thereof. Gene expression analysis and proteomics analysis with this clonal (homogeneous) cell population are expected to enable identification of targets specifically expressed in cancer stem cells and identification of activated signal transduction pathways. Furthermore, the invention allows the continuous mass production of homogeneous cancer stem cells. It is expected that high-throughput analysis of drug candidates using the cancer stem cells should significantly increase the probability of finding drugs and diagnostic markers that are effective against cancer recurrence and metastasis which are the most serious outcomes in cancer patients.

The invention claimed is:

1. A method of identifying a drug candidate, comprising:
   (i) transplanting a sample comprising human colon cancer tissue into NOD/SCID/gamma$_c^{null}$ or NOD-scid/IL-2Rg$^{null}$ (NOG) mice to produce a human colon cancer cell mass;
   (ii) isolating the human colon cancer cell mass from the NOD/SCID/gamma$_c^{null}$ or NOD-scid/IL-2Rg$^{null}$ (NOG) mice;
   (iii) preparing cells from the human colon cancer cell mass;
   (iv) culturing the cells prepared from the human colon cancer cell mass in an in vitro adherent culture system using a serum-free stem cell medium, wherein culturing the cells comprises removing floating cells, and wherein adherent cells from the human colon cancer cell mass produce a population of human colon cancer stem cells from which cells with no cancer-forming ability have been substantially removed, wherein the population of human colon cancer stem cells are positive for LGR5;
   (v) culturing the population of human colon cancer stem cells from which cells with no cancer-forming ability have been substantially removed, wherein the population is characterized by reproducing a hierarchical structure of a cancer tissue, and the population is cultured as a spheroid culture under in vitro conditions to reproduce a characteristic structure of a cancer development process originating from human colon cancer stem cells or a biological property of human colon cancer stem cells;
   (vi) treating the cultured human colon cancer stem cells of (v) with a test substance;
   (vii) observing a change in the hierarchical structure formed from the human colon cancer stem cells, a cancer development process originating from the human colon cancer stem cells, or a biological property of the human colon cancer stem cells; and
   (viii) identifying a test substance that inhibits formation of the hierarchical structure formed from the human colon cancer stem cells, a cancer development process originating from the human colon cancer stem cells, or a biological property of the human colon cancer stem cells, as the drug candidate.

2. The method of claim 1, wherein the population of human colon cancer stem cells is substantially homogeneous.

3. The method of claim 1, wherein the frequency of human colon cancer stem cells in the population of human colon cancer stem cells in extreme limiting dilution analysis is 1/20 or higher.

4. The method of claim 1, wherein the population of human colon cancer stem cells comprises $1\times10^4$ or more human colon cancer stem cells.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: An artificially synthesized primer sequence

<400> SEQUENCE: 1
agtttatcct tctggtggta gtcc                                          24

<210> SEQ ID NO 2
<211> LENGTH: 23
<212> TYPE: DNA
<213> ORGANISM: Artificial Sequence
<220> FEATURE:
<223> OTHER INFORMATION: An artificially synthesized primer sequence

<400> SEQUENCE: 2
caagatgtag agaaggggat tga                                           23
```

```
<210> SEQ ID NO 3
<211> LENGTH: 20
<212> TYPE: DNA
<213> ORGANISM: Artificial Sequence
<220> FEATURE:
<223> OTHER INFORMATION: An artificially synthesized primer sequence

<400> SEQUENCE: 3
ctctgctcct cctgttcgac                                                 20

<210> SEQ ID NO 4
<211> LENGTH: 20
<212> TYPE: DNA
<213> ORGANISM: Artificial Sequence
<220> FEATURE:
<223> OTHER INFORMATION: An artificially synthesized primer sequence

<400> SEQUENCE: 4
acgaccaaat ccgttgactc                                                 20

<210> SEQ ID NO 5
<211> LENGTH: 21
<212> TYPE: DNA
<213> ORGANISM: Artificial Sequence
<220> FEATURE:
<223> OTHER INFORMATION: An artificially synthesized primer sequence

<400> SEQUENCE: 5
aagtcccttg ccatcctaaa a                                               21

<210> SEQ ID NO 6
<211> LENGTH: 20
<212> TYPE: DNA
<213> ORGANISM: Artificial Sequence
<220> FEATURE:
<223> OTHER INFORMATION: An artificially synthesized primer sequence

<400> SEQUENCE: 6
atgctatcac ctcccctgtg                                                 20
```